United States Patent
Li et al.

(10) Patent No.: US 9,891,224 B2
(45) Date of Patent: Feb. 13, 2018

(54) BIOMARKERS FOR AGGRESSIVE PROSTATE CANCER

(71) Applicant: THE JOHNS HOPKINS UNIVERSITY, Baltimore, MD (US)

(72) Inventors: Danni Li, Baltimore, MD (US); Daniel W. Chan, Clarksville, MD (US); Hui Zhang, Ellicott City, MD (US); Xiangchun Wang, Rockville, MD (US)

(73) Assignee: The Johns Hopkins University, Baltimore, MD (US)

( * ) Notice: Subject to any disclaimer, the term of this patent is extended or adjusted under 35 U.S.C. 154(b) by 664 days.

(21) Appl. No.: 14/375,535

(22) PCT Filed: Jan. 30, 2013

(86) PCT No.: PCT/US2013/023837
§ 371 (c)(1),
(2) Date: Jul. 30, 2014

(87) PCT Pub. No.: WO2013/116331
PCT Pub. Date: Aug. 8, 2013

(65) Prior Publication Data
US 2015/0276746 A1    Oct. 1, 2015

Related U.S. Application Data

(60) Provisional application No. 61/592,154, filed on Jan. 30, 2012, provisional application No. 61/593,593, filed on Feb. 1, 2012, provisional application No. 61/606,654, filed on Mar. 5, 2012.

(51) Int. Cl.
G01N 33/574    (2006.01)

(52) U.S. Cl.
CPC .......... *G01N 33/57434* (2013.01); *G01N 2333/8146* (2013.01); *G01N 2333/948* (2013.01); *G01N 2800/56* (2013.01)

(58) Field of Classification Search
None
See application file for complete search history.

(56) References Cited

U.S. PATENT DOCUMENTS

| | | | |
|---|---|---|---|
| 2003/0232400 A1* | 12/2003 | Radka | C07K 14/71 435/7.23 |
| 2005/0272052 A1 | 12/2005 | Shekar et al. | |
| 2007/0099251 A1* | 5/2007 | Zhang | G01N 33/574 435/7.23 |
| 2009/0060908 A1 | 3/2009 | Cardarelli et al. | |

FOREIGN PATENT DOCUMENTS

| | | | |
|---|---|---|---|
| WO | WO 2010/011357 | * | 1/2010 |
| WO | 2011-127219 A1 | | 10/2011 |
| WO | WO 2011/127219 | * | 10/2011 |

OTHER PUBLICATIONS

Nelson (Bioanalysis, 2009, 1:1431-1444).*
Li et al (Analytical Chemistry, 2011, 83:8509-8516).*
Kawasaki et al (Glycobiology, 2009, 19:437-450).*
Loo et al (Journal of Proteome Research, 2010, 9:5496-5500).*
Li, Y., et al., "Detection and verification of glycosylation patterns of glycop0roteins from clinical specimens using lectin microarrays and lectin-based immunosorbent arrays", Analytical Chemistry, vol. 83, No. 22, pp. 8509-8516, (Nov. 15, 2011).
Ahn, H., et al., "Generation of antibodies recognizing an aberrant glycoform of human tissue inhibitor of metalloproteinase-1 (TIMP-1) using decoy immunization and phage display", Journal of Biotechnology, vol. 151, No. 2, pp. 225-230 (Dec. 15, 2010).

* cited by examiner

*Primary Examiner* — Laura B Goddard
(74) *Attorney, Agent, or Firm* — Johns Hopkins Technology Ventures

(57) ABSTRACT

The present invention relates to the field of biomarkers. More specifically, the present invention relates to biomarkers useful in diagnosing aggressive prostate cancer. In one embodiment, a method for identifying patients as having or likely to have aggressive prostate cancer comprises the steps of (a) obtaining a biological sample from the patient; (b) performing an assay on the biological sample to detect fucosylated fucosylated DPP-4, sTIE-2, sVEGFR-1, and FUT8; and (c) identifying the patient as having or likely to have aggressive prostate cancer if there is a statistically significant difference in the levels of fucosylated TIMP-1, fucosylated DPP-4, sTIE-2, sVEGFR-1 and FUT8.

14 Claims, 24 Drawing Sheets

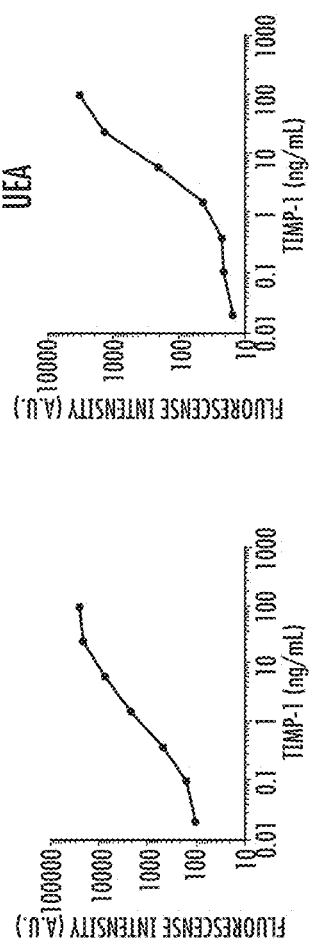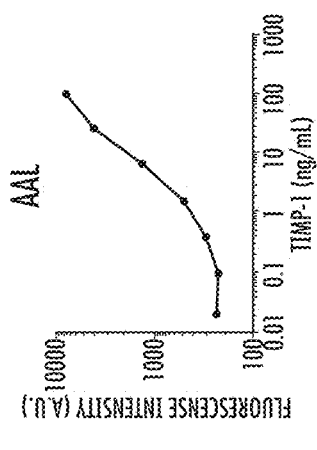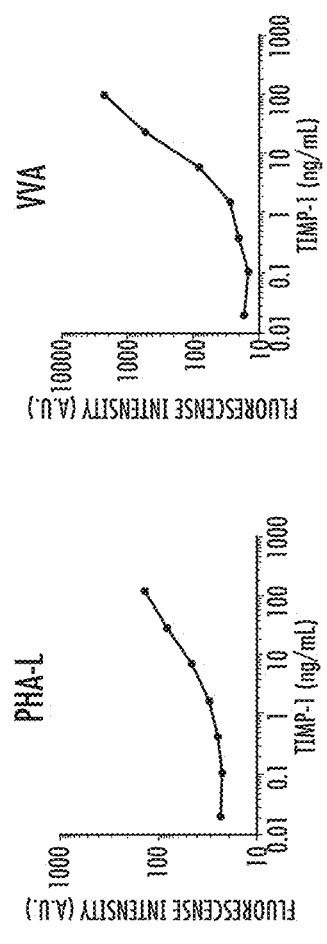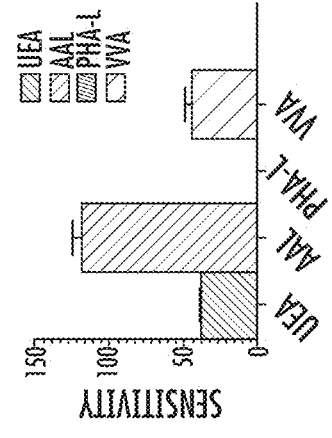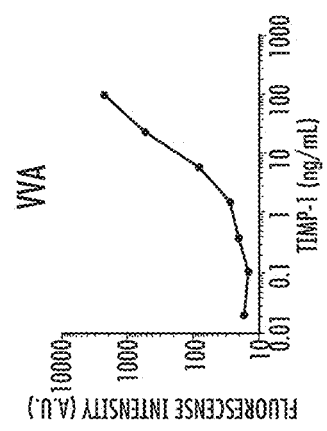
FIG. 3A  FIG. 3B  FIG. 3C  FIG. 3D  FIG. 3E  FIG. 3F

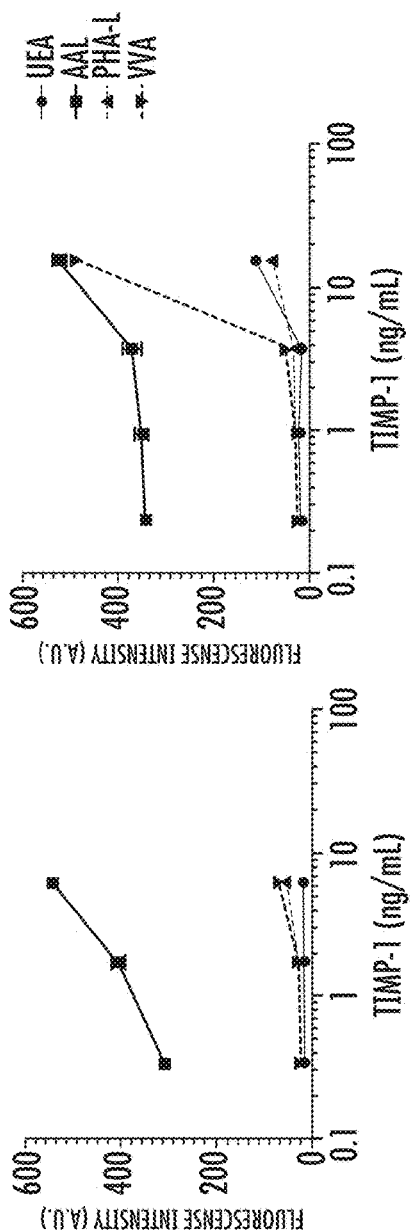
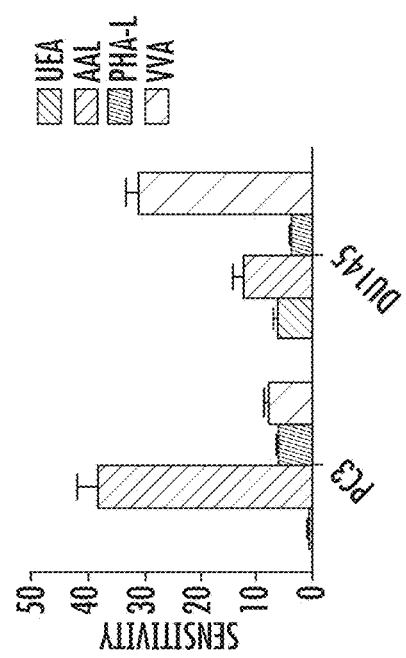
FIG. 4A
FIG. 4B
FIG. 4C

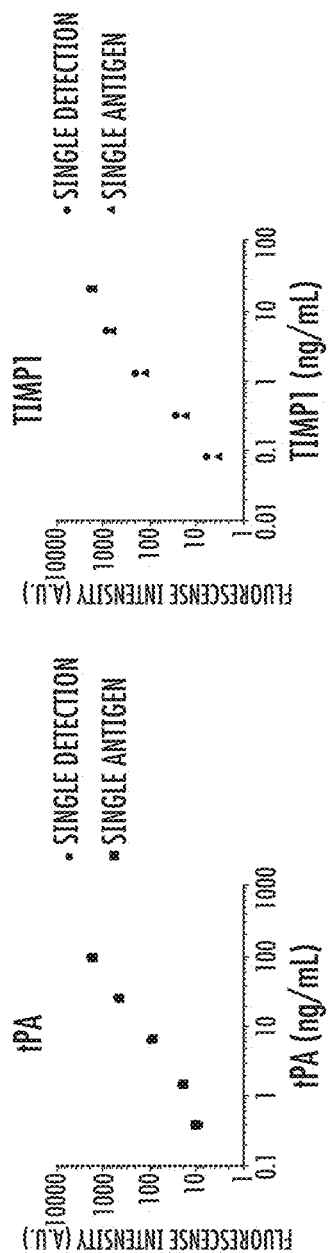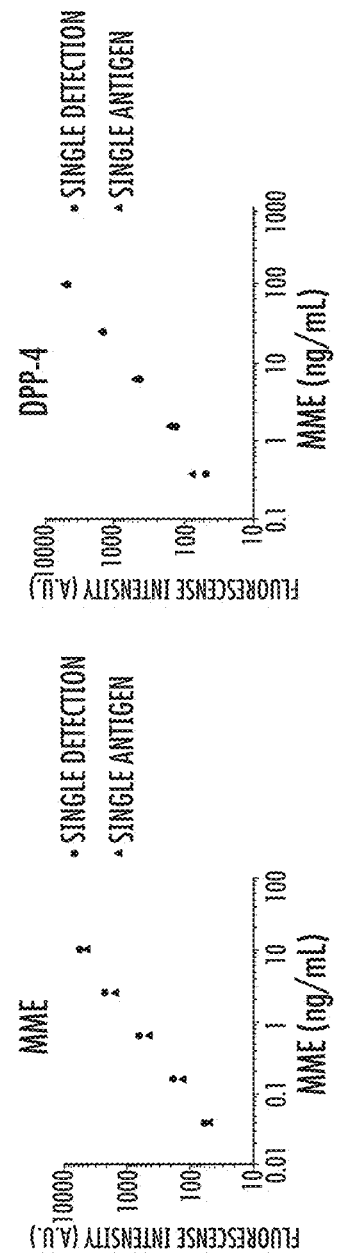

SUMMARY OF 10 INDIVIDUAL PROSTATE CANCER AAL AND
FUT8 IMMUNOHISTOCHEMISTRY

| SCORE | AAL (n=10) | | FUT8 (n=10) | |
|---|---|---|---|---|
| | TUMOR | PERCENT POSITIVE (%) | TUMOR | PERCENT POSITIVE (%) |
| 3 | 4 | 40% | 5 | 50% |
| 2 | 5 | 50% | 2 | 20% |
| 1 | 1 | 10% | 2 | 20% |
| 0 | 0 | 0 | 1 | 10% |
| | STROMAL | | STROMAL | |
| 3 | 0 | 0 | 0 | 0% |
| 2 | 0 | 0 | 0 | 0% |
| 1 | 2 | 20% | 3 | 30% |
| 0 | 8 | 80% | 7 | 70% |

SCORING BASED ON PROTEIN EXPRESSION
0 = NO STAINING; 1 = WEAK STAINING; 2 = MEDIUM
STAINING, 3 = STRONG STAINING

*FIG. 18B*

BIOMARKERS FOR AGGRESSIVE PROSTATE CANCER

CROSS-REFERENCE TO RELATED APPLICATIONS

This application is a 35 U.S.C. § 371 U.S. national entry of International Application PCT/US2013/023837 having an international filing date of Jan. 30, 2013, which claims the benefit of U.S. Provisional Application No. 61/592,154, filed Jan. 30, 2012, U.S. Provisional Application No. 61/593,593, filed Feb. 1, 2012, and U.S. Provisional Application No. 61/606,654, filed Mar. 5, 2012, all of which are incorporated herein by reference in their entireties.

STATEMENT OF GOVERNMENTAL INTEREST

This invention was made with government support under grant number CA152813 awarded by the National Institutes of Health. The government has certain rights in the invention.

FIELD OF THE INVENTION

The present invention relates to the field of biomarkers. More specifically, the present invention relates to biomarkers useful in diagnosing aggressive prostate cancer.

BACKGROUND OF THE INVENTION

Prostate cancer is the most common malignancy in men and the second leading cause of death from cancer in the United States. Metastases are the major cause of death from cancer. Therefore, aggressive (AG) prostate cancer leads to a higher metastasis rate and requires early detection and treatment. Since the discovery of prostate-specific antigen (PSA), assays that detect this serum biomarker (together with digital rectal exams) have been used for the screening of prostate cancer. PSA testing has resulted in early detection and intervention. However, the major limitation of PSA is the low specificity and high prevalence of detecting benign prostatic hyperplasia, especially in older men. Early detection based on PSA testing also fails to distinguish aggressive prostate cancer from non-aggressive prostate cancer. Indeed, with the illustration of the limitations of the current PSA-based screening method, a recently published study randomly assigned 76 693 men at 10 U.S. study centers to receive either annual PSA screening (38 343 subjects) or usual care as the control (38 350 subjects); this study reported no statistical differences in prostate cancer specific mortality between the groups after 7-10 years of follow-up.

Besides preoperative PSA, clinical risk assessment tools for prostate cancer metastasis before surgery largely rely on the prostate biopsy Gleason score. However, the risk assessment based on this clinical criterion is too imprecise to be useful due to biopsy sampling error and interobserver grading differences. It is also unable to be used as a screening test for early detection of aggressive prostate cancer. Currently, aggressive prostate cancer is under-detected and under treated while nonaggressive prostate cancer is overdetected and overtreated. Consequences of the difficulty of distinguishing the aggressive and nonaggressive prostate cancer are that prostate cancer patients suffer from unnecessary surgeries, and health care faces massive unnecessary expenditures. Therefore, reliable biomarkers to distinguish aggressive and nonaggressive prostate cancer are badly needed to prevent patients with nonaggressive prostate cancer from overtreatment and to allow patients with aggressive cancer to receive appropriate treatment earlier in the course of their disease.

SUMMARY OF THE INVENTION

The present invention is based, at least in part, on the identification of proteins whose expression is significantly altered in aggressive prostate tumors. In one aspect, the present invention provides assays useful for identifying patients has having or likely to have aggressive prostate cancer. The assays can be singleplex or multiplex assays. In certain embodiments, the assay utilizes antibodies to capture biomarker proteins of interest. The assays can further use antibodies to detect and quantify biomarker proteins of interest. The assay can also use lectins to detect and quantify biomarker proteins of interest. In certain embodiments, the assay utilizes both antibodies and lectins to detect and measure biomarker proteins of interest.

In one embodiment, a method for identifying patients as having or likely to have aggressive prostate cancer comprises the steps of (a) obtaining a biological sample from the patient; (b) performing an assay on the biological sample to detect fucosylated TIMP-1, fucosylated DPP-4, sTIE-2, sVEGFR-1, and FUT8; and (c) identifying the patient as having or likely to have aggressive prostate cancer if there is a statistically significant difference in the levels of fucosylated TIMP-1, fucosylated DPP-4, sTIE-2, sVEGFR-1 and FUT8 as compared to corresponding levels in a control sample that correlates to non-aggressive prostate cancer. In another embodiment, a method for identifying aggressive prostate cancer in a patient comprises the steps of (a) measuring the levels of one or more biomarkers in a sample collected from the patient; and (b) comparing the levels of the one or more biomarkers with predefined levels of the same biomarkers that correlate to a patient having aggressive prostate cancer and predefined levels of the same biomarkers that correlate to a patient not having aggressive prostate cancer, wherein a correlation to one of the predefined levels provides the identification.

In specific embodiments, the one or more biomarkers is selected from the group consisting of sTIE-2, sVEGFR-1, fucosylated TIMP-1, fucosylated DPP-4, and FUT8. In other embodiments, the one or more biomarkers comprises sTIE-2, sVEGFR-1, fucosylated TIMP-1, fucosylated DPP-4, and FUT8. The sample can be a blood, plasma, or serum sample. In certain embodiments, the sample is a serum sample. In particular embodiments, the measuring step is performed using an immunoassay. In other embodiments, the measuring step is performed using mass spectrometry. In a specific embodiment, the correlation to a patient not having aggressive prostate cancer refers to a patient having non-aggressive prostate cancer. In another specific embodiment, the correlation to a patient not having aggressive prostate cancer refers to a patient not having cancer.

In another embodiment, the present invention provides a method for diagnosing aggressive prostate cancer in a patient comprising the steps of (a) collecting a serum sample from the patient; (b) detecting the levels of a panel of biomarkers in the sample collected from the patient, wherein the panel of biomarkers comprises one or more of sTIE-2, sVEGFR-1, fucosylated TIMP-1, fucosylated DPP-4, and FUT8; and (c) comparing the levels of the panel of biomarkers with predefined levels of the same panel of biomarkers that correlate to a patient having aggressive prostate cancer and predefined levels of the same panel of biomarkers that correlate to a patient not having aggressive prostate cancer, wherein a correlation to one of the predefined levels provides the diagnosis.

In another aspect, the present invention provides methods for treating prostate cancer in a patient. In a specific embodiment, the method comprises the steps of (a) collecting a serum sample from the patient; (b) detecting the levels of a panel of biomarkers in the sample collected from the patient, wherein the panel of biomarkers comprises one or more of sTIE-2, sVEGFR-1, fucosylated TIMP-1, fucosylated DPP-4, and FUT8; (c) comparing the levels of the panel of biomarkers with predefined levels of the same panel of biomarkers that correlate to a patient having aggressive prostate cancer and predefined levels of the same panel of biomarkers that correlate to a patient not having aggressive prostate cancer, wherein a correlation to one of the predefined levels provides the diagnosis; and (d) treating the patient with an appropriate therapeutic regimen for aggressive prostate cancer if the diagnosis of the patient correlates to aggressive prostate cancer or treating the patient with an appropriate therapeutic regimen for non-aggressive prostate cancer if the diagnosis of the patient correlates to non-aggressive prostate cancer.

In yet another aspect, the present invention provides methods for determining the aggressive prostate cancer status in a patient. In a specific embodiment, the method comprises the steps of (a) collecting a sample from the patient; (b) measuring the levels of a panel of biomarkers in the sample collected from the patient, wherein the panel of biomarkers comprises one or more of sTIE-2, sVEGFR-1, fucosylated TIMP-1, fucosylated DPP-4, and FUT8; and (c) comparing the levels of the panel of biomarkers with predefined levels of the same panel of biomarkers that correlate to one or more aggressive prostate cancer statuses selected from the group consisting of having aggressive prostate cancer, not having aggressive prostate cancer, progressing aggressive prostate cancer, and regressing aggressive prostate cancer, wherein a correlation to one of the predefined levels determines the aggressive prostate cancer status of the patient.

In another embodiment, the present invention provides a multiplex assay for distinguishing aggressive from non-aggressive prostate cancer comprising the steps of (a) incubating a sample comprising biomarker proteins of interest obtained from a patient with a mixture of magnetic beads coupled with monoclonal antibodies that specifically bind the biomarker proteins of interest, wherein the biomarker proteins of interest comprise fucosylated tissue inhibitor of metallopeptidase 1 (TIMP-1) and fucosylated dipeptidyl peptidase-IV (DPP-4); (b) adding a mixture of biotinylated lectins that specifically bind fucosylated TIMP-1 and fucosylated DPP-4; (c) adding a streptavidin labeled fluorescent marker that binds the biotinylated lectins bound to the fucosylated TIMP-1 and fucosylated DPP-4; (d) detecting fucosylated TIMP-1 and fucosylated DPP-4; and (e) identifying the patient as having aggressive prostate cancer if the fluorescence intensity of fucosylated TIMP-1 and fucosylated DPP-4 is statistically significantly increased relative to a reference that correlates to non-aggressive prostate cancer. In certain embodiments, the sample is a serum sample. In other embodiments, the biotinylated lectin is *Ulex europeaus* agglutinin (UEA). In further embodiments, the biotinylated lectin is phytohemagglutinin-L (PHA-L). In specific embodiments, the fluorescent marker is phycoerythrin. In other embodiments, the sample comprises about 300 ng of protein. In a specific embodiment, the sample comprises less than about 400 ng of protein. The sample can comprises about 100 ng to about 1 mg of protein.

In particular embodiments, the biomarker proteins further comprise soluble form of the TIE-2 receptor (sTIE-2), soluble form of the vascular endothelial growth factor receptor 1 (sVEGFR-1), and alpha (1,6) fucosyltransferase (FUT8). In such embodiments, the multiplex assay can further comprise adding a mixture of biotinylated detection antibodies; adding a streptavidin labeled fluorescent marker that binds the biotinylated antibodies bound to sTIE-2, sVEGFR-1, and FUT8; detecting sTIE-2, sVEGFR-1, and FUT8; and identifying the patient as having aggressive prostate cancer if the fluorescence intensity of sTIE-2, FUT8, fucosylated TIMP-1 and fucosylated DPP-4 is statistically significantly increased relative to a reference and the fluorescence intensity of sVEGFR-1 is statistically significantly decreased relative to a reference. The biotinylated detection antibodies can be immunoglobulin G antibodies.

In a specific embodiment, a multiplex assay for distinguishing aggressive from non-aggressive prostate cancer comprises the steps of (a) incubating a sample comprising biomarker proteins of interest obtained from a patient with a mixture of magnetic beads coupled with monoclonal antibodies that specifically bind the biomarker proteins of interest, wherein the biomarker proteins of interest comprise sTIE-2, sVEGFR-1, FUT8, fucosylated TIMP-1 and fucosylated DPP-4; (b) adding a mixture of biotinylated detection antibodies; (c) adding a mixture of biotinylated lectins that specifically bind fucosylated TIMP-1 and fucosylated DPP-4; (d) adding a streptavidin labeled fluorescent marker that binds the biotinylated antibodies bound to sTIE-2, sVEGFR-1, and FUT8; (e) adding a streptavidin labeled fluorescent marker that binds the biotinylated lectins bound to the fucosylated TIMP-1 and fucosylated DPP-4; (f) detecting sTIE-2, sVEGFR-1, FUT8, fucosylated TIMP-1 and fucosylated DPP-4; and (g) identifying the patient as having aggressive prostate cancer if the fluorescence intensity of sTIE-2, FUT8, fucosylated TIMP-1 and fucosylated DPP-4 is statistically significantly increased relative to a reference and the fluorescence intensity of sVEGFR-1 is statistically significantly decreased relative to a reference. The sample can be a blood, plasma or serum sample. The sample can be from other biological fluids/tissues. In one embodiment, the biotinylated lectin is UEA. In another embodiment, the biotinylated lecin is PHA-L. In certain embodiments, the biotinylated detection antibodies are immunoglobulin G antibodies. In specific embodiments, the fluorescent marker is phycoerythrin. In other embodiments, the sample comprises about 300 ng of protein. In a specific embodiment, the sample comprises less than about 400 ng of protein. The sample can comprises about 100 ng to about 1 mg of protein.

In other embodiments, the present invention provides kits useful for distinguishing aggressive prostate cancer from non-aggressive prostate cancer. In a specific embodiment, a kit comprises (a) magnetic beads for conjugating to antibodies that specifically bind biomarker proteins of interest, wherein the biomarkers proteins of interest comprise sTIE-2, sVEGFR-1, FUT8, fucosylated TIMP-1, and fucosylated DPP-4; (b) monoclonal antibodies that specifically bind the biomarker proteins of interest; (c) biotinylated immunoglobulin G detection antibodies; (d) biotinylated lectins that specifically bind fucosylated TIMP-1 and fucosylated DPP-4; and (e) streptavidin labeled fluorescent marker.

BRIEF DESCRIPTION OF THE FIGURES

FIG. 3. (A) Establishment of the integrated system for protein quantification and glycan detection in TIMP-1: magnetic bead-based immunoassay for TIMP-1 protein; (B-E), dose-response curves of UEA, AAL, PHA-L, and VVA immunosorbent assays for TIMP-1; F, glycan profile of the recombinant TIMP-1. The glycan profile was established using the sensitivity of the dose-response curves, calculated as changes of fluorescence intensity per TIMP-1 concentration. A.U., arbitrary units.

FIG. 4. Dose-response curves of the LISAs for TIMP-1 from culture media of PC3 cells (A) and DU145 cells (B). C, comparison of glycan profiles of TIMP-1 from PC3 and DU145. Protein concentrations of TIMP-1 in these samples were quantified by TIMP-1 immunoassay and plotted against the signals detected in these samples by LISAs. The plotted results are shown as the dose-response curves. A.U., arbitrary units.

FIG. 12. Dose response curves of the single-antigen and single-detection cross-reactivity studies for tPA (A), TIMP-1(B), MME (C), and DPP-4(D).

DETAILED DESCRIPTION OF THE INVENTION

Figure 1:
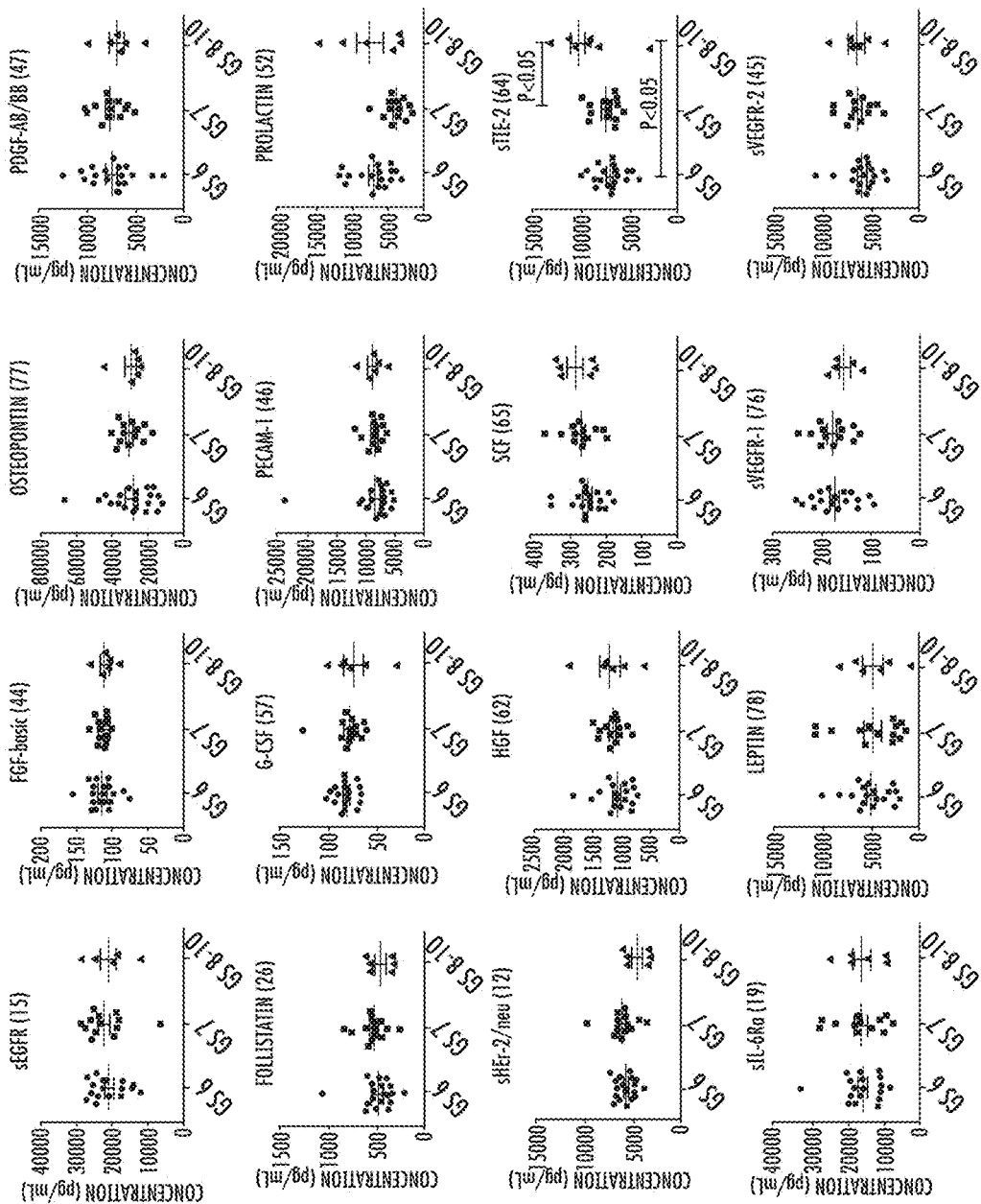
FIG. 1. Expression of 16 serum angiogenic factors in prostate cancer patients with Gleason scores of 6, 7, and 8-10.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. Definitions

As used herein, the term "antibody" is used in reference to any immunoglobulin molecule that reacts with a specific antigen. It is intended that the term encompass any immunoglobulin (e.g., IgG, IgM, IgA, IgE, IgD, etc.) obtained from any source (e.g., humans, rodents, non-human primates, caprines, bovines, equines, ovines, etc.). Specific types/examples of antibodies include polyclonal, monoclonal, humanized, chimeric, human, or otherwise-human-suitable antibodies. "Antibodies" also includes any fragment or derivative of any of the herein described antibodies.

As used herein, the term "comparing" refers to making an assessment of how the proportion, level or cellular localization of one or more biomarkers in a sample from a patient relates to the proportion, level or cellular localization of the corresponding one or more biomarkers in a standard, reference or control sample. For example, "comparing" may refer to assessing whether the proportion, level, or cellular localization of one or more biomarkers in a sample from a patient is the same as, more or less than, or different from the proportion, level, or cellular localization of the corresponding one or more biomarkers in standard, reference or control sample. More specifically, the term may refer to assessing whether the proportion, level, or cellular localization of one or more biomarkers in a sample from a patient is the same as, more or less than, different from or otherwise corresponds (or not) to the proportion, level, or cellular localization of predefined biomarker levels/ratios that correspond to, for example, a patient having aggressive prostate cancer, not having aggressive prostate cancer (e.g., non-aggressive prostate cancer or no cancer), is responding to treatment for aggressive prostate cancer, is not responding to treatment for aggressive prostate cancer, is/is not likely to respond to a particular aggressive prostate cancer treatment, or having/not having another disease or condition. In a specific embodiment, the term "comparing" refers to assessing whether the level of one or more biomarkers of the present invention in a sample from a patient is the same as, more or less than, different from other otherwise correspond (or not) to levels/ratios of the same biomarkers in a control sample (e.g., predefined levels/ratios that correlate to uninfected individuals, non-aggressive prostate cancer, standard aggressive prostate cancer levels/ratios, etc.).

In another embodiment, the term "comparing" refers to making an assessment of how the proportion, level or cellular localization of one or more biomarkers in a sample from a patient relates to the proportion, level or cellular localization of another biomarker in the same sample. For example, a ratio of one biomarker to another from the same patient sample can be compared. In another embodiment, a level of one biomarker in a sample (e.g., a post-translationally modified biomarker protein) can be compared to the level of the same biomarker (e.g., unmodified biomarker protein) in the sample. In a specific embodiment, the proportion of a fucosylated biomarker protein can be compared to the unmodified protein, both of which are measured in the same patient sample. Ratios of modified:unmodified biomarker proteins can be compared to other protein ratios in the same sample or to predefined reference or control ratios.

As used herein, the terms "identifies," "indicates" or "correlates" (or "identifying," "indicating" or "correlating," or "identification," "indication" or "correlation," depending on the context) in reference to a parameter, e.g., a modulated proportion, level, or cellular localization in a sample from a patient, may mean that the patient has aggressive prostate cancer. In specific embodiments, the parameter may comprise the level of one or more biomarkers of the present invention. A particular set or pattern of the amounts of one or more biomarkers may identify the patient as having aggressive prostate cancer (i.e., correlates to a patient having aggressive prostate cancer). In other embodiments, a correlation could be that the ratio of a post-translationally modified protein (e.g., fucosylation) to the unmodified protein indicates (or a change in the ratio over time or as compared to a reference/control ratio) that the patient has aggressive prostate cancer. In specific embodiments, an indication could be the ratio of a fucosylated peptide to the non-fucosylated form, or any other combination in which a change in one peptide causes or is accompanied by a change in another.

In other embodiments, a particular set or pattern of the amounts of one or more biomarkers may identify the patient as being unaffected (i.e., indicates a patient does not have aggressive prostate cancer, a patient has non-aggressive prostate cancer, or a patient does not have cancer). In certain embodiments, "identifying," "indicating," or "correlating," as used according to the present invention, may be by any linear or non-linear method of quantifying the relationship between levels/ratios of biomarkers to a standard, control or comparative value for the assessment of the diagnosis, prediction of aggressive prostate cancer or aggressive prostate cancer progression, assessment of efficacy of clinical treatment, identification of a patient that may respond to a particular treatment regime or pharmaceutical agent, monitoring of the progress of treatment, and in the context of a screening assay, for the identification of an anti-aggressive prostate cancer therapeutic.

The terms "patient," "individual," or "subject" are used interchangeably herein, and refer to a mammal, particularly, a human. The patient may have mild, intermediate or severe disease. The patient may be treatment naïve, responding to any form of treatment, or refractory. The patient may be an individual in need of treatment or in need of diagnosis based on particular symptoms or family history. In some cases, the terms may refer to treatment in experimental animals, in veterinary application, and in the development of animal models for disease, including, but not limited to, rodents including mice, rats, and hamsters; and primates.

The terms "measuring" and "determining" are used interchangeably throughout, and refer to methods which include obtaining a patient sample and/or detecting the level of a biomarker(s) in a sample. In one embodiment, the terms refer to obtaining a patient sample and detecting the level of one or more biomarkers in the sample. In another embodiment, the terms "measuring" and "determining" mean detecting the level of one or more biomarkers in a patient sample. Measuring can be accomplished by methods known in the art and those further described herein. The terms are also used interchangeably throughout with the term "detecting."

The terms "sample," "patient sample," "biological sample," and the like, encompass a variety of sample types obtained from a patient, individual, or subject and can be used in a diagnostic or monitoring assay. The patient sample may be obtained from a healthy subject, a diseased patient or a patient having associated symptoms of aggressive prostate cancer. Moreover, a sample obtained from a patient can be divided and only a portion may be used for diagnosis. Further, the sample, or a portion thereof, can be stored under conditions to maintain sample for later analysis. The definition specifically encompasses blood and other liquid samples of biological origin (including, but not limited to, peripheral blood, serum, plasma, cerebrospinal fluid, urine, saliva, stool and synovial fluid), solid tissue samples such as a biopsy specimen or tissue cultures or cells derived therefrom and the progeny thereof. In a specific embodiment, a sample comprises a blood sample. In another embodiment, a sample comprises a plasma sample. In yet another embodiment, a serum sample is used.

The definition of "sample" also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry. In certain embodiments, a sample comprises an optimal cutting temperature (OCT)-embedded frozen tissue sample.

The terms "specifically binds to," "specific for," and related grammatical variants refer to that binding which occurs between such paired species as enzyme/substrate, receptor/agonist, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody typically binds to a single epitope and to no other epitope within the family of proteins. In some embodiments, specific binding between an antigen and an antibody will have a binding affinity of at least $10^{-6}$ M. In other embodiments, the antigen and antibody will bind with affinities of at least $10^{-7}$ M, $10^{-8}$ M to $10^{-9}$ M, $10^{-10}$ M, $10^{-11}$ M, or $10^{-12}$ M.

Various methodologies of the instant invention include a step that involves comparing a value, level, feature, characteristic, property, etc. to a "suitable control," referred to interchangeably herein as an "appropriate control," a "control sample" or a "reference." A "suitable control," "appropriate control," "control sample" or a "reference" is any control or standard familiar to one of ordinary skill in the art useful for comparison purposes. In one embodiment, a "suitable control" or "appropriate control" is a value, level, feature, characteristic, property, etc., determined in a cell, organ, or patient, e.g., a control or normal cell, organ, or patient, exhibiting, for example, normal traits. For example, the biomarkers of the present invention may be assayed for levels/ratios in a sample from an unaffected individual (UI) or a normal control individual (NC) (both terms are used interchangeably herein). In another embodiment, a "suitable control" or "appropriate control" is a value, level, feature, characteristic, property, ratio, etc. determined prior to performing a therapy (e.g., aggressive prostate cancer treatment) on a patient. In yet another embodiment, a transcription rate, mRNA level, translation rate, protein level/ratio, biological activity, cellular characteristic or property, genotype, phenotype, etc., can be determined prior to, during, or after administering a therapy into a cell, organ, or patient. In a further embodiment, a "suitable control," "appropriate control" or a "reference" is a predefined value, level, feature, characteristic, property, ratio, etc. A "suitable control" can be a profile or pattern of levels/ratios of one or more biomarkers of the present invention that correlates to aggressive prostate cancer, to which a patient sample can be compared. The patient sample can also be compared to a negative control, i.e., a profile that correlates to not having aggressive prostate cancer.

II. Detection of Aggressive Prostate Cancer Biomarkers

A. Detection by Immunoassay

In one aspect, the biomarkers of the present invention may be detected and/or measured by immunoassay Immunoassay requires biospecific capture reagents, such as antibodies, to capture the biomarkers. Many antibodies are available commercially. Antibodies also can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well-known in the art. Biospecific capture reagents useful in an immunoassay can also include lectins. The biospecific capture reagents can, in some embodiments, bind all forms of the biomarker, e.g., TIMP-1 and its post-translationally modified forms (fucosylated form). In other embodiments, the biospecific capture reagents bind the specific biomarker (e.g., fucosylated TIMP-1) and not similar forms thereof.

The present invention contemplates traditional immunoassays including, for example, sandwich immunoassays including ELISA or fluorescence-based immunoassays, immunoblots, Western Blots (WB), as well as other enzyme immunoassays. Nephelometry is an assay performed in liquid phase, in which antibodies are in solution. Binding of the antigen to the antibody results in changes in absorbance, which is measured. In a SELDI-based immunoassay, a biospecific capture reagent for the biomarker is attached to the surface of an MS probe, such as a pre-activated protein chip array. The biomarker is then specifically captured on the biochip through this reagent, and the captured biomarker is detected by mass spectrometry.

Although antibodies are useful because of their extensive characterization, any other suitable agent (e.g., a lectin, peptide, aptamer or a small organic molecule) that specifically binds a biomarker of the present invention is optionally used in place of the antibody in the above described immunoassays. For example, an aptamer that specifically binds all a biomarkers (and, in certain embodiments, its post-translationally modified forms) might be used. Aptamers are nucleic acid-based molecules that bind specific ligands. Methods for making aptamers with a particular binding specificity are known as detailed in U.S. Pat. No. 5,475,096; U.S. Pat. No. 5,670,637; U.S. Pat. No. 5,696,249; U.S. Pat. No. 5,270,163; U.S. Pat. No. 5,707,796; U.S. Pat. No. 5,595,877; U.S. Pat. No. 5,660,985; U.S. Pat. No. 5,567,588; U.S. Pat. No. 5,683,867; U.S. Pat. No. 5,637,459; and U.S. Pat. No. 6,011,020.

B. Detection by Mass Spectrometry

In another aspect, the biomarkers of the present invention may be detected by mass spectrometry, a method that employs a mass spectrometer to detect gas phase ions. Examples of mass spectrometers are time-of-flight, magnetic sector, quadrupole filter, ion trap, ion cyclotron resonance, Orbitrap, hybrids or combinations of the foregoing, and the like.

In particular embodiments, the biomarkers of the present invention are measured/detected using selected reaction monitoring (SRM) mass spectrometry techniques. Selected reaction monitoring (SRM) is a non-scanning mass spectrometry technique, performed on triple quadrupole-like instruments and in which collision-induced dissociation is used as a means to increase selectivity. In SRM experiments two mass analyzers are used as static mass filters, to monitor a particular fragment ion of a selected precursor ion. The specific pair of mass-over-charge (m/z) values associated to the precursor and fragment ions selected is referred to as a "transition" and can be written as parent m/zfragment m/z (e.g. 673.5→534.3). Unlike common MS based proteomics, no mass spectra are recorded in a SRM analysis. Instead, the detector acts as counting device for the ions matching the selected transition thereby returning an intensity distribution over time. Multiple SRM transitions can be measured within the same experiment on the chromatographic time scale by rapidly toggling between the different precursor/fragment pairs (sometimes called multiple reaction monitoring, MRM). Typically, the triple quadrupole instrument cycles through a series of transitions and records the signal of each transition as a function of the elution time. The method allows for additional selectivity by monitoring the chromatographic coelution of multiple transitions for a given analyte. The terms SRM/MRM are occasionally used also to describe experiments conducted in mass spectrometers other than triple quadrupoles (e.g. in trapping instruments) where upon fragmentation of a specific precursor ion a narrow mass range is scanned in MS2 mode, centered on a fragment ion specific to the precursor of interest or in general in experiments where fragmentation in the collision cell is used as a means to increase selectivity. In this application, the terms SRM and MRM or also SRM/MRM can be used interchangeably, since they both refer to the same mass spectrometer operating principle. As a matter of clarity, the term MRM can be used throughout the text, but the term includes both SRM and MRM, as well as any analogous technique, such as e.g. highly-selective reaction monitoring, hSRM, LC-SRM or any other SRM/MRM-like or SRM/MRM-mimicking approaches performed on any type of mass spectrometer and/or, in which the peptides are fragmented using any other fragmentation method such as e.g. CAD (collision-activated dissociation (also known as CID or collision-induced dissociation), HCD (higher energy CID), ECD (electron capture dissociation), PD (photodissociation) or ETD (electron transfer dissociation).

In another specific embodiment, the mass spectrometric method comprises matrix assisted laser desorption/ionization time-of-flight (MALDI-TOF MS or MALDI-TOF). In another embodiment, method comprises MALDI-TOF tandem mass spectrometry (MALDI-TOF MS/MS). In yet another embodiment, mass spectrometry can be combined with another appropriate method(s) as may be contemplated by one of ordinary skill in the art. For example, MALDI-TOF can be utilized with trypsin digestion and tandem mass spectrometry as described herein.

In an alternative embodiment, the mass spectrometric technique comprises surface enhanced laser desorption and ionization or "SELDI," as described, for example, in U.S. Pat. No. 6,225,047 and U.S. Pat. No. 5,719,060. Briefly, SELDI refers to a method of desorption/ionization gas phase ion spectrometry (e.g. mass spectrometry) in which an analyte (here, one or more of the biomarkers) is captured on the surface of a SELDI mass spectrometry probe. There are several versions of SELDI that may be utilized including, but not limited to, Affinity Capture Mass Spectrometry (also called Surface-Enhanced Affinity Capture (SEAC)), and Surface-Enhanced Neat Desorption (SEND) which involves the use of probes comprising energy absorbing molecules that are chemically bound to the probe surface (SEND probe). Another SELDI method is called Surface-Enhanced Photolabile Attachment and Release (SEPAR), which involves the use of probes having moieties attached to the surface that can covalently bind an analyte, and then release the analyte through breaking a photolabile bond in the moiety after exposure to light, e.g., to laser light (see, U.S. Pat. No. 5,719,060). SEPAR and other forms of SELDI are readily adapted to detecting a biomarker or biomarker panel, pursuant to the present invention.

In another mass spectrometry method, the biomarkers can be first captured on a chromatographic resin having chromatographic properties that bind the biomarkers. For example, one could capture the biomarkers on a cation exchange resin, such as CM Ceramic HyperD F resin, wash the resin, elute the biomarkers and detect by MALDI. Alternatively, this method could be preceded by fractionating the sample on an anion exchange resin before application to the cation exchange resin. In another alternative, one could fractionate on an anion exchange resin and detect by MALDI directly. In yet another method, one could capture the biomarkers on an immuno-chromatographic resin that comprises antibodies that bind the biomarkers, wash the resin to remove unbound material, elute the biomarkers from the resin and detect the eluted biomarkers by MALDI or by SELDI.

C. Detection by Electrochemicaluminescent Assay

In several embodiments, the biomarker biomarkers of the present invention may be detected by means of an electrochemicaluminescent assay developed by Meso Scale Discovery (Gaithersrburg, Md.). Electrochemiluminescence detection uses labels that emit light when electrochemically stimulated. Background signals are minimal because the stimulation mechanism (electricity) is decoupled from the signal (light). Labels are stable, non-radioactive and offer a choice of convenient coupling chemistries. They emit light at ~620 nm, eliminating problems with color quenching. See U.S. Pat. No. 7,497,997; U.S. Pat. No. 7,491,540; U.S. Pat. No. 7,288,410; U.S. Pat. No. 7,036,946; U.S. Pat. No. 7,052,861; U.S. Pat. No. 6,977,722; U.S. Pat. No. 6,919,173; U.S. Pat. No. 6,673,533; U.S. Pat. No. 6,413,783; U.S. Pat. No. 6,362,011; U.S. Pat. No. 6,319,670; U.S. Pat. No. 6,207,369; U.S. Pat. No. 6,140,045; U.S. Pat. No. 6,090,545; and U.S. Pat. No. 5,866,434. See also U.S. Patent Applications Publication No. 2009/0170121; No. 2009/006339; No. 2009/0065357; No. 2006/0172340; No. 2006/0019319; No. 2005/0142033; No. 2005/0052646; No. 2004/0022677; No. 2003/0124572; No. 2003/0113713; No. 2003/0003460; No. 2002/0137234; No. 2002/0086335; and No. 2001/0021534.

D. Other Methods for Detecting Biomarkers

The biomarkers of the present invention can be detected by other suitable methods. Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Furthermore, a sample may also be analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there. Protein biochips are biochips adapted for the capture of polypeptides. Many protein biochips are described in the art. These include, for example, protein biochips produced by Ciphergen Biosystems, Inc. (Fremont, Calif.), Invitrogen Corp. (Carlsbad, Calif.), Affymetrix, Inc. (Fremong, Calif.), Zyomyx (Hayward, Calif.), R&D Systems, Inc. (Minneapolis, Minn.), Biacore (Uppsala, Sweden) and Procognia (Berkshire, UK). Examples of such protein biochips are described in the following patents or published patent applications: U.S. Pat. No. 6,537,749; U.S. Pat. No. 6,329,209; U.S. Pat. No. 6,225,047; U.S. Pat. No. 5,242,828; PCT International Publication No. WO 00/56934; and PCT International Publication No. WO 03/048768.

III. Determination of a Patient's Aggressive Prostate Cancer Status

A. The present invention relates to the use of biomarkers to diagnose aggressive prostate cancer. More specifically, the biomarkers of the present invention can be used in diagnostic tests to determine, qualify, and/or assess aggressive prostate cancer or status, for example, to diagnose aggressive prostate cancer, in an individual, subject or patient. In particular embodiments, aggressive prostate cancer status can include determining a patient's aggressive prostate cancer status, for example, to diagnose aggressive prostate cancer, in an individual, subject or patient. More specifically, the biomarkers to be detected in diagnosing aggressive prostate cancer include sTIE-2, sVEGFR-1, fucosylated TIMP-1, fucosylated DPP-4, and FUT8. Other biomarkers known in the relevant art may be used in combination with the biomarkers described herein including, but not limited to, cathepsin-L (CTSL), periostin, microfibrillar-associated protein 4 (MFAP4), collagen XII, neprilysin, clusterin, neutrophil gelatinase associated lipocalin (NGAL), epithelial cell activating molecule (EpCAM), prostate specific antigen (PSA), membrane metallo-endopeptidase (MME) and asporin (ASPN). See, e.g., WO2012, 129408.

B. Biomarker Panels

The biomarkers of the present invention can be used in diagnostic tests, like a multiplex assay, to assess, determine, and/or qualify (used interchangeably herein) aggressive prostate cancer status in a patient. The phrase "aggressive prostate cancer status" includes any distinguishable manifestation of the condition, including not having aggressive prostate cancer. For example, aggressive prostate cancer status includes, without limitation, the presence or absence of aggressive prostate cancer in a patient, the risk of developing aggressive prostate cancer, the stage or severity of aggressive prostate cancer, the progress of aggressive prostate cancer (e.g., progress of aggressive prostate cancer over time) and the effectiveness or response to treatment of aggressive prostate cancer (e.g., clinical follow up and surveillance of aggressive prostate cancer after treatment). Based on this status, further procedures may be indicated, including additional diagnostic tests or therapeutic procedures or regimens.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

In particular embodiments, the biomarker panels of the present invention may show a statistical difference in different aggressive prostate cancer statuses of at least $p<0.05$, $p<10^{-2}$, $p<10^{-3}$, $p<10^{-4}$ or $p<10^{-5}$. Diagnostic tests that use these biomarkers may show an ROC of at least 0.6, at least about 0.7, at least about 0.8, or at least about 0.9.

The biomarkers can be differentially present in UI (NC or non-aggressive prostate cancer) and aggressive prostate cancer, and, therefore, are useful in aiding in the determination of aggressive prostate cancer status. In certain embodiments, the biomarkers are measured in a patient sample using the methods described herein and compared, for example, to predefined biomarker levels/ratios and correlated to aggressive prostate cancer status. In particular embodiments, the measurement(s) may then be compared with a relevant diagnostic amount(s), cut-off(s), or multivariate model scores that distinguish a positive aggressive prostate cancer status from a negative aggressive prostate cancer status. The diagnostic amount(s) represents a measured amount of a biomarker(s) above which or below which a patient is classified as having a particular aggressive prostate cancer status. For example, if the biomarker(s) is/are up-regulated compared to normal (e.g., no cancer or non-aggressive prostate cancer) during aggressive prostate cancer, then a measured amount(s) above the diagnostic cutoff(s) provides a diagnosis of aggressive prostate cancer. Alternatively, if the biomarker(s) is/are down-regulated during aggressive prostate cancer, then a measured amount(s) at or below the diagnostic cutoff(s) provides a diagnosis of non-aggressive prostate cancer. The opposite may hold true as well (i.e., expression of the biomarker is lower/downregulated in aggressive prostate cancer vs. no cancer or non-aggressive prostate cancer) As is well understood in the art, by adjusting the particular diagnostic cut-off(s) used in an assay, one can increase sensitivity or specificity of the diagnostic assay depending on the preference of the diagnostician. In particular embodiments, the particular diagnostic cut-off can be determined, for example, by measuring the amount of biomarkers in a statistically significant number of samples from patients with the different aggressive prostate cancer statuses, and drawing the cut-off to suit the desired levels of specificity and sensitivity.

In other embodiments, ratios of post-translationally modified biomarkers (e.g., fucosylation, glycosylation, citrullination, oxidation, methylation, phosphorylation, cysteinylation s-nitrosation, s-glutathyolation, or a combination thereof) to the corresponding unmodified biomarkers are useful in aiding in the determination of aggressive prostate cancer status. In certain embodiments, the biomarker ratios are indicative of diagnosis. In other embodiments, a biomarker ratio can be compared to another biomarker ration in the same sample or to a set of biomarker ratios from a control or reference sample. In further embodiments, the amount(s) of a post-translationally modified biomarker(s) (e.g., fucosylated) can be compared to a reference or control sample (predefined amounts correlating to aggressive prostate cancer, non-aggressive prostate cancer, no cancer, and the like).

Indeed, as the skilled artisan will appreciate there are many ways to use the measurements of two or more biomarkers in order to improve the diagnostic question under investigation. In a quite simple, but nonetheless often effective approach, a positive result is assumed if a sample is positive for at least one of the markers investigated.

Furthermore, in certain embodiments, the values measured for markers of a biomarker panel are mathematically combined and the combined value is correlated to the underlying diagnostic question. Biomarker values may be combined by any appropriate state of the art mathematical method. Well-known mathematical methods for correlating a marker combination to a disease status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will have no problem in selecting an appropriate method to evaluate a biomarker combination of the present invention. In one embodiment, the method used in a correlating a biomarker combination of the present invention, e.g. to diagnose aggressive prostate cancer, is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis. Details relating to these statistical methods are found in the following references: Ruczinski et al., 12 J. OF COMPUTATIONAL AND GRAPHICAL STATISTICS 475-511 (2003); Friedman, J. H., 84 J. OF THE AMERICAN STATISTICAL ASSOCIATION 165-75 (1989); Hastie, Trevor, Tibshirani, Robert, Friedman, Jerome, The Elements of Statistical Learning, Springer Series in Statistics (2001); Breiman, L., Friedman, J. H., Olshen, R. A., Stone, C. J. Classification and regression trees, California: Wadsworth (1984); Breiman, L., 45 MACHINE LEARNING 5-32 (2001); Pepe, M. S., The Statistical Evaluation of Medical Tests for Classification and Prediction, Oxford Statistical Science Series, 28 (2003); and Duda, R. O., Hart, P. E., Stork, D. G., Pattern Classification, Wiley Interscience, 2nd Edition (2001).

C. Determining Risk of Developing Aggressive Prostate Cancer

In a specific embodiment, the present invention provides methods for determining the risk or likelihood of having or developing aggressive prostate cancer in a patient. Biomarker percentages, ratios, amounts or patterns are characteristic of various risk states, e.g., high, medium or low. The risk of developing aggressive prostate cancer is determined by measuring the relevant biomarkers and then either submitting them to a classification algorithm or comparing them with a reference amount, i.e., a predefined level or pattern of biomarkers that is associated with the particular risk level.

D. Determining Aggressive Prostate Cancer Severity

In another embodiment, the present invention provides methods for determining the severity of aggressive prostate cancer in a patient. Each grade or stage of aggressive prostate cancer likely has a characteristic level of a biomarker or relative levels/ratios of a set of biomarkers (a pattern or ratio). The severity of aggressive prostate cancer is determined by measuring the relevant biomarkers and then either submitting them to a classification algorithm or comparing them with a reference amount, i.e., a predefined level or pattern of biomarkers that is associated with the particular stage.

E. Determining Aggressive Prostate Cancer Prognosis

In one embodiment, the present invention provides methods for determining the course of aggressive prostate cancer in a patient. Aggressive prostate cancer course refers to changes in aggressive prostate cancer status over time, including aggressive prostate cancer progression (worsening) and aggressive prostate cancer regression (improvement). Over time, the amount or relative amount (e.g., the pattern or ratio) of the biomarkers changes. For example, biomarker "X" may be increased with aggressive prostate cancer, while biomarker "Y" may be decreased with aggressive prostate cancer. Therefore, the trend of these biomarkers, either increased or decreased over time toward aggressive prostate cancer or non-aggressive prostate cancer indicates the course of the condition. Accordingly, this method involves measuring the level of one or more biomarkers in a patient at least two different time points, e.g., a first time and a second time, and comparing the change, if any. The course of aggressive prostate cancer is determined based on these comparisons.

F. Patient Management

In certain embodiments of the methods of qualifying aggressive prostate cancer status, the methods further comprise managing patient treatment based on the status. Such management includes the actions of the physician or clinician subsequent to determining aggressive prostate cancer status. For example, if a physician makes a diagnosis of aggressive prostate cancer, then a certain regime of monitoring would follow. An assessment of the course of aggressive prostate cancer using the methods of the present invention may then require a certain aggressive prostate cancer therapy regimen. Alternatively, a diagnosis of non-aggressive prostate cancer might be followed with further testing to determine a specific disease that the patient might be suffering from. Also, further tests may be called for if the diagnostic test gives an inconclusive result on aggressive prostate cancer status.

G. Determining Therapeutic Efficacy of Pharmaceutical Drug

In another embodiment, the present invention provides methods for determining the therapeutic efficacy of a pharmaceutical drug. These methods are useful in performing clinical trials of the drug, as well as monitoring the progress of a patient on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern, profile or ratio) of one or more of the biomarkers of the present invention may change toward a non-aggressive prostate cancer profile. Therefore, one can follow the course of one or more biomarkers in the patient during the course of treatment. Accordingly, this method involves measuring one or more biomarkers in a patient receiving drug therapy, and correlating the biomarker levels/ratios with the aggressive prostate cancer status of the patient (e.g., by comparison to predefined levels/ratios of the biomarkers that correspond to different aggressive prostate cancer statuses). One embodiment of this method involves determining the levels/ratios of one or more biomarkers for at least two different time points during a course of drug therapy, e.g., a first time and a second time, and comparing the change in levels/ratios of the biomarkers, if any. For example, the levels/ratios of one or more biomarkers can be measured before and after drug administration or at two different time points during drug administration. The effect of therapy is determined based on these comparisons. If a treatment is effective, then the level/ratio of one or more biomarkers will trend toward normal, while if treatment is ineffective, the level/ratio of one or more biomarkers will trend toward aggressive prostate cancer indications.

H. Generation of Classification Algorithms for Qualifying Aggressive Prostate Cancer Status In some embodiments, data that are generated using samples such as "known samples" can then be used to "train" a classification model. A "known sample" is a sample that has been pre-classified. The data that are used to form the classification model can be referred to as a "training data set." The training data set that is used to form the classification model may comprise raw data or pre-processed data. Once trained, the classification model can recognize patterns in data generated using unknown samples. The classification model can then be used to classify the unknown samples into classes. This can be useful, for example, in predicting whether or not a particular biological sample is associated with a certain biological condition (e.g., diseased versus non-diseased).

Classification models can be formed using any suitable statistical classification or learning method that attempts to segregate bodies of data into classes based on objective parameters present in the data. Classification methods may be either supervised or unsupervised. Examples of supervised and unsupervised classification processes are described in Jain, "Statistical Pattern Recognition: A Review," IEEE Transactions on Pattern Analysis and Machine Intelligence, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART), artificial neural networks such as back propagation networks, discriminant analyses (e.g., Bayesian classifier or Fischer analysis), logistic classifiers, and support vector classifiers (support vector machines).

Another supervised classification method is a recursive partitioning process. Recursive partitioning processes use recursive partitioning trees to classify data derived from unknown samples. Further details about recursive partitioning processes are provided in U.S. Patent Application No. 2002 0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application Publication No. 2002/0193950 (Gavin et al. "Method or analyzing mass spectra"), U.S. Patent Application Publication No. 2003/0004402 (Hitt et al., "Process for discriminating between biological states based on hidden patterns from biological data"), and U.S. Patent Application Publication No. 2003/0055615 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows® or Linux™ based operating system. In embodiments utilizing a mass spectrometer, the digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including R, C, C++, visual basic, etc.

The learning algorithms described above are useful both for developing classification algorithms for the biomarkers already discovered, and for finding new biomarker biomarkers. The classification algorithms, in turn, form the base for diagnostic tests by providing diagnostic values (e.g., cut-off points) for biomarkers used singly or in combination.

IV. Kits for the Detection of Aggressive Prostate Cancer Biomarkers

In another aspect, the present invention provides kits for qualifying aggressive prostate cancer status, which kits are used to detect the biomarkers described herein. In a specific embodiment, the kit is provided as an ELISA kit comprising antibodies and lectins to the biomarkers of the present invention including, but not limited to, sTIE-2, sVEGFR-1, fucosylated TIMP-1, fucosylated DPP-4, and/or FUT8, and combinations of all of the foregoing.

The ELISA kit may comprise a solid support, such as a chip, microtiter plate (e.g., a 96-well plate), bead, or resin having biomarker capture reagents attached thereon. The kit may further comprise a means for detecting the biomarkers, such as antibodies, and a secondary antibody-signal complex such as horseradish peroxidase (HRP)-conjugated goat anti-rabbit IgG antibody and tetramethyl benzidine (TMB) as a substrate for HRP. In other embodiments, the kit can comprise magnetic beads conjugated to the antibodies (or separate containers thereof for later conjugation). The kit can further comprise detection antibodies, for example, biotinylated antibodies or lectins that can be detected using, for example, streptavidin labeled fluorescent markers such as phycoerythrin. The kit can be configured to perform the assay in a singleplex or multiplex format.

In certain embodiments, a patient can be diagnosed by adding blood or blood serum from the patient to the kit and detecting the relevant biomarkers conjugated with antibodies/lectins, specifically, by a method which comprises the steps of: (i) collecting blood or blood serum from the patient; (ii) separating blood serum from the patient's blood; (iii) adding the blood serum from patient to a diagnostic kit; and, (iv) detecting the biomarkers conjugated with antibodies/lectins. In this method, the antibodies/lectins are brought into contact with the patient's blood. If the biomarkers are present in the sample, the antibodies/lectins will bind to the sample, or a portion thereof. In other kit and diagnostic embodiments, blood or blood serum need not be collected from the patient (i.e., it is already collected). Moreover, in other embodiments, the sample may comprise a tissue sample or a clinical sample.

The kit can also comprise a washing solution or instructions for making a washing solution, in which the combination of the capture reagents and the washing solution allows capture of the biomarkers on the solid support for subsequent detection by, e.g., antibodies/lectins or mass spectrometry. In a further embodiment, a kit can comprise instructions for suitable operational parameters in the form of a label or separate insert. For example, the instructions may inform a consumer about how to collect the sample, how to wash the probe or the particular biomarkers to be detected, etc. In yet another embodiment, the kit can comprise one or more containers with biomarker samples, to be used as standard(s) for calibration.

Without further elaboration, it is believed that one skilled in the art, using the preceding description, can utilize the present invention to the fullest extent. The following examples are illustrative only, and not limiting of the remainder of the disclosure in any way whatsoever.

Examples

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Validation of a Multiplex Immunoassay for Serum Angiogenic Factors as Biomarkers for Aggressive Prostate Cancer Prostate cancer is currently the most common cancer in American men. There were an estimated 240,890 new cases of prostate cancer per year. The fact that only 33,720 of them died of prostate cancers annually suggests that majority of the cancers does not progress. Thus, development of accurate prognostic markers to identify patients with aggressive prostate cancers who need to be aggressively treated is urgently needed.

A prognostic biomarker should possess a clear biological significance. Prostate cancer progression and metastasis are pathological events closely linked to angiogenesis, the formation of new blood vessels from the pre-existing ones (3), (4), (5) and (6). This neovascularization process supplies oxygen and nutrients to tumor outgrowth, and contributes to tumor progression from in situ lesions to locally invasive, and eventually to metastatic tumors. In prostate cancer, intensity of angiogenesis, measured as microvessel density (MVD), was found to be higher when compared to benign glands (4) and (5). Furthermore, angiogenesis was found to be increased in the primary tumors of patients with metastasis compared to patients with localized disease (3).

The tumor angiogenic process is controlled by pro- and anti-angiogenic factors released from tumor cells, tumor-associated inflammatory cells, and/or from the extracellular matrix. Mechanistically driven by tumor progression, these factors may be present in serum, reflecting the overall angiogenic activity of the tumors. Tumor progression and patient survival in many cancers, including malignant melanoma (7), end-stage epithelial ovarian cancer (8), and pancreatic cancer (9), have been correlated with serum angiogenic factors. As a result, serum angiogenic factors are ideal candidates as prognostic biomarkers in prostate cancer.

Assays used for the discovery of biomarkers should be robust and high-throughput, capable of analyzing a sufficiently large number of samples over a sufficiently long period of time with good precision. Poor precision not only increases the required sample size for discovery, but also hinders the true revelation of differential expression of biomarkers in the case and control populations (10). In this study, we discovered prognostic biomarkers for aggressive prostate cancer by composite profiling of serum angiogenic factors using the Bio-flex Pro™ Human Cancer Biomarker Panel 1, a 16-plea multiplex immunoassay. This multiplex approach conserved specimen, limited sample handling, increased throughput, and reduced labor costs. We evaluated the analytical performance of the panel, including limit of quantification, linearity, and precisions. After the analytical evaluation, we applied the panel to assess the potentials of the 16 angiogenic factors for identifying aggressive prostate cancer in serum.

Materials and Methods

Samples and Reagents.

The 37 serum specimens analyzed in this study were from men with prostate cancer. All men had a prostate biopsy. Blood was collected before radical prostatectomy and sera stored frozen at −70° C. before analysis. Informed consent was obtained under institutional review board approved and Health Insurance Portability and Accountability Act compliant protocols. Human pooled serum was from Sigma. Samples were assayed with the Bio-Plex Pro™ Human Cancer Biomarker Panel 1, 16-plex kit (171-AC500M) from BioRad Inc.

Procedures for Performing the Assays.

The Bio-Plex Pro™ Human Cancer Biomarker Panel 1 includes 16 magnetic bead-based assays to measure sEGFR, FGF-basic, Osteopontin, PDGF-AB/BB, Follistatin, G-CSF, PECAM-1, Prolactin, sHer-2/neu, HGF, SCF, sTIE-2, sIL-6Ra, Leptin, sVEGFR-1, and sVEGFR-2. Each kit contains standard diluent HB, sample diluent HB, assay buffer, wash buffer, detection antibody diluent, streptavidin-phycoethythrin (SA-PE), 96-well flat bottom assay plate, coupled magnetic beads (20×), detection antibody (20×), standard (in a vial), quality control high and low (in vials). The reagents in the kit were warmed at the room temperature for 30 min before use. To prepare the standard and quality control high and low, 781 and 250 µl of standard diluent HB were used to reconstitute the standard and quality controls, respectively, followed by vortex for 5 s and incubation on ice for 30 min. Meanwhile, the Tecan Evo 150 liquid handling system was used to perform 4-fold dilution of samples in sample diluent HB. Calibrators were prepared by 4-fold serial dilution of the reconstituted standard using the standard diluent.

To perform the assays, the coupled magnetic beads (20×) were vortexed for 30 s before they were diluted 20 times in the assay buffer. Since the coupled magnetic beads have internal fluorescence, they should be protected from light. Each well of the 96-well flat bottom plate was added 50 µl of the diluted magnetic beads. The plate was then washed by the Bio-Plex Pro II Wash Station using the MAGX2 function. After the wash, 50 µl of diluted sample or calibrator was added to each well. The plate was then covered with aluminum seal and incubated for 60 min at the room temperature on a horizontal orbital microplate shaker. The same setting for shaking was used throughout the analytical validation. Meanwhile, the Bio-Plex 200 system, which is used to read the fluorescence of magnetic beads for protein quantification, was turned on, warmed up, and calibrated using the Bio-Plex Calibration Kit.

After the 60-minute incubation, the plate was then washed by the Bio-Plex Pro II Wash Station using the MAGX3 function. During the wash, the detection antibody solution (1×) was prepared by diluting 145 µl of the 20× detection antibody into 2755 µl of detection Ab diluent. After the wash, 25 µl of the detection antibody solution was added to each well. The plate was then covered with aluminum seal and incubated for 30 min at the room temperature.

After the 30-min incubation, the plate was then washed the same way as before. During the wash, the SA-PE solution (1×) was prepared by diluting 60 µl of the 100× SA-PE into 5940 µl of the assay buffer. After the wash, 50 µl of the diluted SA-PE solution was added to each well. The plate was then covered with aluminum seal and incubated for 10 min at the room temperature.

The plate was then washed the same way as before. Each well of the plate was added 125 µl of the assay buffer. The plate was then put onto the shaker for 1 min before being analyzed by the Bio-Plex 200 system. The system read the beads from each well and analyzed the internal fluorescence of the beads and the external fluorescence of SA-PE. The template setup in the Bio-Plex Manager™ 6.0 system for analyzing the plate contained the information that linked the internal fluorescence of beads to analytes. The external fluorescence of SA-PE was used for protein quantification.

Precisions.

Precisions were evaluated by analyses of the quality control (QC) samples in triplicates once per day for five days, based on the Clinical Laboratory Standards Institute (CLSI) guideline EP5-A2. A total of 9 levels of QC (QC1 to QC9) were prepared. QC1, the highest QC, was made by adding 325 µl of the pooled serum (Sigma 57023, Lot#041M8729) to each standard vial, and six such vials were then combined as QC1. QC1 was then 3-fold serial diluted by the pooled serum to make QC2 to QC 7. QC8 was the neat pooled serum. QC9 was a serum specimen identified (by Bio-Rad Laboratories) with the appropriate concentrations that serve as the lowest QCs for Follistatin, G-CSF, PECAM-1, and sTIE-2. The QC sample set was aliquoted and stored in −80° C. freezer. Before analysis, they were 4-fold diluted in the sample diluent.

Linearity and Limit of Quantification (LOQ).

For evaluation of LOQ, 8 samples (L1 to L8) were prepared by 4-fold serial dilution of QC1 with the standard diluent. Aliquoted and stored in a −80° C. freezer, the LOQ samples were analyzed once per day for five days. Before analysis, they were 4-fold diluted in the standard diluent.

Data Analysis.

Calibration curves were established by fitting the expected concentrations of the 16 angiogenic factors in 8 calibrators into the 5-parameter nonlinear regression model. Observed concentrations of the 16 angiogenic factors in the calibrators, QC, linearity, and patient samples were calculated and reported in Bio-Plex Manager™ 6.0. The analytical measurement ranges of the calibration curves were determined by the recovery of the analytes, where the ratio of the observed concentrations to the expected concentrations was within 70-130%. The lower and upper limit of quantifications (LLOQ and ULOQ) of the calibration curves, which defined the analytical measurement ranges, were the lowest and highest calibrators that met the acceptability criteria. The ESD (extreme studentized deviate) method was used to determine outliers. Once outliers were identified, they were excluded from data analysis. Total, within-run, and between-run precisions were calculated based on the CLSI guideline EP5-A2. Linearity was determined by the recovery of the analytes to be within 80-100%. LOQ, defined as the lowest concentration at which the assays have a CV of 20%, was evaluated by the EP Evaluator software (David G. Rhoads Associates, Inc., PA). Mann-Whitney unpaired t-test was performed in GraphPad Prism® Version 5.04.

Results and Discussion

Multiplex immunoassays, developed either in-house or by commercial vendors, have been widely used for biomarker discovery and validation. For commercially available assays, information on analytical performance from the manufacturer is a useful reference point, but assay performance in the hands of customers may be different. Variations in the procedures, such as incubation times and washing conditions, affect reproducibility of the assays. The materials used by the manufacturer to establish the analytical performance may have different matrices than specimens the customers intend to use. Analytical performance (e.g., precision and accuracy) of these assays affects not only the number of samples that should be used in biomarker discovery and validation, but also the significance of observed differences in expression of biomarkers in the studied populations. Because of these considerations, we evaluated the analytical performance of Bio-Plex Pro™ Human Cancer Biomarker Panel 1 over 5 days in serum. We established standard operating procedures (SOPs) and strictly followed them to achieve consistent reproducibility. After the analytical evaluation, we applied the panel to profile serum angiogenic factors in prostate cancer patients to discover prognostic biomarkers for aggressive prostate cancer.

BioRad Quality Controls.

BioRad has established the expected ranges for their low and high quality controls (QC) that come with the kits. The observed values of the low and high controls for all the analytes fell into the expected control ranges, except in a few cases for sVEGFR-1, the soluble form of the Vascular Endothelial Growth Factor Receptor-1 (Table 3). On days 2 and 3, the observed values for the low controls were 562.3 and 559.6 pg/ml, respectively, which fell outside the expected range of 232-541 pg/ml. On day 5, the observed value for the high control 7951.5 pg/ml fell outside the expected range of 3087-7203 pg/ml. In the case where a control supplied with the assay kit falls outside of the expected range, it is up to the user to determine final acceptability criteria for the analyte. We determined that the QCs for sVEGFR-1 were within the ranges we established (425-607 pg/ml for the low control and 3375-9337 pg/ml for the high control) using Mean±2 standard deviation (SD).

Stability of Calibration Curves.

Stability of the calibration curves was evaluated by the total precision of the observed concentrations for calibrators over 5 days (Table 4).

Calibrators S7 and S8 had the observed concentrations below the LOQs of the assays, and therefore, were excluded from the stability analyses. For all the assays, except for FGF-basic (basic Fibroblast Growth Factor), all the other 6 calibrators (S1 to S6) were included in the evaluation. FGF-basic had only 4 calibrators (S3 to S6) included, since the recovery of calibrators S1 and S2 was outside the recovery range of 70-130%. The total precisions for all the calibrators evaluated were less than 10%, indicating good stability of the calibration curves.

Precisions.

Although 9 levels of QCs were prepared and analyzed for each analyte, precisions were only reported for 3 levels in Table 1, because not all the levels of QCs had the concentrations relevant to those of sera. For example, the 9 levels of QCs for G-CSF (Granulocyte Colony-Stimulating Factor) ranged from 71.4 to 8871.6 pg/ml; the range of G-CSF in human sera, however, was less than 200 pg/ml. As a result, QCS, QC6, and QC9 of 195.2, 121.8, and 76.5 pg/ml G-CSF, respectively, were selected for evaluation of precisions for G-CSF. Within-run (n=3), between-run (n=5), and total precisions (n=15) at 3 QC levels for all 16 analytes were summarized in Table 1. Optimized multiplex assays for research purpose should have total precisions less than 20% (11). All the analytes in this panel, except Follistatin, met this requirement. Follistatin, at the level of 198.1 pg/ml, had a total precision of 22.9%. For clinical use, total precisions should be less than 10%. Eleven out of 16 assays met the criterion of total precisions less than 10%. For Follistatin, G-CSF, sTIE-2, and sVEGFR-1, the lowest level of QC had a total precision of 22.9%, 15.1%, 12.9%, and 19.5%, respectively. For Osteopontin, the highest level of QC had a total precision of 11.8%. Evidenced by our 5-day study, the majority of assays in this 16-plex panel showed good reproducibility in serum.

TABLE 1

Within-run (n = 3), between-run (n = 5), and total precisions (n = 15) at 3 QC levels for all 16 assays in the Bio-Plex Pro ™ Human Cancer Biomarker Panel 1.

| | Mean (pg/ml) | Within-run precision (% CV) | Between-run precision (% CV) | Total precision (% CV) |
|---|---|---|---|---|
| sEGFR | 79,914.2 | 5.3 | 5.1 | 6.0 |
| | 43,910.1 | 5.4 | 7.4 | 8.1 |
| | 28,622.5 | 6.1 | 5.5 | 6.5 |
| FGF-basic | 445.8 | 3.1 | 4.9 | 5.2 |
| | 226.9 | 5.9 | 5.4 | 6.4 |
| | 114.7 | 5.4 | 7.4 | 8.0 |
| Follistatin | 1018.0 | 4.6 | 6.4 | 6.9 |
| | 580.8 | 4.8 | 6.3 | 6.9 |
| | 198.1 | 14.5 | 21.3 | 22.9 |
| G-CSF | 195.2 | 6.5 | 8.0 | 8.9 |
| | 121.8 | 6.0 | 9.3 | 9.9 |
| | 76.5 | 4.8 | 14.8 | 15.1 |

TABLE 1-continued

Within-run (n = 3), between-run (n = 5), and total precisions (n = 15) at 3 QC levels for all 16 assays in the Bio-Plex Pro™ Human Cancer Biomarker Panel 1.

|  | Mean (pg/ml) | Within-run precision (% CV) | Between-run precision (% CV) | Total precision (% CV) |
|---|---|---|---|---|
| sHEr-2/neu | 32,597.4 | 6.9 | 6.1 | 7.3 |
|  | 15,617.1 | 6.0 | 6.9 | 7.7 |
|  | 8401.1 | 5.9 | 6.4 | 7.2 |
| HGF | 6113.0 | 3.9 | 3.8 | 4.4 |
|  | 1461.3 | 3.8 | 5.8 | 6.2 |
|  | 822.8 | 3.2 | 9.5 | 9.7 |
| sIL-6Ra | 29,326.0 | 4.6 | 6.4 | 6.9 |
|  | 22,480.6 | 5.7 | 6.2 | 7.0 |
|  | 18,928.2 | 7.3 | 9.2 | 10.1 |
| Leptin | 48,749.7 | 6.0 | 9.5 | 10.1 |
|  | 9347.4 | 3.6 | 7.5 | 7.8 |
|  | 7528.4 | 4.6 | 7.3 | 7.8 |
| Osteopontin | 174,401.2 | 9.5 | 10.5 | 11.8 |
|  | 80,906.8 | 3.9 | 7.8 | 8.1 |
|  | 29,199.7 | 4.0 | 8.4 | 8.7 |
| PDGF-AB/BB | 16,406.1 | 6.2 | 9.5 | 10.1 |
|  | 6722.5 | 4.0 | 5.3 | 5.7 |
|  | 1999.9 | 5.3 | 5.0 | 5.8 |
| PECAM-1 | 33,682.2 | 3.3 | 3.5 | 4.0 |
|  | 12,710.6 | 2.9 | 4.3 | 4.6 |
|  | 6154.4 | 4.6 | 5.5 | 6.1 |
| Prolactin | 18,389.1 | 2.9 | 5.4 | 5.6 |
|  | 10,170.4 | 5.5 | 4.4 | 5.4 |
|  | 6550.0 | 5.3 | 4.4 | 5.4 |
| SCF | 900.3 | 2.9 | 8.1 | 8.3 |
|  | 469.7 | 3.3 | 6.1 | 6.4 |
|  | 245.3 | 3.5 | 3.5 | 4.1 |
| sTIE-2 | 59,457.9 | 3.4 | 4.6 | 5.0 |
|  | 15,308.3 | 3.6 | 6.0 | 6.4 |
|  | 6542.7 | 2.7 | 12.9 | 12.9 |
| sVEGFR-1 | 741.2 | 3.2 | 6.7 | 6.9 |
|  | 353.6 | 7.1 | 8.0 | 9.0 |
|  | 147.8 | 12.2 | 18.2 | 19.5 |
| sVEGFR-2 | 18,585.7 | 3.0 | 3.9 | 4.3 |
|  | 11,152.4 | 3.5 | 3.7 | 4.2 |
|  | 8151.5 | 5.7 | 6.3 | 7.1 |

Limits of Quantitation.

The LOQs for the 16 assays in the BioRad Human Cancer Biomarker Panel 1, calculated as the lowest concentrations at which the assays demonstrated a total precision of 20%, were summarized in Table 2. For Leptin, PECAM-1 (Platelet/Endothelial Cell Adhesion Molecule-1), and SCF (Stem Cell Factor), the LOQs were not numerical numbers, but ranges, because the assays had total precisions less than 20% for all the concentrations evaluated, even for the lowest concentration (total precisions were 14.3%, 11.0%, and 12.1%, respectively). Therefore, the LOQs for Leptin, PECAM-1, and SCF were below the lowest concentrations evaluated, 31.5, 204.9, and 10.9 pg/ml, respectively.

TABLE 2

LOQ and linearity of all the 16 assays in the Bio-Plex Pro™ Human Cancer Biomarker Panel 1.

|  | LOQ (pg/ml) | Linearity (pg/ml)[a] | Extended linearity[b] |
|---|---|---|---|
| sEGFR | Less than 265.0 | 28,622.5-46,014.5 | 265.0-46,014.5 |
| FGF-basic | Less than 31.2 | 120.9-28,665.1 | 31.2-28,665.1 |
| Follistatin | 26.1 | 352.2-43,590.0 | 26.1-43,590.0 |
| G-CSF | 55.8 | 81.3-8892.7 | 55.8-8892.7 |
| sHEr-2/neu | 18.6 | 8401.1-32,597.4 | 18.6-32,597.4 |
| HGF | 28.0 | 822.8-53,654.5 | 28.0-53,654.5 |
| sIL-6Ra | 13.5 | 18,928.2-29,326.0 | 13.5-29,326.0 |
| Leptin | Less than 31.5 | 7528.4-119,075.8 | 31.5-119,075.8 |
| Osteopontin | 682.8 | 29,199.7-174,401.2 | 682.8-174,401.2 |
| PDGF-AB/BB | 41.9 | 1999.9-42,765.8 | 41.9-42,765.8 |
| PECAM-1 | Less than 204.9 | 9264.5-207,700.2 | 204.9-207,700.2 |
| Prolactin | 499.7 | 6550.0-293,875.7 | 499.7-293,875.7 |
| SCF | Less than 10.9 | 245.3-56,324.1 | 10.9-56,324.1 |
| sTIE-2 | 356.0 | 10,036.9-155,632.3 | 356.0-155,632.3 |
| sVEGFR-1 | 154.5 | 147.7-15,591.4 | 154.5-15,591.4 |
| sVEGFR-2 | 121.6 | 8151.5-135,750.2 | 121.6-135,750.2 |

[a]Linearity was established using the QC samples.
[b]Extended linearity was established by extending the linearity using the LOQ samples.

Linearity.

Using the QC samples, we established that all the assays were linear in serum. The linearity ranges for these assays were summarized in Table 2. All the assays, except sEGFR, the soluble form of the epidermal growth factor receptor, were linear from QC8 (the lowest concentration) to QC1 (the highest concentration). sEGFR is linear up to QC3, because QC2 had a recovery of 128.0%, outside the recovery acceptability of 80-120% (Table 5). The advantage of using the QC samples for evaluation of linearity was that all the QC samples had the same matrix as serum, excluding the possibility of matrix effect to be the culprit of non-linearity.

For proper evaluation of the assays' lower end of the linearity, QC8 may not be suitable. QC8, a serum sample without removing any of the endogenous analytes, contains analytes of interest whose concentrations may be above the lower ends of linearity. This problem can be solved by using the LOQ samples, which were prepared by proportional mixing QC1 and the standard diluent that contains no analytes of interest. Using the LOQ samples, we established that all the assays, except sVEGFR-1, were linear down to the concentrations close to or at the levels of the LOQs (Table 2). For sVEGFR-1, the assay was determined using the QC samples to be linear down to the 147.7 pg/ml, close to the LOQ level.

Matrix Effects.

QC1 was diluted in the sample diluent prior to analysis; whereas the LOQ samples, prepared from QC1, were diluted in standard diluent. In order to evaluate matrix difference in diluents, we determined the recovery of the LOQ samples, calculated as the ratio of measured concentrations to calculated concentrations (Table 6). The calculated concentrations for LOQ samples were derived from the measured concentrations of QC1. If the recovery was close to 100%, it indicated that assays were not affected by the matrix difference in diluents. Seven assays, Follistatin, HGF (hepatocyte growth factor), sIL-6Ra, the soluble form of Interleukin-6 Receptor a, PDGF-AB/BB (platelet-derived growth factor-AB/BB), PECAM-1, Prolactin, and SCF, were not affected by matrix difference in diluents; whereas the other nine assays were. Specifically, the recovery of L2 to L9 for these analytes was all higher than the ideal recovery of 100%. This indicated that Bio-Plex sample diluent, which was used for dilution of QC1, helped eliminate false positive interference in human serum. Bio-Rad recommended diluting serum and plasma samples 4-fold in Bio-Plex sample diluent and reconstituting/diluting the supplied calibrators (standards) in Bio-Plex standard diluent. When prepared as such, both samples and standards have a matched serum content of 25% in the assay.

Expression of the 16 Serum Angiogenic Factors in Prostate Cancer Patients.

Panel 1 includes 16 serum angiogenic factors associated with prostate cancer in three different ways. First, they are soluble receptors of the angiogenic factors that have well-established roles in prostate cancer, such as VEGF, TIE-2, IL-6 and Her-2/neu. VEGF and receptors and angiopoietins and their receptor TIE-2 are the most important systems involved in angiogenesis. VEGF expression in prostate cancer has been shown to correlate with tumor stage, grade and clinical outcome (12), (13), (14) and (15) Inhibition of angiopeiotein-2 has been shown to impede angiogenesis and growth of LuCap23.1 prostate cancer xenografts, indicating the role of angiopeotien-2 in prostate cancer progression and metastasis (16). IL-6 was associated with advanced stage and metastasis-related morbidity in prostate cancer (17). Serum IL-6 levels in patients with metastatic disease were higher than those in patients with localized disease and were predictors of biochemical recurrence in localized diseases (18). In prostate cancer, Her2/neu was over-expressed in 25-40% and 60-80% of cases of localized and metastatic cancer, respectively (19), (20), (21) and (22). Serum levels of Her-2/neu were used to predict biochemical recurrence-free survival in prostate cancer patients about to undergo endocrine therapy (23).

Although Panel 1 measures the soluble receptors of these angiogenic factors, evidence exists that the levels of soluble receptor correlate with clinical parameters. One example is the soluble ErbB1 receptor (sErbB1), which has been shown to correlate with tumor stage in epithelial ovarian cancer (24). Another example is the soluble urokinase plasminogen activator receptor (suPAR) which can predict survival of patients with colorectal cancer (25). Indeed, the detection of soluble receptor IL-6 improved a preoperative nomogram for predicting biochemical progression in patients with clinical localized prostate cancer (26). Second, they have well-established roles in prostate cancer progression, such as FGF-basic and HGF. FGF-basic was a potent angiogenic factor and promoter of tumor angiogenesis (15) and (27). As demonstrated in human prostate cancer cell lines and TRAMP mouse model, FGF-basic played important roles in prostate cancer progression (28) and (29). Hepatocyte growth factor (HGF) was implicated in the progression and metastasis of prostate cancer through its receptor c-Met (30). Men with metastatic prostate cancer have significantly higher serum level of HGF than men with localized prostate cancer and those without prostate cancer (31). Lastly, they have less well-characterized roles in prostate cancer, but well-established roles in tumor angiogenesis, such as PDGF, and Osteopontin. PDGF-A and PDGF receptors were expressed by epithelial and stromal cells in prostatic intra-epithelial neoplasia (32). In addition, the human prostate cancer cell lines DU145 and PC-3 express PDGF (33), and PDGF stimulated human prostate stromal cell proliferation in vitro (34). Thus, PDGF may promote reactive stroma in the prostate. The possible role of osteopontin in prostate cancer progression was exemplified through inhibition of the growth of human prostate cancer cell lines LNCaP and C4-2 in vitro by antibodies to human osteopontin (35).

Because of the implications of the angiogenic factors in prostate cancer, the Bio-Rad Human Cancer Biomarker Panel 1 was applied to analyze 37 serum samples from prostate cancer patients. Overall, the measurements were within reportable assay limits, confirming that the sample dilution factor of 4 was appropriate for all the analytes in serum. Expression of 16 markers in patients with GS=6, GS=7, and GS 8-10 is shown in FIG. 1. Because it had been shown that Gleason score less than 7, Gleason score 7, and Gleason score greater than 7 correlated significantly with the outcome of prostate cancer after radical prostatectomy (36) and (37), in our study, we correlated the biomarker concentrations with Gleason scores.

Median analysis of the expression of these markers in relation to the GS indicated that 7 markers (sHEr-2/neu, HGF, sIL-6-Ra, PECAM-1, SCF, sTIE-2, and sVEGFR-2) showed increasing expression with increasing Gleason score. However, none of the trends was statistically significant except for sTIE-2. In patients with GS 8-10, the levels of sTIE-2 were significantly increased compared to the patients with GS=6 or GS=7 or the combination of GS=6 and GS=7 ($p<0.05$). The levels of sTIE-2 between patients with GS=6 (n=18) and GS=7 (n=13) were not significantly different, although the median for GS=7 group was higher (7183 pg/ml vs. 6761 pg/ml). Opposite to sTIE-2, the levels of sVEGFR-1 were decreased in GS8-10 group, although the difference was not statistically significantly. sTIE-2, a soluble form of the angiopoietin receptor TIE-2, is generated by a shedding mechanism in which the transmembrane receptor is proteolytically cleaved leading to the release of the extracellular domain. sVEGFR-1, the soluble form of VEGFR-1, is generated by a different mechanism, the alternative splicing of a single gene. sVEGFR-1 levels were suppressed and sTie-2 receptor levels were raised in colorectal cancer patients (38), consistent with our result. This indicates that by combining these 2 biomarkers sTIE-2 and sVEGFR-1 (e.g., in a multiplex biomarker panel), we may be able to identify patients with GS 8-10 with better sensitivity and specificity than using sTIE-2 alone.

Conclusions

We evaluated the analytical performance of the Bio-Plex Pro™ Human Cancer Biomarker Panel 1, a 16-plex multiplex immunoassay, in serum for composite profiling of angiogenic factors. Our 5-day evaluation indicated good reproducibility (total precisions over 5 independent plates in 5 days of less than 20%), adequate sensitivity in serum for reliable detection of these 16 angiogenic factors in serum (LOQs of majority of the assays less than 100 pg/ml), and wide dynamic ranges (linearity of the majority of assays spanning 3 logs in concentrations) that allow for a single four-fold dilution factor for serum samples. The analytical performance was optimal for biomarker discovery of serum angiogenic factors in prostate cancer patients. Applying the panel to sera from prostate cancer patients with Gleason scores of 6, 7, 8-10, we demonstrated that levels of sTIE-2, a soluble form of the angiopoietin receptor TIE-2, were elevated in patients with Gleason scores of 8-10. Future studies will be necessary to determine whether sTIE-2 could be used as a prognostic biomarker for identifying aggressive prostate cancer.

References

1. Cancer Facts & FIGS. 2009. Atlanta: American Cancer Society: American Cancer Society; 2009.
2. Cooperberg M R, Lubeck D P, Meng M V, Mehta S S, Carroll P R. The changing face of low-risk prostate cancer: trends in clinical presentation and primary management. J Clin Oncol 2004; 22(11):2141-9.
3. Weidner N, Carroll P R, Flax J, Blumenfeld W, Folkman J. Tumor angiogenesis correlates withmetastasis in invasive prostate carcinoma. AmJ Pathol 1993; 143(2):401-9.

4. Strohmeyer D, Rossing C, Strauss F, Bauerfeind A, Kaufmann O, Loening S. Tumor angiogenesis is associated with progression after radical prostatectomy in pT2/pT3 prostate cancer. Prostate 2000; 42(1):26-33.
5. Vartanian R K, Weidner N. Endothelial cell proliferation in prostatic carcinoma and prostatic hyperplasia: correlation with Gleason's score, microvessel density, and epithelial cell proliferation. Lab Invest 1995; 73(6):844-50.
6. Huss W J, Hanrahan C F, Barrios R J, Simons J W, Greenberg N M. Angiogenesis and prostate cancer: identification of a molecular progression switch. Cancer Res 2001; 61(6):2736-43.
7. Ugurel S, Rappl G, Tilgen W, Reinhold U. Increased serum concentration of angiogenic factors in malignant melanoma patients correlates with tumor progression and survival. J Clin Oncol 2001; 19(2):577-83.
8. Secord A A, Darcy K M, Hutson A, et al. Co-expression of angiogenic markers and associations with prognosis in advanced epithelial ovarian cancer: a Gynecologic Oncology Group study. Gynecol Oncol 2007; 106(1):221-32.
9. Salgia R. Prognostic significance of angiogenesis and angiogenic growth factors in nonsmall cell lung cancer. Cancer 2011; 117(17):3889-99.
10. Zhang Z, Chan D W. The road from discovery to clinical diagnostics: lessons learned from the first FDA-cleared in vitro diagnostic multivariate index assay of proteomic biomarkers. Cancer Epidemiol Biomarkers Prev 2010; 19(12):2995-9.
11. Ellington A A, Kullo I J, Bailey K R, Klee G G. Antibody-based protein multiplex platforms: technical and operational challenges. Clin Chem 2010; 56(2):186-93.
12. Borre M, Nerstrom B, Overgaard J. Association between immunohistochemical expression of vascular endothelial growth factor (VEGF), VEGF-expressing neuroendocrine-differentiated tumor cells, and outcome in prostate cancer patients subjected to watchful waiting. Clin Cancer Res 2000; 6(5):1882-90.
13. Kuniyasu H, Troncoso P, Johnston D, et al. Relative expression of type IV collagenase, E-cadherin, and vascular endothelial growth factor/vascular permeability factor in prostatectomy specimens distinguishes organ-confined from pathologically advanced prostate cancers. Clin Cancer Res 2000; 6(6):2295-308.
14. Strohmeyer D, Rossing C, Bauerfeind A, et al. Vascular endothelial growth factor and its correlation with angiogenesis and p53 expression in prostate cancer. Prostate 2000; 45(3):216-24.
15. Doll J A, Reiher F K, Crawford S E, Pins M R, Campbell S C, Bouck N P. Thrombospondin-1, vascular endothelial growth factor and fibroblast growth factor-2 are key functional regulators of angiogenesis in the prostate. Prostate 2001; 49(4):293-305.
16. Morrissey C, Dowell A, Koreckij T D, et al Inhibition of angiopoietin-2 in LuCaP 23.1 prostate cancer tumors decreases tumor growth and viability. Prostate 2010; 70(16):1799-808.
17. Adler H L, McCurdy M A, Kattan M W, Timme T L, Scardino P T, Thompson T C. Elevated levels of circulating interleukin-6 and transforming growth factor-beta1 in patients with metastatic prostatic carcinoma. J Urol 1999; 161(1):182-7.
18. Michalaki V, Syrigos K, Charles P, Waxman J. Serum levels of IL-6 and TNF-alpha correlate with clinicopathological features and patient survival in patients with prostate cancer. Br J Cancer 2004; 90(12):2312-6.
19. Signoretti S, Montironi R, Manola J, et al. Her-2-neu expression and progression toward androgen independence in human prostate cancer. J Natl Cancer Inst 2000; 92(23):1918-25.
20. Osman I, Scher H I, Drobnjak M, et al. HER-2/neu (p185neu) protein expression in the natural or treated history of prostate cancer. Clin Cancer Res 2001; 7(9): 2643-7.
21. Shi Y, Brands F H, Chatterjee S, et al. Her-2/neu expression in prostate cancer: high level of expression associated with exposure to hormone therapy and androgen independent disease. J Urol 2001; 166(4):1514-9.
22. Morris M J, Reuter V E, Kelly W K, et al. HER-2 profiling and targeting in prostate carcinoma. Cancer 2002; 94(4):980-6.
23. Okegawa T, Kinjo M, Nutahara K, Higashihara E. Pretreatment serum level of HER2/nue as a prognostic factor in metastatic prostate cancer patients about to undergo endocrine therapy. Int J Urol 2006; 13(9):1197-201.
24. Baron A T, Cora E M, Lafky J M, et al. Soluble epidermal growth factor receptor (sEGFR/sErbB1) as a potential risk, screening, and diagnostic serum biomarker of epithelial ovarian cancer. Cancer Epidemiol Biomarkers Prev 2003; 12(2):103-13.
25. Seetoo D Q, Crowe P J, Russell P J, Yang J L. Quantitative expression of protein markers of plasminogen activation system in prognosis of colorectal cancer. J Surg Oncol 2003; 82(3):184-93.
26. Kattan M W, Shariat S F, Andrews B, et al. The addition of interleukin-6 soluble receptor and transforming growth factor beta1 improves a preoperative nomogram for predicting biochemical progression in patients with clinically localized prostate cancer. J Clin Oncol 2003; 21(19): 3573-9.
27. van Moorselaar R J, Voest E E. Angiogenesis in prostate cancer: its role in disease progression and possible therapeutic approaches. Mol Cell Endocrinol 2002; 197(1-2): 239-50.
28. Nakamoto T, Chang C S, Li A K, Chodak G W. Basic fibroblast growth factor in human prostate cancer cells. Cancer Res 1992; 52(3):571-7.
29. Huss W J, Barrios R J, Foster B A, Greenberg N M. Differential expression of specific FGF ligand and receptor isoforms during angiogenesis associated with prostate cancer progression. Prostate 2003; 54(1):8-16.
30. Humphrey P A, Zhu X, Zarnegar R, et al. Hepatocyte growth factor and its receptor (c-MET) in prostatic carcinoma. Am J Pathol 1995; 147(2):386-96.
31. Naughton M, Picus J, Zhu X, Catalona W J, Vollmer R T, Humphrey P A. Scatter factor-hepatocyte growth factor elevation in the serum of patients with prostate cancer. J Urol 2001; 165(4):1325-8.
32. Fudge K, Bostwick D G, Stearns M E. Platelet-derived growth factor A and B chains and the alpha and beta receptors in prostatic intraepithelial neoplasia. Prostate 1996; 29(5):282-6.
33. Sitaras N M, Sariban E, Bravo M, Pantazis P, Antoniades H N. Constitutive production of platelet-derived growth factor-like proteins by human prostate carcinoma cell lines. Cancer Res 1988; 48(7):1930-5.
34. Vlahos C J, Kriauciunas T D, Gleason P E, et al. Platelet-derived growth factor induces proliferation of hyperplastic human prostatic stromal cells. J Cell Biochem 1993; 52(4):404-13.
35. Rittling S R, Chambers A F. Role of osteopontin in tumour progression. Br J Cancer 2004; 90(10):1877-81.
36. Amin A, Partin A, Epstein H. Gleason score 7 prostate cancer on needle biopsy: relation of primary pattern 3 or 4 to pathological stage and progression after radical prostatectomy. J Urol 2011; 186(4):1286-90.
37. TsivianM, Sun L, Mouraviev V, et al. Changes in Gleason score grading and their effect in predicting outcome after radical prostatectomy. Urology 2009; 74(5): 1090-3.
38. Chin K F, Greenman J, Reusch P, Gardiner E, Marme D, Monson J. Changes in serum soluble VEGFR-1 and Tie-2 receptors in colorectal cancer patients following surgical resections. Anticancer Res 2004; 24(4):2353-7.

TABLE 3

|  | Day 1 | Day 2 | Day 3 | Day 4 | Day 5 | Mean (pg/mL) | SD | % CV |
|---|---|---|---|---|---|---|---|---|
| sEGFR | 857.5 | 957.7 | 906.2 | 858.7 | 953.8 | 906.8 | 48.9 | 5.4 |
| BR QC L | 15008.2 | 16060.5 | 15578.9 | 16810.5 | 16657.1 | 16023.0 | 750.1 | 4.7 |
| BR QC H |  |  |  |  |  |  |  |  |
| FGF-basic (44) | 136.2 | 141.0 | 141.8 | 139.1 | 157.8 | 143.2 | 8.5 | 5.9 |
| BR QC L | 1322.6 | 1390.4 | 1254.3 | 1364.0 | 1364.1 | 1339.1 | 53.2 | 4.0 |
| BR QC H |  |  |  |  |  |  |  |  |
| Follistatin (26) | 345.4 | 394.8 | 364.3 | 325.8 | 375.9 | 361.2 | 26.7 | 7.4 |
| BR QC L | 7362.9 | 5810.4 | 6509.1 | 7164.6 | 7153.4 | 6800.1 | 640.1 | 9.4 |
| BR QC H |  |  |  |  |  |  |  |  |
| G-CSF (57) | 247.7 | 279.1 | 288.6 | 269.7 | 293.1 | 275.7 | 18.0 | 6.5 |
| BR QC L | 3563.2 | 2964.9 | 3105.4 | 3894.2 | 3636.0 | 3432.7 | 386.4 | 11.3 |
| BR QC H |  |  |  |  |  |  |  |  |
| sHEr-2/neu (12) | 241.3 | 280.6 | 257.0 | 258.6 | 278.3 | 263.1 | 16.4 | 6.2 |
| BR QC L | 3588.4 | 3690.8 | 3336.1 | 3977.3 | 3572.5 | 3633.0 | 232.2 | 6.4 |
| BR QC H |  |  |  |  |  |  |  |  |
| HGF (62) | 683.2 | 742.8 | 718.6 | 678.7 | 830.2 | 730.7 | 61.5 | 8.4 |
| BR QC L | 11186.2 | 8967.6 | 9875.2 | 12860.8 | 10708.3 | 10719.6 | 1465.0 | 13.7 |
| BR QC H |  |  |  |  |  |  |  |  |
| sIL-6Ra (19) | 58.8 | 70.5 | 62.7 | 57.8 | 66.7 | 63.3 | 5.3 | 8.4 |
| BR QC L | 841.1 | 931.0 | 846.2 | 903.0 | 1046.7 | 913.6 | 83.5 | 9.1 |
| BR QC H |  |  |  |  |  |  |  |  |
| Leptin (78) | 486.6 | 546.3 | 491.0 | 342.2 | 597.9 | 492.8 | 95.7 | 19.4 |
| BR QC L | 10187.8 | 8448.1 | 8847.9 | 8231.4 | 10592.4 | 9261.5 | 1063.4 | 11.5 |
| BR QC H |  |  |  |  |  |  |  |  |
| Osteopontin (77) | 1050.5 | 1149.1 | 943.3 | 1163.1 | 1328.1 | 1126.8 | 143.0 | 12.7 |
| BR QC L | 17674.0 | 16003.9 | 15964.5 | 21318.4 | 18434.8 | 17879.1 | 2200.1 | 12.3 |
| BR QC H |  |  |  |  |  |  |  |  |
| PDGF-AB/BB (47) | 217.0 | 254.1 | 232.9 | 217.0 | 232.2 | 230.6 | 15.2 | 6.6 |
| BR QC L | 5202.9 | 4193.5 | 4446.6 | 5418.9 | 4654.1 | 4783.2 | 514.3 | 10.8 |
| BR QC H |  |  |  |  |  |  |  |  |
| PECAM-1 (46) | 1880.0 | 2016.2 | 1775.0 | 1794.5 | 2084.1 | 1910.0 | 136.1 | 7.1 |
| BR QC L | 24390.9 | 21877.2 | 23542.2 | 26729.7 | 25722.9 | 24452.6 | 1888.4 | 7.7 |
| BR QC H |  |  |  |  |  |  |  |  |
| Prolactin (52) | 1198.0 | 1309.3 | 1248.8 | 1433.0 | 1279.0 | 1293.6 | 88.1 | 6.8 |
| BR QC L | 25736.5 | 24294.2 | 31486.3 | 32234.6 | 32160.8 | 29182.5 | 3849.2 | 13.2 |
| BR QC H |  |  |  |  |  |  |  |  |
| SCF (65) | 203.9 | 215.6 | 202.7 | 191.4 | 220.0 | 206.7 | 11.4 | 5.5 |
| BR QC L | 5216.9 | 6175.6 | 5401.5 | 6507.0 | 5760.0 | 5812.2 | 534.0 | 9.2 |
| BR QC H |  |  |  |  |  |  |  |  |
| sTIE-2 (64) | 1127.7 | 1321.2 | 1295.8 | 1173.6 | 1322.4 | 1248.1 | 91.1 | 7.3 |
| BR QC L | 38265.7 | 35187.3 | 35190.2 | 40178.0 | 36417.7 | 37047.8 | 2155.8 | 5.8 |
| BR QC H |  |  |  |  |  |  |  |  |
| sVEGFR-1 (76) | 492.0 | 562.3* | 559.6* | 456.3 | 508.9 | 485.7 | 26.9 | 5.5 |
| BR QC L | 7175.3 | 3988.1 | 6160.4 | 7951.5* | 6506.2 | 5957.6 | 1378.9 | 23.1 |
| BR QC H |  |  |  |  |  |  |  |  |
| sVEGFR-2 (45) | 1822.5 | 2157.3 | 1945.6 | 1938.9 | 2153.0 | 2003.5 | 146.9 | 7.3 |
| BR QC L | 39771.2 | 39023.1 | 35202.1 | 43459.4 | 38782.1 | 39247.6 | 2943.1 | 7.5 |
| BR QC H |  |  |  |  |  |  |  |  |

*out of the expected control ranges defined by BioRad.

TABLE 4

|  | Day 1 | Day 2 | Day 3 | Day 4 | Day 5 | Day 6 | Mean | SD | % CV |
|---|---|---|---|---|---|---|---|---|---|
| sEGFR (15) |  |  |  |  |  |  |  |  |  |
| S1 | 157164.1 | 153813.8 | 151874.5 | 133978.8 | 153905.8 | 148063.3 | 149800.0 | 8304.5 | 5.5 |
| S2 | 37886.0 | Excluded | 38450.1 | 41582.5 | 38175.0 | 38830.2 | 38984.7 | 1493.4 | 3.8 |
| S3 | 9529.9 | 9508.6 | 9455.0 | 9475.5 | 9495.7 | 9481.9 | 9491.1 | 26.3 | 0.3 |
| S4 | 2415.4 | 2415.9 | 2448.5 | 2325.1 | 2417.1 | 2395.5 | 2402.9 | 41.7 | 1.7 |
| S5 | 581.9 | 581.6 | 574.9 | 607.5 | 590.1 | 596.8 | 588.8 | 11.9 | 2.0 |
| S6 | 153.7 | 155.7 | 150.9 | 163.9 | 145.5 | 147.7 | 152.9 | 6.6 | 4.3 |

TABLE 4-continued

|  | Day 1 | Day 2 | Day 3 | Day 4 | Day 5 | Day 6 | Mean | SD | % CV |
|---|---|---|---|---|---|---|---|---|---|
| S7 | 37.0 | 35.1 | 42.1 | 20.1 | 43.6 | 38.9 | 36.1 | 8.5 | 23.4 |
| S8 | 9.0 | 9.9 | 6.6 | 25.2 | 6.4 | 8.4 | 10.9 | 7.1 | 65.2 |
| FGF-basic (44) | | | | | | | | | |
| S3 | 1060.1 | 1139.1 | 1064.5 | 1086.5 | 1043.4 | 1049.5 | 1073.8 | 35.2 | 3.3 |
| S4 | 282.9 | 281.3 | 287.1 | 273.7 | 282.6 | 285.6 | 282.2 | 4.7 | 1.7 |
| S5 | 74.1 | 71.2 | 73.2 | 72.6 | 76.1 | 74.2 | 73.6 | 1.7 | 2.2 |
| S6 | 17.2 | 17.7 | 16.7 | 19.6 | 16.6 | 16.8 | 17.4 | 1.1 | 6.6 |
| S7 | 4.1 | 4.3 | 4.7 | 3.0 | 4.5 | 4.5 | 4.2 | 0.6 | 14.7 |
| S8 | 1.4 | 1.2 | 1.0 | 2.3 | 1.2 | 1.2 | 1.4 | 0.4 | 32.9 |
| Follistatin (26) | | | | | | | | | |
| S1 | 24532.0 | 24535.2 | 24587.5 | 24207.8 | 24554.3 | 24644.2 | 24510.2 | 153.9 | 0.6 |
| S2 | 6152.2 | Excluded | 6095.4 | 6264.2 | 6129.2 | 6102.4 | 6148.7 | 68.4 | 1.1 |
| S3 | 1520.2 | 1535.3 | 1558.8 | 1534.9 | 1533.7 | 1536.1 | 1536.5 | 12.4 | 0.8 |
| S4 | 390.1 | 381.8 | 372.5 | 374.7 | 385.3 | 386.8 | 381.8 | 7.0 | 1.8 |
| S5 | 94.3 | 96.8 | 99.7 | 95.5 | 94.5 | 94.2 | 95.8 | 2.1 | 2.2 |
| S6 | 24.0 | 23.7 | 23.3 | 26.4 | 24.6 | 24.4 | 24.4 | 1.1 | 4.5 |
| S7 | 6.2 | 6.1 | 6.0 | 4.7 | 5.7 | 6.0 | 5.8 | 0.6 | 9.9 |
| S8 | 1.4 | 1.5 | 1.5 | 2.3 | 1.6 | 1.5 | 1.6 | 0.3 | 20.1 |
| G-CSF (57) | | | | | | | | | |
| S1 | 11189.8 | 11093.4 | 10850.4 | 10763.3 | 11087.4 | 11027.0 | 11001.9 | 162.2 | 1.5 |
| S2 | 2744.1 | Excluded | 2838.5 | 2889.9 | 2773.7 | 2792.3 | 2807.7 | 57.3 | 2.0 |
| S3 | 701.1 | 692.9 | 678.7 | 689.8 | 693.2 | 685.0 | 690.1 | 7.7 | 1.1 |
| S4 | 173.0 | 173.6 | 174.3 | 165.6 | 173.0 | 175.9 | 172.6 | 3.6 | 2.1 |
| S5 | 42.3 | 43.2 | 44.9 | 44.5 | 43.6 | 43.7 | 43.7 | 0.9 | 2.2 |
| S6 | 11.3 | 10.8 | 10.1 | 13.3 | 10.7 | 10.5 | 11.1 | 1.1 | 10.2 |
| S7 | 2.6 | 2.8 | 2.9 | 1.0 | 2.8 | 2.9 | 2.5 | 0.7 | 29.0 |
| S8 | 0.7 | 0.6 | 0.7 | 2.3 | 0.7 | 0.6 | 0.9 | 0.7 | 72.4 |
| sHEr-2/neu (12) | | | | | | | | | |
| S1 | 19298.4 | 19629.5 | 19393.9 | 18827.9 | 19540.3 | 19756.2 | 19407.7 | 327.6 | 1.7 |
| S2 | 5035.6 | Excluded | 4988.0 | 5238.5 | 4944.8 | 4870.5 | 5015.5 | 138.7 | 2.8 |
| S3 | 1213.7 | 1232.0 | 1220.8 | 1201.9 | 1223.4 | 1239.9 | 1222.0 | 13.4 | 1.1 |
| S4 | 303.5 | 305.0 | 304.0 | 302.6 | 305.8 | 304.2 | 304.2 | 1.2 | 0.4 |
| S5 | 78.9 | 77.3 | 78.2 | 75.8 | 77.8 | 77.1 | 77.5 | 1.1 | 1.4 |
| S6 | 19.0 | 19.2 | 19.2 | 21.5 | 18.9 | 19.2 | 19.5 | 1.0 | 5.2 |
| S7 | 4.7 | 4.8 | 4.7 | 3.8 | 4.9 | 4.8 | 4.6 | 0.4 | 8.8 |
| S8 | 1.2 | 1.2 | 1.3 | 1.8 | 1.2 | 1.2 | 1.3 | 0.2 | 16.6 |
| HGF (62) | | | | | | | | | |
| S1 | 25836.2 | 25658.7 | 25739.5 | 25069.3 | 25605.7 | 25421.0 | 25555.0 | 275.8 | 1.1 |
| S2 | 6306.0 | Excluded | 6369.3 | 6636.3 | 6435.7 | 6514.2 | 6452.2 | 128.7 | 2.0 |
| S3 | 1625.9 | 1598.2 | 1604.7 | 1638.2 | 1594.4 | 1594.8 | 1609.3 | 18.4 | 1.1 |
| S4 | 403.5 | 402.4 | 405.4 | 378.2 | 401.9 | 393.4 | 397.5 | 10.3 | 2.6 |
| S5 | 97.1 | 100.6 | 98.6 | 100.1 | 100.5 | 103.0 | 100.0 | 2.0 | 2.0 |
| S6 | 26.1 | 24.4 | 25.1 | 28.6 | 24.8 | 24.9 | 25.6 | 1.6 | 6.1 |
| S7 | 6.1 | 6.7 | 6.5 | 4.4 | 6.4 | 6.0 | 6.0 | 0.8 | 13.7 |
| S8 | 1.6 | 1.4 | 1.5 | 2.9 | 1.5 | 1.7 | 1.8 | 0.6 | 32.3 |
| sIL-6Ra (19) | | | | | | | | | |
| S1 | 9624.8 | 9566.0 | 9578.5 | 9644.0 | 9555.9 | 9535.3 | 9584.1 | 41.9 | 0.4 |
| S2 | 2356.3 | Excluded | 2396.5 | 2441.7 | 2407.1 | 2409.6 | 2402.2 | 30.7 | 1.3 |
| S3 | 612.2 | 598.8 | 588.0 | 583.0 | 590.9 | 595.9 | 594.8 | 10.2 | 1.7 |
| S4 | 146.3 | 149.8 | 156.4 | 142.3 | 151.3 | 147.3 | 148.9 | 4.8 | 3.2 |
| S5 | 38.0 | 36.6 | 36.7 | 39.2 | 37.3 | 38.7 | 37.7 | 1.1 | 2.8 |
| S6 | 9.2 | 10.0 | 8.6 | 10.9 | 9.2 | 9.2 | 9.5 | 0.8 | 8.3 |
| S7 | 2.4 | 2.0 | 2.9 | 1.3 | 2.4 | 2.3 | 2.2 | 0.5 | 24.3 |
| S8 | 0.6 | 0.7 | 0.5 | 1.6 | 0.6 | 0.6 | 0.8 | 0.4 | 57.7 |
| Leptin (78) | | | | | | | | | |
| S1 | 80547.0 | 80582.4 | 83854.3 | 74716.2 | 80744.3 | 80143.6 | 80097.9 | 2964.1 | 3.7 |
| S2 | 19981.8 | Excluded | 19048.5 | 20717.5 | 20071.9 | 20144.2 | 19992.8 | 601.3 | 3.0 |
| S3 | 4875.1 | 4890.0 | 5069.6 | 5040.8 | 4790.1 | 4830.6 | 4916.0 | 113.7 | 2.3 |
| S4 | 1275.8 | 1275.6 | 1240.2 | 1228.3 | 1309.3 | 1291.9 | 1270.2 | 30.7 | 2.4 |
| S5 | 310.8 | 305.9 | 311.8 | 303.3 | 301.6 | 303.6 | 306.2 | 4.2 | 1.4 |
| S6 | 74.4 | 77.7 | 76.6 | 83.5 | 77.9 | 77.7 | 78.0 | 3.0 | 3.9 |
| S7 | 21.1 | 19.8 | 20.0 | 17.7 | 19.9 | 19.9 | 19.7 | 1.1 | 5.5 |
| S8 | 4.6 | 4.7 | 4.7 | 5.5 | 4.7 | 4.7 | 4.8 | 0.3 | 6.9 |
| Osteopontin (77) | | | | | | | | | |
| S1 | 132678.6 | 157442.3 | 133675.3 | 131426.4 | 139094.9 | 129817.1 | 137355.8 | 10333.5 | 7.5 |
| S2 | 44885.3 | Excluded | 45565.7 | 45213.1 | 43182.2 | 44767.0 | 44722.6 | 915.5 | 2.0 |
| S3 | 9423.7 | 9813.2 | 9401.8 | 9476.6 | 9460.3 | 9479.5 | 9509.2 | 152.0 | 1.6 |
| S4 | 2497.8 | 2459.9 | 2480.8 | 2465.7 | 2515.8 | 2484.7 | 2484.1 | 20.6 | 0.8 |
| S5 | 611.2 | 613.0 | 616.0 | 611.7 | 606.6 | 615.8 | 612.4 | 3.5 | 0.6 |
| S6 | 153.3 | 153.5 | 151.7 | 165.1 | 151.8 | 150.8 | 154.4 | 5.4 | 3.5 |

TABLE 4-continued

|  | Day 1 | Day 2 | Day 3 | Day 4 | Day 5 | Day 6 | Mean | SD | % CV |
|---|---|---|---|---|---|---|---|---|---|
| S7 | 38.2 | 40.7 | 33.9 | 11.4 | 51.6 | 38.4 | 35.7 | 13.3 | 37.2 |
| S8 | 10.4 | 3.3 | 21.8 | 38.6 | OOR< | 13.1 | 17.5 | 13.5 | 77.6 |
| PDGF-AB/BB (47) | | | | | | | | | |
| S1 | 19928.0 | 20831.0 | 20103.5 | 18799.5 | 19479.0 | 19862.8 | 19834.0 | 674.2 | 3.4 |
| S2 | 5405.8 | Excluded | 5355.0 | 5927.0 | 5545.5 | 5399.7 | 5526.6 | 235.0 | 4.3 |
| S3 | 1268.8 | 1284.9 | 1265.0 | 1292.5 | 1248.6 | 1268.5 | 1271.4 | 15.5 | 1.2 |
| S4 | 319.5 | 333.3 | 327.7 | 299.5 | 321.6 | 321.6 | 320.5 | 11.5 | 3.6 |
| S5 | 83.9 | 79.0 | 83.0 | 83.6 | 84.7 | 82.9 | 82.8 | 2.0 | 2.4 |
| S6 | 20.4 | 19.7 | 19.1 | 22.8 | 20.2 | 20.7 | 20.5 | 1.3 | 6.2 |
| S7 | 4.8 | 5.5 | 5.5 | 4.2 | 4.8 | 4.7 | 4.9 | 0.5 | 10.1 |
| S8 | 1.3 | 1.2 | 1.2 | 1.7 | 1.3 | 1.4 | 1.4 | 0.2 | 13.0 |
| PECAM-1 (46) | | | | | | | | | |
| S1 | 117120.8 | 108996.1 | 106005.7 | 114000.0 | 110240.4 | 110634.8 | 111166.3 | 3897.8 | 3.5 |
| S2 | 26097.1 | Excluded | 27913.5 | 26214.1 | 27113.9 | 27019.7 | 26871.6 | 741.3 | 2.8 |
| S3 | 6880.6 | 6777.3 | 6649.0 | 6893.4 | 6721.2 | 6759.8 | 6780.2 | 93.8 | 1.4 |
| S4 | 1698.9 | 1705.5 | 1735.0 | 1699.6 | 1745.7 | 1730.1 | 1719.1 | 20.3 | 1.2 |
| S5 | 421.4 | 422.2 | 417.5 | 415.1 | 405.8 | 409.8 | 415.3 | 6.5 | 1.6 |
| S6 | 105.2 | 105.2 | 104.8 | 114.3 | 115.1 | 112.2 | 109.4 | 4.9 | 4.5 |
| S7 | 32.1 | 31.8 | 40.6 | 18.4 | 23.2 | 25.7 | 28.7 | 7.9 | 27.4 |
| S8 | OOR< | OOR< | OOR< | 14.0 | 7.0 | 5.3 | 8.8 | 4.6 | 52.3 |
| Prolactin (52) | | | | | | | | | |
| S1 | 156096.1 | 155617.1 | 156029.2 | 148442.6 | 156318.2 | 159647.5 | 155358.5 | 3693.4 | 2.4 |
| S2 | 38804.1 | Excluded | 38847.5 | 41126.9 | 38761.8 | 37780.8 | 39064.1 | 1235.7 | 3.2 |
| S3 | 9754.5 | 9725.4 | 9699.4 | 9754.8 | 9697.6 | 9994.5 | 9771.0 | 112.3 | 1.1 |
| S4 | 2418.6 | 2435.5 | 2447.8 | 2292.1 | 2456.6 | 2403.1 | 2408.9 | 60.5 | 2.5 |
| S5 | 616.5 | 601.6 | 608.3 | 628.1 | 604.8 | 601.0 | 610.0 | 10.5 | 1.7 |
| S6 | 147.1 | 156.9 | 147.5 | 182.9 | 148.3 | 154.2 | 156.2 | 13.7 | 8.8 |
| S7 | 40.7 | 35.7 | 42.0 | 20.0 | 42.4 | 38.8 | 36.6 | 8.5 | 23.2 |
| S8 | 8.7 | 10.2 | 8.1 | 24.0 | 7.7 | 9.0 | 11.3 | 6.3 | 56.0 |
| SCF (65) | | | | | | | | | |
| S1 | 24698.7 | 24715.3 | 23996.0 | 21962.0 | 24069.7 | 23888.2 | 23888.3 | 1009.5 | 4.2 |
| S2 | 6127.6 | Excluded | 6341.9 | 7143.3 | 6338.7 | 6330.9 | 6456.4 | 394.6 | 6.1 |
| S3 | 1539.2 | 1521.6 | 1498.5 | 1554.8 | 1495.1 | 1521.0 | 1521.7 | 23.1 | 1.5 |
| S4 | 383.8 | 391.4 | 391.4 | 360.5 | 392.0 | 382.4 | 383.6 | 12.1 | 3.1 |
| S5 | 96.9 | 94.8 | 96.3 | 94.2 | 97.1 | 96.4 | 95.9 | 1.2 | 1.2 |
| S6 | 23.5 | 24.0 | 23.4 | 27.9 | 22.9 | 24.5 | 24.4 | 1.8 | 7.3 |
| S7 | 6.2 | 6.1 | 6.2 | 4.6 | 6.4 | 5.7 | 5.9 | 0.6 | 11.0 |
| S8 | 1.5 | 1.5 | 1.5 | 2.5 | 1.4 | 1.6 | 1.7 | 0.4 | 25.9 |
| sTIE-2 (64) | | | | | | | | | |
| S1 | 151452.2 | 153315.2 | 149429.5 | 144235.7 | 145049.6 | 148713.2 | 148699.2 | 3540.1 | 2.4 |
| S2 | 38778.5 | Excluded | 39293.6 | 41008.7 | 40525.3 | 39408.1 | 39802.8 | 927.4 | 2.3 |
| S3 | 9411.7 | 9491.9 | 9379.1 | 9506.0 | 9132.1 | 9354.9 | 9379.4 | 135.1 | 1.4 |
| S4 | 2421.5 | 2434.2 | 2383.8 | 2279.2 | 2450.9 | 2413.1 | 2397.1 | 62.0 | 2.6 |
| S5 | 593.5 | 580.6 | 621.3 | 603.5 | 609.9 | 595.7 | 600.7 | 14.1 | 2.4 |
| S6 | 148.3 | 153.1 | 138.7 | 182.0 | 142.3 | 152.3 | 152.8 | 15.4 | 10.1 |
| S7 | 38.4 | 37.4 | 42.4 | 19.3 | 38.6 | 34.4 | 35.1 | 8.1 | 23.2 |
| S8 | 8.9 | 9.0 | 8.1 | 24.0 | 9.4 | 10.7 | 11.7 | 6.1 | 52.1 |
| sVEGFR-1 (76) | | | | | | | | | |
| S1 | 18341.1 | 18355.7 | 18348.7 | 18198.8 | 18420.0 | 18186.9 | 18308.5 | 94.0 | 0.5 |
| S2 | 4600.3 | Excluded | 4593.2 | 4744.7 | 4540.3 | 4710.7 | 4637.8 | 86.1 | 1.9 |
| S3 | 1142.7 | 1169.9 | 1147.1 | 1114.5 | 1169.7 | 1103.8 | 1141.3 | 27.5 | 2.4 |
| S4 | 287.3 | 275.2 | 284.5 | 282.2 | 280.7 | 296.3 | 284.4 | 7.1 | 2.5 |
| S5 | 71.9 | 73.2 | 73.9 | 73.7 | 72.9 | 72.2 | 73.0 | 0.8 | 1.1 |
| S6 | 18.1 | 17.6 | 16.8 | 19.9 | 17.8 | 17.2 | 17.9 | 1.1 | 6.0 |
| S7 | 4.2 | 5.8 | 5.0 | 1.5 | 4.4 | 4.5 | 4.2 | 1.5 | 35.1 |
| S8 | 1.3 | 0.5 | 1.0 | 3.9 | 1.2 | 1.3 | 1.5 | 1.2 | 78.8 |
| sVEGFR-2 (45) | | | | | | | | | |
| S1 | 145503.5 | 149302.2 | 148601.7 | 139240.5 | 144509.7 | 146229.3 | 145564.5 | 3598.5 | 2.5 |
| S2 | 37993.3 | Excluded | 36955.1 | 40750.2 | 38223.2 | 37665.1 | 38317.4 | 1441.7 | 3.8 |
| S3 | 9142.8 | 9139.9 | 9335.1 | 9145.2 | 9076.9 | 9187.6 | 9171.2 | 87.7 | 1.0 |
| S4 | 2318.0 | 2406.7 | 2292.5 | 2213.5 | 2330.1 | 2322.3 | 2313.8 | 62.4 | 2.7 |
| S5 | 582.3 | 558.9 | 586.2 | 583.3 | 590.0 | 579.0 | 579.9 | 11.0 | 1.9 |
| S6 | 147.1 | 144.2 | 144.7 | 166.1 | 141.9 | 147.2 | 148.5 | 8.8 | 6.0 |
| S7 | 34.7 | 38.8 | 35.7 | 25.8 | 36.4 | 34.9 | 34.4 | 4.5 | 13.0 |
| S8 | 9.6 | 8.3 | 9.2 | 16.1 | 9.1 | 9.5 | 10.3 | 2.9 | 27.9 |

TABLE 5

| | Day 1 | Day 2 | Day 3 | Day 4 | Day 5 | Mean | SD | CV (%) | Calculated | Recovery (%) |
|---|---|---|---|---|---|---|---|---|---|---|
| sEGFR (15) | | | | | | | | | | |
| QC1 | 151277.6 | 121453.5 | 120047.5 | 127761.5 | 125414.8 | 129191.0 | 12723.9 | 9.8 | 129191.0 | 100.0 |
| QC2 | 84573.1 | 78560.6 | 75618.4 | 79090.6 | 81728.2 | 79914.2 | 3389.7 | 4.2 | 62145.3 | 128.6 |
| QC3 | 45431.0 | 45746.5 | 45296.4 | 38547.9 | 44528.2 | 43910.1 | 3030.8 | 6.9 | 45719.7 | 96.0 |
| QC4 | 33781.5 | 34133.7 | 36095.2 | 30832.7 | 34008.8 | 33770.4 | 1885.7 | 5.6 | 33718.3 | 100.2 |
| QC5 | 30332.4 | 31566.1 | 32165.4 | 27694.6 | 31081.4 | 30568.0 | 1740.9 | 5.7 | 30338.4 | 100.8 |
| QC6 | 29243.3 | 30010.3 | 31300.1 | 27130.4 | 30337.6 | 29604.4 | 1567.6 | 5.3 | 29271.0 | 101.1 |
| QC7 | 27643.3 | 31297.0 | 30406.2 | 27154.2 | 30190.6 | 29338.2 | 1826.7 | 6.2 | 28949.8 | 101.3 |
| QC8 | 29004.1 | 29720.2 | 28836.8 | 26486.7 | 29064.6 | 28622.5 | 1240.3 | 4.3 | 28622.5 | 100.0 |
| FGF-basic (44) | | | | | | | | | | |
| QC1 | 26922.0 | 40168.3 | 24579.1 | 27006.1 | 24650.0 | 28665.1 | 6537.0 | 22.8 | 28665.1 | 100.0 |
| QC2 | 9105.8 | 11600.6 | 8805.5 | 9957.6 | 9468.0 | 9787.5 | 1100.8 | 11.2 | 9635.6 | 101.6 |
| QC3 | 2846.2 | 2990.8 | 2984.0 | 2657.4 | 2808.6 | 2857.4 | 138.1 | 4.8 | 3292.5 | 86.8 |
| QC4 | 1085.3 | 1040.8 | 1143.2 | 990.3 | 1079.2 | 1067.7 | 56.7 | 5.3 | 1178.1 | 90.6 |
| QC5 | 453.1 | 427.8 | 477.9 | 424.7 | 445.3 | 445.8 | 21.5 | 4.8 | 473.3 | 94.2 |
| QC6 | 239.0 | 217.5 | 235.4 | 220.6 | 221.8 | 226.9 | 9.7 | 4.3 | 238.4 | 95.2 |
| QC7 | 171.1 | 163.3 | 163.8 | 155.3 | 159.6 | 162.6 | 5.8 | 3.6 | 160.0 | 101.6 |
| QC8 | 141.7 | 107.1 | 124.7 | 118.2 | 112.8 | 120.9 | 13.3 | 11.0 | 120.9 | 100.0 |
| Follistatin (26) | | | | | | | | | | |
| QC1 | 46919.9 | 37698.4 | 45692.9 | 44498.7 | 43140.2 | 43590.0 | 3579.4 | 8.2 | 43590.0 | 100.0 |
| QC2 | 16875.2 | 14512.9 | 15719.4 | 16111.7 | 15220.5 | 15687.9 | 893.0 | 5.7 | 14764.8 | 106.3 |
| QC3 | 6158.4 | 5709.4 | 6167.1 | 5224.0 | 5291.2 | 5710.0 | 453.2 | 7.9 | 5464.1 | 104.5 |
| QC4 | 2446.3 | 2305.9 | 2440.1 | 2102.8 | 2152.4 | 2289.5 | 159.0 | 6.9 | 2138.2 | 107.1 |
| QC5 | 1087.4 | 996.7 | 1082.2 | 952.8 | 970.8 | 1018.0 | 63.0 | 6.2 | 998.0 | 102.0 |
| QC6 | 628.9 | 565.9 | 604.8 | 561.0 | 543.7 | 580.8 | 34.9 | 6.0 | 574.1 | 101.2 |
| QC7 | 488.1 | 439.8 | 440.6 | 441.1 | 431.3 | 448.2 | 22.7 | 5.1 | 428.4 | 104.6 |
| QC8 | 414.4 | 298.7 | 364.5 | 344.6 | 338.9 | 352.2 | 42.2 | 12.0 | 352.2 | 100.0 |
| G-CSF (57) | | | | | | | | | | |
| QC1 | 8871.6 | 7745.6 | 8506.4 | 10153.7 | 9186.1 | 8892.7 | 886.3 | 10.0 | 8892.7 | 100.0 |
| QC2 | 2997.7 | 2744.6 | 2736.6 | 3002.0 | 3044.6 | 2905.1 | 151.3 | 5.2 | 3018.4 | 96.2 |
| QC3 | 1024.9 | 1005.8 | 1017.3 | 996.7 | 1085.0 | 1025.9 | 34.7 | 3.4 | 1060.3 | 96.8 |
| QC4 | 393.7 | 395.1 | 402.6 | 416.1 | 455.3 | 412.5 | 25.5 | 6.2 | 407.6 | 101.2 |
| QC5 | 181.3 | 181.3 | 193.0 | 207.6 | 213.0 | 195.2 | 14.7 | 7.5 | 190.1 | 102.7 |
| QC6 | 109.1 | 114.4 | 118.6 | 135.0 | 132.1 | 121.8 | 11.3 | 9.2 | 117.5 | 103.6 |
| QC7 | 81.4 | 93.1 | 89.7 | 113.8 | 100.8 | 95.8 | 12.3 | 12.8 | 93.4 | 102.6 |
| QC8 | 78.3 | 69.3 | 74.8 | 94.7 | 89.2 | 81.3 | 10.4 | 12.9 | 81.3 | 100.0 |
| sHEr-2/neu (12) | | | | | | | | | | |
| QC1 | 32950.9 | 32447.4 | 33980.7 | 33510.1 | 30097.9 | 32597.4 | 1511.8 | 4.6 | 32597.4 | 100.0 |
| QC2 | 16242.3 | 15717.0 | 14940.7 | 16814.7 | 14370.8 | 15617.1 | 980.5 | 6.3 | 16466.5 | 94.8 |
| QC3 | 10617.9 | 10360.0 | 10160.8 | 9686.6 | 9619.9 | 10089.0 | 430.2 | 4.3 | 11089.6 | 91.0 |
| QC4 | 9198.9 | 8754.3 | 9171.0 | 9559.5 | 8621.6 | 9061.1 | 376.4 | 4.2 | 9297.2 | 97.5 |
| QC5 | 9029.9 | 8525.5 | 8579.1 | 9047.7 | 8155.2 | 8667.5 | 376.3 | 4.3 | 8699.8 | 99.6 |
| QC6 | 8524.5 | 8439.6 | 8435.4 | 9291.0 | 8567.8 | 8651.7 | 361.8 | 4.2 | 8500.7 | 101.8 |
| QC7 | 8317.4 | 8541.2 | 8507.6 | 9250.2 | 8215.6 | 8566.4 | 405.2 | 4.7 | 8434.3 | 101.6 |
| QC8 | 8724.0 | 8032.6 | 7905.9 | 9039.2 | 8303.8 | 8401.1 | 474.8 | 5.7 | 8401.1 | 100.0 |
| HGF (62) | | | | | | | | | | |
| QC1 | 55543.0 | 49431.7 | 51509.4 | 58031.0 | 53757.4 | 53654.5 | 3360.2 | 6.3 | 53654.5 | 100.0 |
| QC2 | 17268.8 | 15778.3 | 16411.2 | 19195.8 | 17556.9 | 17242.2 | 1299.0 | 7.5 | 18433.4 | 93.5 |
| QC3 | 6185.2 | 5760.6 | 6141.8 | 6274.6 | 6203.0 | 6113.0 | 202.7 | 3.3 | 6693.0 | 91.3 |
| QC4 | 2736.5 | 2450.1 | 2737.8 | 2812.1 | 2810.6 | 2709.4 | 149.6 | 5.5 | 2779.6 | 97.5 |
| QC5 | 1474.0 | 1319.1 | 1497.6 | 1538.7 | 1477.2 | 1461.3 | 83.6 | 5.7 | 1475.1 | 99.1 |
| QC6 | 1065.4 | 909.0 | 1030.8 | 1108.8 | 1091.8 | 1041.2 | 79.5 | 7.6 | 1040.3 | 100.1 |
| QC7 | 876.3 | 821.8 | 906.4 | 963.9 | 962.5 | 906.2 | 60.2 | 6.6 | 895.3 | 101.2 |
| QC8 | 866.6 | 690.1 | 799.1 | 902.0 | 856.5 | 822.8 | 82.9 | 10.1 | 822.8 | 100.0 |
| sIL-6Ra (19) | | | | | | | | | | |
| QC2 | 30039.0 | 27974.3 | 26883.7 | 30811.3 | 30921.8 | 29326.0 | 1806.5 | 6.2 | 29326.0 | 100.0 |
| QC3 | 23922.0 | 21704.0 | 21197.8 | 22098.2 | 23481.2 | 22480.6 | 1169.8 | 5.2 | 22394.1 | 100.4 |
| QC4 | 21317.7 | 19036.1 | 19703.2 | 21753.2 | 22115.0 | 20785.0 | 1343.4 | 6.5 | 20083.5 | 103.5 |
| QC5 | 19619.8 | 19380.2 | 18719.8 | 21086.8 | 21180.1 | 19997.3 | 1088.7 | 5.4 | 19313.3 | 103.5 |
| QC6 | 19280.6 | 18208.3 | 18462.0 | 21219.6 | 21496.1 | 19733.3 | 1538.1 | 7.8 | 19056.6 | 103.6 |
| QC7 | 18882.5 | 18873.1 | 18074.2 | 20602.8 | 21582.5 | 19603.0 | 1441.1 | 7.4 | 18971.0 | 103.3 |
| QC8 | 19420.4 | 17487.3 | 17004.1 | 19851.8 | 20877.3 | 18928.2 | 1633.5 | 8.6 | 18928.2 | 100.0 |
| Leptin (78) | | | | | | | | | | |
| QC1 | 144237.0 | 112564.6 | 108209.6 | 106556.2 | 123811.6 | 119075.8 | 15594.3 | 13.1 | 119075.8 | 100.0 |
| QC2 | 52862.3 | 47090.5 | 42996.4 | 46808.2 | 53991.3 | 48749.7 | 4582.9 | 9.4 | 44710.9 | 109.0 |
| QC3 | 23544.7 | 21187.9 | 21719.5 | 17781.3 | 23730.5 | 21592.8 | 2402.4 | 11.1 | 19922.5 | 108.4 |

TABLE 5-continued

| | Day 1 | Day 2 | Day 3 | Day 4 | Day 5 | Mean | SD | CV (%) | Calculated | Recovery (%) |
|---|---|---|---|---|---|---|---|---|---|---|
| QC4 | 13468.3 | 12768.3 | 12351.8 | 10543.8 | 13254.7 | 12477.4 | 1164.6 | 9.3 | 11659.8 | 107.0 |
| QC5 | 9895.5 | 9629.7 | 9518.5 | 8070.4 | 9622.9 | 9347.4 | 727.3 | 7.8 | 8905.5 | 105.0 |
| QC6 | 8523.1 | 8297.7 | 8389.2 | 7131.2 | 8839.7 | 8236.2 | 650.9 | 7.9 | 7987.4 | 103.1 |
| QC7 | 7681.5 | 7958.6 | 7731.4 | 6506.7 | 8163.4 | 7608.3 | 645.1 | 8.5 | 7681.4 | 99.0 |
| QC8 | 7799.6 | 7815.2 | 7523.2 | 6581.5 | 7922.5 | 7528.4 | 549.5 | 7.3 | 7528.4 | 100.0 |
| Osteopontin (77) | | | | | | | | | | |
| QC1 | 160984.7 | 165424.9 | 166260.5 | 201494.8 | 177840.9 | 174401.2 | 16376.4 | 9.4 | 174401.2 | 100.0 |
| QC2 | 76040.3 | 81669.2 | 72822.1 | 88300.5 | 85701.7 | 80906.8 | 6466.9 | 8.0 | 77600.2 | 104.3 |
| QC3 | 43560.5 | 46224.9 | 42871.4 | 45904.1 | 48873.8 | 45486.9 | 2384.4 | 5.2 | 45333.2 | 100.3 |
| QC4 | 32517.6 | 35576.3 | 32885.4 | 36975.0 | 37692.1 | 35129.3 | 2346.8 | 6.7 | 34577.6 | 101.6 |
| QC5 | 29085.8 | 32310.1 | 28615.0 | 32803.2 | 34133.2 | 31389.5 | 2417.6 | 7.7 | 30992.3 | 101.3 |
| QC6 | 28753.4 | 30817.0 | 28686.1 | 32286.0 | 33711.9 | 30850.9 | 2198.4 | 7.1 | 29797.3 | 103.5 |
| QC7 | 26718.4 | 31393.7 | 27408.8 | 31519.2 | 32900.6 | 29988.2 | 2745.3 | 9.2 | 29398.9 | 102.0 |
| QC8 | 27430.5 | 29302.0 | 26117.8 | 30734.2 | 32414.1 | 29199.7 | 2516.2 | 8.6 | 29199.7 | 100.0 |
| PDGF-AB/BB (47) | | | | | | | | | | |
| QC1 | 47772.2 | 34658.8 | 48023.0 | 42570.5 | 40804.3 | 42765.8 | 5529.7 | 12.9 | 42765.8 | 100.0 |
| QC2 | 18282.4 | 15006.6 | 15221.8 | 17843.4 | 15676.2 | 16406.1 | 1539.5 | 9.4 | 15588.5 | 105.2 |
| QC3 | 7237.0 | 6581.8 | 6786.5 | 6625.1 | 6381.9 | 6722.5 | 321.8 | 4.8 | 6529.4 | 103.0 |
| QC4 | 3927.0 | 3718.3 | 3728.3 | 3690.6 | 3570.3 | 3726.9 | 128.4 | 3.4 | 3509.7 | 106.2 |
| QC5 | 2712.4 | 2680.8 | 2584.5 | 2671.1 | 2558.2 | 2641.4 | 66.4 | 2.5 | 2503.2 | 105.5 |
| QC6 | 2286.4 | 2206.1 | 2240.7 | 2305.4 | 2248.2 | 2257.4 | 39.2 | 1.7 | 2167.7 | 104.1 |
| QC7 | 1976.8 | 2271.8 | 2039.6 | 2107.2 | 2158.3 | 2110.7 | 113.2 | 5.4 | 2055.8 | 102.7 |
| QC8 | 2120.8 | 1958.1 | 1911.7 | 1968.2 | 2040.6 | 1999.9 | 81.9 | 4.1 | 1999.9 | 100.0 |
| PECAM-1 (46) | | | | | | | | | | |
| QC1 | 215657.8 | 193572.8 | 216427.6 | 196725.7 | 216117.0 | 207700.2 | 11514.7 | 5.5 | 207700.2 | 100.0 |
| QC2 | 77359.9 | 73266.8 | 74515.0 | 79862.9 | 80133.6 | 77027.6 | 3092.5 | 4.0 | 75409.8 | 102.1 |
| QC3 | 34173.4 | 33063.7 | 34176.0 | 32261.9 | 34736.1 | 33682.2 | 999.4 | 3.0 | 31312.9 | 107.6 |
| QC4 | 18452.9 | 18961.9 | 18155.9 | 17864.2 | 20047.7 | 18696.5 | 857.4 | 4.6 | 16614.0 | 112.5 |
| QC5 | 12376.7 | 13107.5 | 12376.2 | 12238.7 | 13454.2 | 12710.6 | 537.8 | 4.2 | 11714.4 | 108.5 |
| QC6 | 10336.4 | 10714.3 | 9972.1 | 10199.8 | 11470.4 | 10538.6 | 586.4 | 5.6 | 10081.1 | 104.5 |
| QC7 | 9155.6 | 10267.3 | 9328.3 | 9352.3 | 10393.1 | 9699.3 | 582.6 | 6.0 | 9536.7 | 101.7 |
| QC8 | 9057.5 | 9560.0 | 8656.5 | 9049.5 | 9999.1 | 9264.5 | 521.0 | 5.6 | 9264.5 | 100.0 |
| Prolactin (52) | | | | | | | | | | |
| QC1 | 266909.9 | 236657.1 | 328889.0 | 311790.8 | 325131.4 | 293875.7 | 40388.5 | 13.7 | 293875.7 | 100.0 |
| QC2 | 88169.9 | 89645.3 | 104987.3 | 107984.6 | 108547.4 | 99866.9 | 10109.0 | 10.1 | 102325.2 | 97.6 |
| QC3 | 35322.1 | 37043.9 | 39768.5 | 37912.3 | 36555.8 | 37320.5 | 1658.2 | 4.4 | 38475.0 | 97.0 |
| QC4 | 16894.2 | 18134.7 | 18967.6 | 18362.1 | 19586.5 | 18389.1 | 1008.3 | 5.5 | 17191.7 | 107.0 |
| QC5 | 10318.9 | 10138.9 | 10601.0 | 9857.7 | 9935.8 | 10170.4 | 300.5 | 3.0 | 10097.2 | 100.7 |
| QC6 | 7862.3 | 7843.1 | 8063.6 | 7662.9 | 7861.1 | 7858.6 | 141.9 | 1.8 | 7732.4 | 101.6 |
| QC7 | 7026.3 | 7276.3 | 7195.6 | 6923.3 | 7141.4 | 7112.6 | 139.4 | 2.0 | 6944.1 | 102.4 |
| QC8 | 6767.9 | 6216.4 | 6635.8 | 6489.9 | 6639.8 | 6550.0 | 210.8 | 3.2 | 6550.0 | 100.0 |
| SCF (65) | | | | | | | | | | |
| QC1 | 60329.9 | 54420.4 | 56276.6 | 54321.0 | 56272.7 | 56324.1 | 2433.5 | 4.3 | 56324.1 | 100.0 |
| QC2 | 17848.2 | 18726.6 | 17133.8 | 19015.4 | 18652.1 | 18275.2 | 771.2 | 4.2 | 18938.2 | 96.5 |
| QC3 | 5787.3 | 6262.2 | 6187.9 | 5305.3 | 6147.9 | 5938.1 | 398.3 | 6.7 | 6476.3 | 91.7 |
| QC4 | 2159.0 | 2228.2 | 2306.9 | 1953.6 | 2385.6 | 2206.7 | 164.9 | 7.5 | 2322.3 | 95.0 |
| QC5 | 864.1 | 932.9 | 958.6 | 782.6 | 963.1 | 900.3 | 76.8 | 8.5 | 937.6 | 96.0 |
| QC6 | 463.9 | 459.8 | 487.4 | 430.0 | 507.3 | 469.7 | 29.3 | 6.2 | 476.1 | 98.7 |
| QC7 | 303.8 | 330.2 | 316.9 | 314.0 | 334.0 | 319.8 | 12.3 | 3.9 | 322.2 | 99.2 |
| QC8 | 248.5 | 236.8 | 238.9 | 254.1 | 248.2 | 245.3 | 7.2 | 3.0 | 245.3 | 100.0 |
| sTIE-2 (64) | | | | | | | | | | |
| QC1 | 170902.0 | 150892.2 | 152000.8 | 161237.2 | 143129.4 | 155632.3 | 10683.6 | 6.9 | 155632.3 | 100.0 |
| QC2 | 63043.3 | 56555.3 | 57754.8 | 61342.6 | 58593.6 | 59457.9 | 2668.3 | 4.5 | 58568.7 | 101.5 |
| QC3 | 27267.6 | 24882.0 | 26031.0 | 25228.9 | 25260.1 | 25733.9 | 954.7 | 3.7 | 26214.2 | 98.2 |
| QC4 | 16024.7 | 13934.2 | 14833.8 | 16164.7 | 15584.2 | 15308.3 | 926.8 | 6.1 | 15429.4 | 99.2 |
| QC5 | 11940.2 | 10270.7 | 10813.9 | 12286.1 | 12009.5 | 11464.1 | 872.7 | 7.6 | 11834.4 | 96.9 |
| QC6 | 10982.6 | 9006.9 | 9655.1 | 11506.7 | 11055.1 | 10441.3 | 1058.3 | 10.1 | 10636.1 | 98.2 |
| QC7 | 10145.5 | 9248.4 | 9271.5 | 11351.6 | 10676.0 | 10138.6 | 908.9 | 9.0 | 10236.7 | 99.0 |
| QC8 | 10669.9 | 8943.6 | 9007.9 | 11304.8 | 10258.5 | 10036.9 | 1038.2 | 10.3 | 10036.9 | 100.0 |
| sVEGFR-1 (76) | | | | | | | | | | |
| QC1 | 17205.6 | 11938.6 | 15333.3 | 18656.4 | 14823.0 | 15591.4 | 2549.5 | 16.4 | 15591.4 | 100.0 |
| QC2 | 5850.4 | 4903.5 | 5494.8 | 6044.4 | 4719.5 | 5402.5 | 578.1 | 10.7 | 5295.6 | 102.0 |
| QC3 | 2004.1 | 1875.9 | 1973.3 | 1906.7 | 1574.5 | 1866.9 | 171.3 | 9.2 | 1863.7 | 100.2 |
| QC4 | 784.0 | 718.9 | 790.4 | 746.7 | 666.0 | 741.2 | 51.1 | 6.9 | 719.8 | 103.0 |
| QC5 | 372.2 | 333.7 | 370.3 | 373.3 | 318.6 | 353.6 | 25.7 | 7.3 | 338.4 | 104.5 |
| QC6 | 246.2 | 195.1 | 236.2 | 237.0 | 206.1 | 224.1 | 22.2 | 9.9 | 211.3 | 106.1 |

TABLE 5-continued

|  | Day 1 | Day 2 | Day 3 | Day 4 | Day 5 | Mean | SD | CV (%) | Calculated | Recovery (%) |
|---|---|---|---|---|---|---|---|---|---|---|
| QC7 | 192.0 | 166.7 | 174.0 | 204.6 | 178.8 | 183.2 | 15.1 | 8.2 | 169.0 | 108.4 |
| QC8 | 171.8 | 105.4 | 145.9 | 168.4 | 147.3 | 147.8 | 26.5 | 17.9 | 147.8 | 100.0 |
| sVEGFR-2 (45) | | | | | | | | | | |
| QC1 | 150145.8 | 125294.1 | 123188.5 | 145969.2 | 134153.4 | 135750.2 | 12055.4 | 8.9 | 135750.2 | 100.0 |
| QC2 | 47764.8 | 48641.4 | 46772.5 | 52345.2 | 49355.9 | 48975.9 | 2117.2 | 4.3 | 50684.4 | 96.6 |
| QC3 | 17911.4 | 18683.1 | 19400.4 | 17886.6 | 19047.0 | 18585.7 | 676.3 | 3.6 | 22329.1 | 83.2 |
| QC4 | 10946.0 | 10971.8 | 11178.0 | 10907.0 | 11759.2 | 11152.4 | 355.1 | 3.2 | 12877.4 | 86.6 |
| QC5 | 8700.4 | 8652.8 | 8965.5 | 9165.0 | 9213.6 | 8939.4 | 257.9 | 2.9 | 9726.8 | 91.9 |
| QC6 | 7927.2 | 8104.2 | 8117.2 | 8742.2 | 9066.0 | 8391.5 | 487.8 | 5.8 | 8676.6 | 96.7 |
| QC7 | 7617.2 | 8180.3 | 7963.2 | 8512.9 | 8782.5 | 8211.2 | 456.3 | 5.6 | 8326.5 | 98.6 |
| QC8 | 7920.4 | 7860.8 | 7705.8 | 8501.3 | 8769.4 | 8151.5 | 458.5 | 5.6 | 8151.5 | 100.0 |

TABLE 6

|  | Day 1 | Day 2 | Day 3 | Day 4 | Day 5 | Mean | SD | % CV | Calculcated | Recovery (%) |
|---|---|---|---|---|---|---|---|---|---|---|
| sEGFR | | | | | | | | | | |
| L1 | 151277.6 | 121453.5 | 120047.5 | 127761.5 | 125414.8 | 129191.0 | 12723.9 | 9.8 | 129191.0 | 100.0 |
| L2 | 77912.6 | 79335.8 | 82371.8 | 75478.2 | 81862.6 | 79392.2 | 2850.1 | 3.6 | 32297.7 | 245.8 |
| L3 | 20460.2 | 22357.8 | Excluded | 18971.2 | 22063.3 | 20963.1 | 1568.0 | 7.5 | 8074.7 | 259.6 |
| L4 | 4659.9 | 4791.9 | 4834.8 | 4337.4 | 5140.7 | 4752.9 | 291.5 | 6.1 | 2018.6 | 235.5 |
| L5 | 975.1 | 1070.1 | 1064.4 | Excluded | 1079.9 | 1047.4 | 48.6 | 4.6 | 504.7 | 207.5 |
| L6 | 292.4 | 248.8 | 229.8 | 308.3 | 245.5 | 265.0 | 33.6 | 12.7 | 126.2 | 210.0 |
| FGF-basic (44) | | | | | | | | | | |
| L1 | 26922.0 | 40168.3 | 24579.1 | 27006.1 | 24650.0 | 28665.1 | 6537.0 | 22.8 | 28665.1 | 100.0 |
| L2 | 9278.7 | 12111.3 | 10026.8 | 9718.5 | 9808.7 | 10188.8 | 1108.6 | 10.9 | 7166.3 | 142.2 |
| L3 | 2150.7 | 2364.2 | Excluded | 2177.1 | 2319.0 | 2252.8 | 104.8 | 4.7 | 1791.6 | 125.7 |
| L4 | 615.1 | 584.2 | 642.8 | 606.4 | 654.3 | 620.6 | 28.2 | 4.5 | 447.9 | 138.5 |
| L5 | 133.6 | 136.1 | 148.1 | Excluded | 140.2 | 139.5 | 6.3 | 4.5 | 112.0 | 124.6 |
| L6 | 34.4 | 33.4 | 26.7 | 36.7 | 26.9 | 31.6 | 4.6 | 14.4 | 28.0 | 113.0 |
| Follistatin (26) | | | | | | | | | | |
| L1 | 46919.9 | 37698.4 | 45692.9 | 44498.7 | 43140.2 | 43590.0 | 3579.4 | 8.2 | 43590.0 | 100.0 |
| L2 | 11700.3 | 10566.4 | 12131.1 | 11343.1 | 11144.9 | 11377.2 | 588.5 | 5.2 | 10897.5 | 104.4 |
| L3 | 2959.9 | 2913.9 | Excluded | 2737.7 | 2832.1 | 2860.9 | 97.7 | 3.4 | 2724.4 | 105.0 |
| L4 | 766.7 | 763.1 | 758.8 | 698.7 | 700.4 | 737.6 | 34.8 | 4.7 | 681.1 | 108.3 |
| L5 | 192.7 | 182.2 | 189.5 | Excluded | 176.2 | 185.2 | 7.4 | 4.0 | 170.3 | 108.7 |
| L6 | 41.4 | 39.6 | 38.7 | 53.8 | 40.8 | 42.9 | 6.2 | 14.4 | 42.6 | 100.7 |
| L7 | 8.5 | 14.4 | 7.0 | 15.8 | 11.3 | 11.4 | 3.7 | 32.8 | 10.6 | 107.2 |
| G-CSF (57) | | | | | | | | | | |
| L1 | 8871.6 | 7745.6 | 8506.4 | 10153.7 | 9186.1 | 8892.7 | 886.3 | 10.0 | 8892.7 | 100.0 |
| L2 | 4401.1 | 3903.9 | 4421.6 | 4862.0 | 4649.8 | 4447.7 | 357.4 | 8.0 | 2223.2 | 200.1 |
| L3 | 1353.7 | 1362.6 | Excluded | 1275.6 | 1460.0 | 1363.0 | 75.6 | 5.5 | 555.8 | 245.2 |
| L4 | 332.0 | 351.5 | 360.2 | 358.0 | 386.0 | 357.5 | 19.4 | 5.4 | 138.9 | 257.3 |
| L5 | 69.3 | 89.4 | 86.7 | Excluded | 88.0 | 83.3 | 9.4 | 11.3 | 34.7 | 239.9 |
| L6 | 11.6 | 22.2 | 19.3 | 33.0 | 21.9 | 21.6 | 7.7 | 35.6 | 8.7 | 248.4 |
| L7 | 3.3 | 3.1 | 4.1 | 15.9 | 6.0 | 6.5 | 5.4 | 83.5 | 2.2 | 298.1 |
| sHEr-2/neu (12) | | | | | | | | | | |
| L1 | 32950.9 | 32447.4 | 33980.7 | 33510.1 | 30097.9 | 32597.4 | 1511.8 | 4.6 | 32597.4 | 100.0 |
| L2 | 12022.4 | 12032.5 | 12618.6 | 12523.3 | 11335.4 | 12106.4 | 510.6 | 4.2 | 8149.3 | 148.6 |
| L3 | 3087.8 | 3191.4 | Excluded | 3067.7 | 3138.9 | 3121.4 | 55.4 | 1.8 | 2037.5 | 153.2 |
| L4 | 772.8 | 802.2 | 807.4 | 788.3 | 831.7 | 800.5 | 22.0 | 2.8 | 509.3 | 157.2 |
| L5 | 187.8 | 202.1 | 199.4 | Excluded | 198.6 | 197.0 | 6.3 | 3.2 | 127.3 | 154.7 |
| L6 | 48.4 | 51.8 | 47.6 | 58.1 | 46.8 | 50.5 | 4.6 | 9.2 | 31.8 | 158.8 |
| L7 | 9.6 | 8.2 | 10.3 | 16.2 | 12.0 | 11.3 | 3.1 | 27.4 | 8.0 | 141.5 |
| HGF (62) | | | | | | | | | | |
| L1 | 55543.0 | 49431.7 | 51509.4 | 58031.0 | 53757.5 | 53654.5 | 3360.2 | 6.3 | 53654.5 | 100.0 |
| L2 | 10850.8 | 9761.0 | 10890.6 | 12128.0 | 10823.2 | 10890.6 | 838.6 | 7.7 | 13413.6 | 81.2 |
| L3 | 3038.3 | 2877.1 | Excluded | 3055.5 | 3028.9 | 2999.9 | 82.6 | 2.8 | 3353.4 | 89.5 |
| L4 | 754.8 | 758.1 | 752.8 | 764.9 | 833.4 | 772.8 | 34.2 | 4.4 | 838.4 | 92.2 |
| L5 | 186.7 | 190.1 | 199.3 | Excluded | 194.7 | 192.7 | 5.5 | 2.8 | 209.6 | 91.9 |
| L6 | 44.0 | 45.3 | 51.5 | 63.1 | 48.0 | 50.4 | 7.6 | 15.2 | 52.4 | 96.2 |
| L7 | 10.7 | 10.6 | 12.3 | 19.4 | 11.5 | 12.9 | 3.7 | 28.7 | 13.1 | 98.5 |

TABLE 6-continued

| | Day 1 | Day 2 | Day 3 | Day 4 | Day 5 | Mean | SD | % CV | Calculcated | Recovery (%) |
|---|---|---|---|---|---|---|---|---|---|---|
| sIL-6Ra (19) | | | | | | | | | | |
| L2 | 8292.5 | 8067.7 | 8630.6 | 8308.1 | 8809.6 | 8421.7 | 295.4 | 3.5 | 8421.7 | 100.0 |
| L3 | 1759.7 | 2043.3 | Excluded | 1641.0 | 2076.8 | 1880.2 | 213.7 | 11.4 | 2105.4 | 89.3 |
| L4 | 457.1 | 483.4 | 493.1 | 425.2 | 501.0 | 472.0 | 30.9 | 6.6 | 526.4 | 89.7 |
| L5 | 106.7 | 118.2 | 113.8 | Excluded | 114.4 | 113.3 | 4.8 | 4.2 | 131.6 | 86.1 |
| L6 | 25.9 | 26.8 | 25.8 | 30.4 | 28.6 | 27.5 | 2.0 | 7.2 | 32.9 | 83.6 |
| L7 | 5.4 | 5.8 | 6.8 | 9.7 | 7.1 | 7.0 | 1.7 | 24.2 | 8.2 | 84.7 |
| Leptin (78) | | | | | | | | | | |
| L1 | 144237.0 | 112564.6 | 108209.6 | 106556.2 | 123811.6 | 119075.8 | 15594.8 | 13.1 | 119075.8 | 100.0 |
| L2 | 38093.8 | 36422.5 | 39031.6 | 32718.3 | 39886.6 | 37230.5 | 2830.9 | 7.6 | 29768.9 | 125.1 |
| L3 | 11601.6 | 10083.0 | Excluded | 8450.5 | 10125.9 | 10065.3 | 1287.4 | 12.8 | 7442.2 | 135.2 |
| L4 | 2622.5 | 2447.8 | 2341.4 | 1926.0 | 2446.7 | 2356.9 | 261.2 | 11.1 | 1860.6 | 126.7 |
| L5 | 516.0 | 538.2 | 520.7 | Excluded | 539.5 | 528.6 | 12.0 | 2.3 | 465.1 | 113.6 |
| L6 | 105.6 | 122.7 | 130.9 | 119.0 | 123.4 | 120.3 | 9.3 | 7.7 | 116.3 | 103.4 |
| L7 | 24.0 | 32.1 | 35.0 | 31.5 | 34.9 | 31.5 | 4.5 | 14.3 | 29.1 | 108.3 |
| Osteopontin (77) | | | | | | | | | | |
| L1 | 160984.7 | 165424.9 | 166260.5 | 201494.8 | 177840.9 | 174401.2 | 16376.4 | 9.4 | 174401.2 | 100.0 |
| L2 | 79920.9 | 88310.7 | 89324.9 | 92611.1 | 85371.3 | 87107.8 | 4778.0 | 5.5 | 43600.3 | 199.8 |
| L3 | 19610.5 | 21588.9 | Excluded | 20197.2 | 22236.2 | 20908.2 | 1213.2 | 5.8 | 10900.1 | 191.8 |
| L4 | 4922.2 | 4813.5 | 5285.2 | 4706.9 | 5379.1 | 5021.0 | 295.6 | 5.9 | 2725.0 | 184.3 |
| L5 | 1136.7 | 1201.1 | 1307.0 | Excluded | 1214.0 | 1214.7 | 70.2 | 5.8 | 681.3 | 178.3 |
| L6 | 302.8 | 327.0 | 324.6 | 305.0 | 341.9 | 320.2 | 16.4 | 5.1 | 170.3 | 188.0 |
| PDGF-AB/BB (47) | | | | | | | | | | |
| L1 | 47772.2 | 34658.8 | 48023.0 | 42570.5 | 40804.3 | 42765.8 | 5529.7 | 12.9 | 42765.8 | 100.0 |
| L2 | 12908.9 | 10914.9 | 12460.0 | 12686.6 | 12223.6 | 12238.8 | 782.9 | 6.4 | 10691.4 | 114.5 |
| L3 | 3086.8 | 3224.9 | Excluded | 2651.1 | 2856.5 | 2954.8 | 253.2 | 8.6 | 2672.9 | 110.5 |
| L4 | 822.3 | 862.2 | 825.7 | 736.0 | 806.6 | 810.5 | 46.4 | 5.7 | 668.2 | 121.3 |
| L5 | 170.0 | 218.4 | 188.4 | Excluded | 185.9 | 190.7 | 20.2 | 10.6 | 167.1 | 114.1 |
| L6 | 30.0 | 50.8 | 46.4 | 54.6 | 38.4 | 44.0 | 9.9 | 22.5 | 41.8 | 105.4 |
| L7 | 7.2 | 14.4 | 10.6 | 15.9 | 10.4 | 11.7 | 3.5 | 29.7 | 10.4 | 111.9 |
| PECAM-1 (46) | | | | | | | | | | |
| L1 | 215657.8 | 193572.8 | 216427.6 | 196725.7 | 216117.0 | 207700.2 | 11514.7 | 5.5 | 207700.2 | 100.0 |
| L2 | 64897.0 | 57081.9 | 67210.1 | 61177.9 | 61298.7 | 62333.1 | 3883.9 | 6.2 | 51925.0 | 120.0 |
| L3 | 15470.9 | 16028.5 | Excluded | 14360.1 | 16097.6 | 15489.3 | 803.4 | 5.2 | 12981.3 | 119.3 |
| L4 | 3584.6 | 3608.8 | 3820.9 | 3283.2 | 3664.6 | 3592.4 | 195.8 | 5.5 | 3245.3 | 110.7 |
| L5 | 760.2 | 824.7 | 922.8 | Excluded | 830.1 | 834.4 | 66.9 | 8.0 | 811.3 | 102.8 |
| L6 | 177.9 | 208.7 | 237.0 | 211.0 | 189.9 | 204.9 | 22.6 | 11.0 | 202.8 | 101.0 |
| Prolactin (52) | | | | | | | | | | |
| L1 | 266909.9 | 236657.1 | 328889.0 | 311790.8 | 325131.4 | 293875.7 | 40388.5 | 13.7 | 293875.7 | 100.0 |
| L2 | 67132.5 | 67720.9 | 81184.3 | 79780.2 | 80496.2 | 75262.8 | 7173.6 | 9.5 | 73468.9 | 102.4 |
| L3 | 17659.5 | 20183.8 | Excluded | 17672.5 | 19117.2 | 18658.3 | 1225.7 | 6.6 | 18367.2 | 101.6 |
| L4 | 4510.3 | 5001.1 | 5165.0 | 4712.8 | 4857.4 | 4849.3 | 253.2 | 5.2 | 4591.8 | 105.6 |
| L5 | 1003.6 | 1223.9 | 1156.9 | Excluded | 1212.4 | 1149.2 | 101.5 | 8.8 | 1148.0 | 100.1 |
| L6 | 211.1 | 243.6 | 286.2 | 393.3 | 264.8 | 279.8 | 69.2 | 24.7 | 287.0 | 97.5 |
| L7 | 63.1 | 68.3 | 38.6 | 159.5 | 48.6 | 75.6 | 48.3 | 63.9 | 71.7 | 105.4 |
| SCF (65) | | | | | | | | | | |
| L1 | 60329.9 | 54420.4 | 56276.6 | 54321.0 | 56272.7 | 56324.1 | 2433.5 | 4.3 | 56324.1 | 100.0 |
| L2 | 11016.1 | 12493.6 | 13258.5 | 13083.5 | 12319.2 | 12434.2 | 884.4 | 7.1 | 14081.0 | 88.3 |
| L3 | 2937.6 | 3138.5 | Excluded | 2697.5 | 3125.5 | 2974.8 | 206.4 | 6.9 | 3520.3 | 84.5 |
| L4 | 745.4 | 773.1 | 766.5 | 706.1 | 783.6 | 754.9 | 30.7 | 4.1 | 880.1 | 85.8 |
| L5 | 163.3 | 192.4 | 184.6 | Excluded | 182.5 | 180.7 | 12.4 | 6.9 | 220.0 | 82.1 |
| L6 | 38.3 | 42.0 | 41.5 | 58.5 | 43.3 | 44.7 | 7.9 | 17.7 | 55.0 | 81.3 |
| L7 | 9.5 | 12.4 | 10.4 | 12.3 | 10.0 | 10.9 | 1.3 | 12.1 | 13.8 | 79.4 |
| sTIE-2 (64) | | | | | | | | | | |
| L1 | 170902.0 | 150892.2 | 152000.8 | 161237.2 | 143129.4 | 155632.3 | 10683.6 | 6.9 | 155632.3 | 100.0 |
| L2 | 72585.5 | 62033.9 | 70561.7 | 69443.4 | 67314.0 | 68387.7 | 4030.7 | 5.9 | 38908.1 | 175.8 |
| L3 | 19092.2 | 18817.1 | Excluded | 17416.0 | 19379.0 | 18676.1 | 870.8 | 4.7 | 9727.0 | 192.0 |
| L4 | 4809.1 | 5016.3 | 5044.9 | 4844.3 | 5101.5 | 4963.2 | 128.9 | 2.6 | 2431.8 | 204.1 |
| L5 | 1134.5 | 1255.6 | 1154.0 | Excluded | 1169.6 | 1178.4 | 53.4 | 4.5 | 607.9 | 193.8 |
| L6 | 244.9 | 319.2 | 317.2 | 406.9 | 274.2 | 312.5 | 61.3 | 19.6 | 152.0 | 205.6 |
| L7 | 53.6 | 107.1 | 62.6 | 179.6 | 74.3 | 95.4 | 51.2 | 53.7 | 38.0 | 251.2 |
| sVEGFR-1 (76) | | | | | | | | | | |
| L1 | 17205.6 | 11938.6 | 15333.3 | 18656.4 | 14823.0 | 15591.4 | 2549.5 | 16.4 | 15591.4 | 100.0 |
| L2 | 5389.6 | 4779.9 | 5835.4 | 5940.0 | 4739.4 | 5336.9 | 566.2 | 10.6 | 3897.8 | 136.9 |
| L3 | 1718.4 | 1692.3 | Excluded | 1801.9 | 1520.8 | 1683.3 | 118.0 | 7.0 | 974.5 | 172.7 |

TABLE 6-continued

|  | Day 1 | Day 2 | Day 3 | Day 4 | Day 5 | Mean | SD | % CV | Calculcated | Recovery (%) |
|---|---|---|---|---|---|---|---|---|---|---|
| L4 | 463.5 | 487.9 | 492.5 | 499.6 | 452.2 | 479.1 | 20.3 | 4.2 | 243.6 | 196.7 |
| L5 | 104.3 | 100.0 | 91.5 | Excluded | 110.6 | 101.6 | 8.0 | 7.9 | 60.9 | 166.8 |
| L6 | 17.1 | 21.1 | 13.2 | 38.5 | 21.0 | 22.2 | 9.7 | 43.7 | 15.2 | 145.8 |
| sVEGFR-2 (45) | | | | | | | | | | |
| L1 | 150145.8 | 125294.1 | 123188.5 | 145969.2 | 134153.4 | 135750.2 | 12055.4 | 8.9 | 135750.2 | 100.0 |
| L2 | 74657.6 | 70995.3 | 75815.4 | 77120.4 | 71769.7 | 74071.7 | 2619.2 | 3.5 | 33937.5 | 218.3 |
| L3 | 18055.5 | 19304.7 | Excluded | 18249.4 | 18659.4 | 18567.2 | 552.4 | 3.0 | 8484.4 | 218.8 |
| L4 | 4476.6 | 4926.5 | 4899.2 | 4451.5 | 4886.9 | 4728.1 | 241.7 | 5.1 | 2121.1 | 222.9 |
| L5 | 980.7 | 1156.5 | 1160.8 | Excluded | 1137.3 | 1108.8 | 86.0 | 7.8 | 530.3 | 209.1 |
| L6 | 256.4 | 256.7 | 250.0 | 306.7 | 275.4 | 269.0 | 23.1 | 8.6 | 132.6 | 202.9 |
| L7 | 56.3 | 62.6 | 59.6 | 94.8 | 75.2 | 69.7 | 15.7 | 22.6 | 33.1 | 210.3 |

Integrated Analyses of Proteins and their Glycans in a Magnetic Bead-Based Multiplex Assay Format The differential detection of glycosylated proteins is important to human health because changes in glycosylation are associated with many human diseases (1-6). Carbohydrate cancer antigen CA19-9 is increased in patients with colorectal cancer (5). Prostate-specific antigen, the biomarker for early detection of prostate cancer, has decreased sialylation in the serum of patients with prostate cancer (6). In patients with liver diseases, glycoproteins with increased fucosylation have been reported as candidate biomarkers (4, 7-9). Detection of disease-related changes of glycan structures in proteins provides biomarkers with better disease specificity. Such an improvement has been demonstrated by α-fetoprotein (AFP) (2), a marker for hepatocellular carcinoma, and AFP-L3, a core-fucosylated glycoform of AFP (10). Because the enzyme fucosyltransferase Fut8 is overexpressed, detection of AFP-L3 provides better diagnostic specificity for hepatocellular carcinoma than detection of AFP alone (11).

For analyses of glycoproteins and their glycoforms, analytical methods integrating glycoprotein quantification and glycan detection are desired. Mass spectrometry (MS)-based approaches for the integrated analyses are emerging (12-14). Because the MS-based approaches usually require glycoproteins in relatively large quantities (nanograms to micrograms), they are impractical for routine analyses of well-annotated clinical samples that often have limited quantities. Multiplex magnetic bead-based immunoassays have been widely used for routine analyses of well-annotated clinical samples for biomarker discovery and validation for several reasons. These immunoassays require little sample preparation and are easy to perform. The assays are high throughput and can analyze a large number of samples in a short period of time. Lastly, the multiplex ability of these assays for simultaneous measurement of proteins in a single sample results in substantial saving of samples. Building on these advantages, we developed a multiplex magnetic bead-based system that integrates protein quantification with glycan detection.

Tissue inhibitor of metallopeptidase 1 (TIMP-1), tissue plasminogen activator (tPA), membrane metallo-endopeptidase (MME), and dipeptidyl peptidase-IV (DPP-4) are glycoproteins previously discovered using MS-based proteomic analyses as candidate biomarkers in prostate cancer (15-16). Glycan structures of TIMP-1 from cell lines and plasma of patients with cancer have been well characterized and are mostly core fucosylated bi-, tri-, or tetraantennary (17-18). Glycan structures of DPP-4, MME, and tPA are less well characterized than those of TIMP-1. Although glycan profiles of MME were evaluated by lectin microarray (19), the detailed glycan structures remain to be determined Glycan structures of human recombinant tPA produced by Chinese hamster ovary cells have been reported to be core fucosylated and mono-, di-, and trisialylated (20-21). Glycan structures of rat kidney DPP-4 are a mixture of high-mannose-type sugar chains and mono-, bi-, tri-, and tetraantennary complex-type sugar chains (22-23).

Despite the previously published information on the glycan structures of TIMP-1, DPP-4, MME, and tPA, whether glycoforms of these proteins could serve as biomarkers to distinguish aggressive (AG) and nonaggressive (NAG) prostate cancers remains to be determined. In this study, we applied a multiplex integrated system to analyze TIMP-1, tPA, MME, and DPP-4 in tissues, as well as their glycoforms, as candidate biomarkers for AG prostate cancer. Molecular mechanisms of aberrant glycosylation have indicated increased β1-6 branching of N-glycans and α1-2 fucosylation in prostate cancer progression. Increases in β1-6 branching of N-glycans, which result from overexpression of GlcNAc-TV (UDP-GlcNAc:Manα1-6Manβ-R β1-6-N-acetylglucos-aminyltransferase V) in cancer progression (24), have been reported to be associated with lymph node metastasis in breast carcinoma and promotion of tumor growth and metastasis in many cancers (25-27). Fucosylation in cancer progression has been best studied in hepatocellular carcinoma, which results in overexpression of the enzyme fucosyltransferase Fut8 (11). Recently, quantitative real-time reverse-transcription PCR analysis of glycosyltransferases in normal tissue, tissue from prostate cancer patients, and prostate cancer cell lines indicated that cancer cells have higher mRNA concentrations of Fut1 [fucosyltransferase 1 (galactoside 2-alpha-L-fucosyltransferase, H blood group)], which encodes fucosyltransferase, an enzyme responsible for α1-2 fucosylation (28). Because of the indications of increased β1-6 branching of N-glycans and α1-2 fucosylation as aberrant glycosylation in prostate cancer progression, we used the lectins phytohemagglutinin-L (PHA-L) and Ulex europaeus agglutinin (UEA), which preferentially recognize the β1-6 branched N-glycans and the α1-2 fucosylated N-glycans, respectively, in the multiplex lectin immunosorbent assays (LISAs).

Materials and Methods

Reagents and Cell Culture.

We purchased DPP-4, MME, and TIMP-1 capture and biotinylated detection antibodies and their recombinant proteins from R&D Systems. tPA capture and biotinylated detection antibodies were from Abcam. Detailed information for the antibodies and recombinant proteins are described below. Magnetic beads, amine coupling kits, and cytokine assay kits were purchased from Bio-Rad Laboratories. Biotinylated UEA, PHA-L, *Aleuria aurantia* lectin (AAL), and *Vicia villosa* agglutinin (VVA) were from Vector Laboratories. Cells from the human prostate cancer cell lines PC3 and DU145 were purchased from ATCC and were cultured according to the manufacturer's instructions.

Clinical Samples.

The 29 tissue samples analyzed in this study were from men with prostate cancer. Informed consent was obtained under protocols that were institutional review board approved and Health Insurance Portability and Accountability Act compliant. The tissue samples surgically removed were flash frozen, embedded in OCT (optimal cutting temperature) media, and stored at −80° C. till cryostat microdissection. Twenty-one of the tissue samples were NAG prostate cancer defined by their pathological Gleason scores of 6; 8 samples were AG prostate cancer defined by their pathological Gleason scores of 8, 9, or 10. Both NAG and AG prostate cancer tissues were cryostatically microdissected from primary tissues to enrich the tumor content (29). The microdissected tissues were then lysed in radioimmunoprecipitation assay buffer on ice. We determined protein concentrations of the lysed tissue samples by using the bicinchoninic acid assay (Thermo Scientific) normalized to 1 mg/mL. The tissue samples were further diluted 50 times with PBS (13.7 mmol/L NaCl, 2.7 mmol/L KCl, 10 mmol/L $Na_2HPO_4$, 2.0 mmol/L $KH_2PO_4$, pH 7.4) to a protein concentration of 20 µg/mL and stored at −80° C. until use.

Magnetic Bead-Based Integrated System for Timp-1.

The TIMP-1 capture antibody was coupled to magnetic beads with the Bio-Rad amine-coupling kit used according to the manufacturer's instructions. Detailed procedures of the TIMP-1 immunoassays are described in the online Data Supplement. For TIMP-1 LISAs, 2 µg/mL biotinylated TIMP-1 detection antibody used in the immunoassay was replaced with 20 µg/mL of biotinylated UEA, PHA-L, AAL, or VVA. The TIMP-1 immunoassay and TIMP-1 LISAs were used to analyze TIMP1 in the culture media of PC3 and DU145 cells. Four samples were prepared by 4-fold serial dilutions of the neat culture media. We established a calibration curve using 8 calibrators of 100, 25, 6.25, 1.56, 0.39, 0.1, 0.025, and 0 ng/mL of TIMP-1 and used this curve to determine TIMP-1 protein concentrations.

Multiplex Integrated System for Tpa, Dpp-4, Mme, and Timp-1.

As done for TIMP-1, we developed single immunoassays for tPA, DPP-4, and MME. The magnetic beads used for coupling the detection antibodies could be distinguished by their distinctive emission fluorescence and therefore could be mixed together. For the multiplex immunoassay, the beads used for capture and the antibodies for detection were prepared by mixing the 2500 couple beads and the detection antibodies used in the single assays. Single-antigen and single-detection cross-reactivity studies were performed to evaluate the specificity of the capture and detection antibodies. The single-antigen study was conducted by testing the individual antigen in the presence of multiplexed capture beads and detection antibodies. The single-detection study was conducted by testing the individual detection antibodies in the presence of multiplexed antigens and capture beads. For the multiplex LISAs, the same mixture of beads used in the multiplex immunoassay was used for capture, and 20 µg/mL of biotinylated UEA, PHA-L, AAL, or VVA was used for detection.

Six serum samples prepared by supplementing a pooled serum (Sigma-Aldrich) with recombinant TIMP-1, tPA, DPP-4, and MME were used for method comparisons of the multiplex and single immunoassays. For the multiplex immunoassay, we established 1 calibration curve using 8 calibrators of 100, 25, 6.25, 1.56, 0.39, 0.1, 0.025, and 0 ng/mL recombinant tPA, MME, DPP-4, and TIMP-1, respectively. For the single immunoassays, 4 calibration curves were established using 8 calibrators of 100, 25, 6.25, 1.56, 0.39, 0.1, 0.025, and 0 ng/mL of recombinant tPA, MME, DPP-4, or TIMP-1. The same calibrators were used for comparisons of the multiplex and single LISAs.

Data Analysis.

We established calibration curves for protein quantification using the 5-parameter nonlinear regression model in Bio-Plex Manager™ 6.0. Protein concentrations were calculated by using the calibration curves and reported by Bio-Plex Manager™ 6.0. We used Graphpad Prism 5.04 for linear regression and statistical analysis.

Antibodies and Recombinant Proteins.

Human DPP4 rat monoclonal IgG2A antibody (Catalog #MAB1180) was used for capture, biotinylated human DPP-4 polyclonal goat IgG antibody (Catalog # BAF1180) was used for detection; and mouse myeloma cell line, NS0-derived human recombinant DPP-4 (Catalog #1180-SE-010) was used as standard. Human MME goat polyclonal IgG antibody (Catalog #MAB1182) was used for capture; biotinylated human MME goat polyclonal IgG antibody was used for detection (Catalog #BAF1182), and Chinese Hamster ovary cell line, CHO-derived human recombinant MME (Catalog#1182-ZNC-010) was used as standard. Human TIMP1 mouse monoclonal IgG2B antibody (Catalog #MAB970, clone #63515) was used for capture; biotinylated human TIMP1 goat polyclonal IgG antibody (Catalog # BAF970) was used for detection; and mouse myeloma cell line, NS0-derived human recombinant TIMP1 (Catalog #970-TM-010) was used as standard. Human tPA mouse monoclonal antibody (Catalog # ab82249) used for capture, biotinylated human tPA rabbit polyclonal IgG antibody (Catalog #ab28208) used for detection, and Chinese Hamster ovary cell line, CHO-derived human recombinant tPA protein (Catalog #ab92637) used as standard were purchased from Abcam (Cambridge, Mass.).

TIMP-1 Immunoassay.

After coupling, beads were counted and validated to ensure binding of capture antibody to the beads using biotinylated goat anti-mouse IgG antibodies (Sigma-Aldrich, St. Louis, Mo.) before they were stored in the storage buffer at 4° C. BioRad Cytokine Assay Kit was used for development of TIMP-1 immunoassay and TIMP-1 LISAs. For TIMP-1 immunoassay, 2500 coupled beads were incubated with 50 µL of a sample diluted in the Sample Diluent (provided in the Cytokine Assay Kit). After 1-hour incubation at room temperature, the beads were washed and incubated with 25 µL of 2 µg/mL biotinylated TIMP-1 detection antibody diluted in the Detection Antibody Diluent (provided in the Cytokine Assay Kit) at room temperature for 30 minutes. Then the beads were washed again and incubated with 50 µL of 2 µg/mL streptavidin-phycoerythrin diluted in the Assay Buffer at room temperature for 10 minutes before analysis using the Bioplex 200 System. For TIMP-1 LISAs, 2 µg/mL biotinylated TIMP-1 detection antibody used in the immunoassay was replaced with 20 µg/mL of biotinylated UEA, PHA-L, AAL, or VVA.

Analyses of the Prostate Tissue Specimens by the Multiplex Integrated System.

Fifteen micro liters of the prostate tissue specimens were further diluted 25 times using PBS+1% BSA buffer to 375 µL prior to analyses. For detection of proteins, 50 µL of diluted specimens were incubated with the mixture of the coupled beads for 1 hour at room temperature. After incubation, the beads were washed and incubated with the mixture of detection antibodies diluted in the Detection Antibody Diluent at room temperature for 30 minutes. Then the beads were washed again and incubated with 50 µL of 2 µg/mL streptavidin-phycoerythrin diluted in the Assay Buffer at room temperature for 10 minutes before analysis using the Bioplex 200 System. For detection of glycans, the mixture of detection antibodies used in the multiplex immunoassay was replaced with 20 µg/mL of biotinylated UEA or PHA-L. Duplicate measurement was performed for each specimen.

Results

Figure 2:
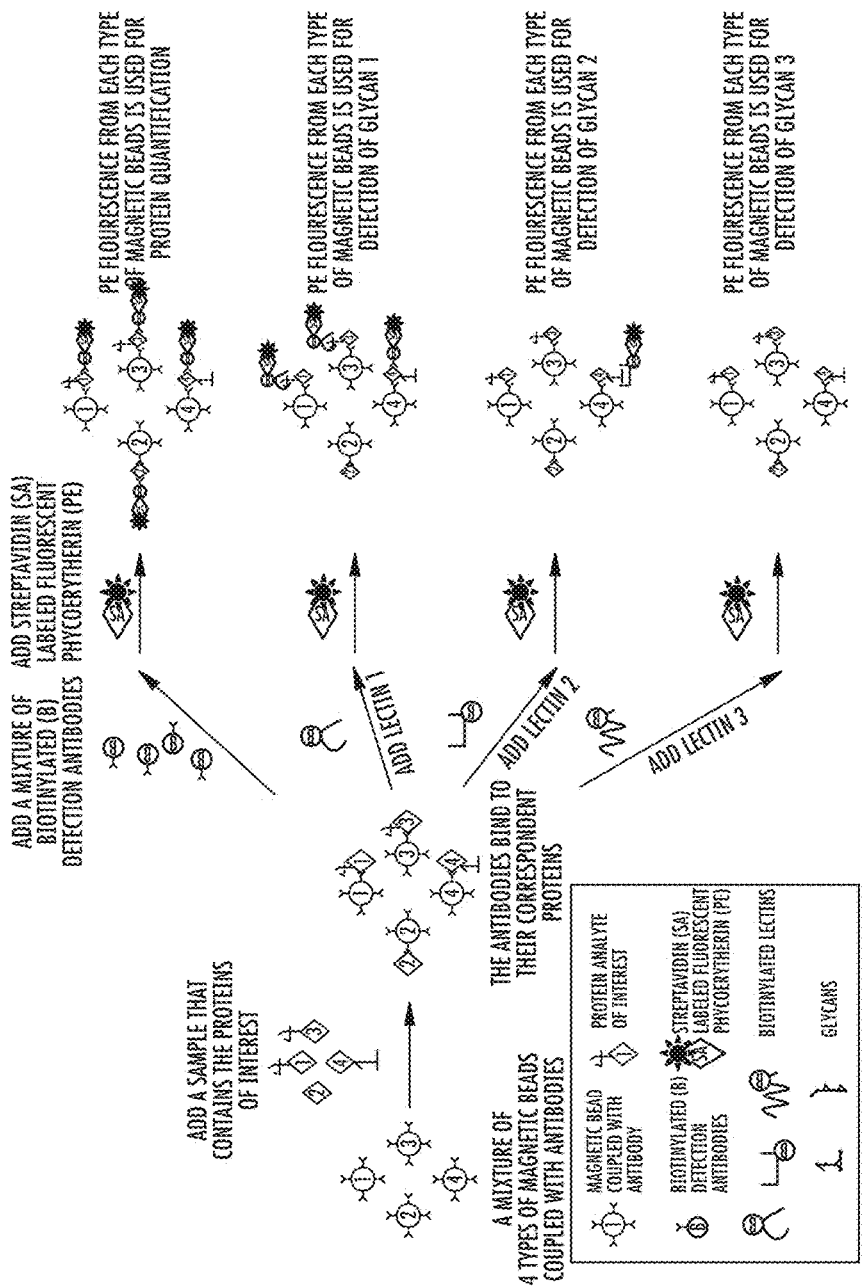
FIG. 2. The magnetic bead-based system that integrates protein quantification with glycan detection. For protein quantification, magnetic beads coupled with antibodies were used for capturing proteins of interest, and biotinylated antibodies in combination with streptavidin-labeled phycoerythrin were used for detection. Multiplex glycan detection was achieved by running the assay multiple times, each with a different lectin.
Figure 5A:
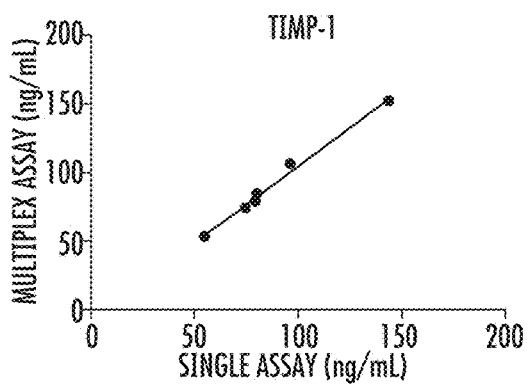
FIG. 5. Comparison of the multiplex immunoassays and single immunoassays for measurement of DPP-4, TIMP-1, tPA, and MME in serum.
Figure 5B:
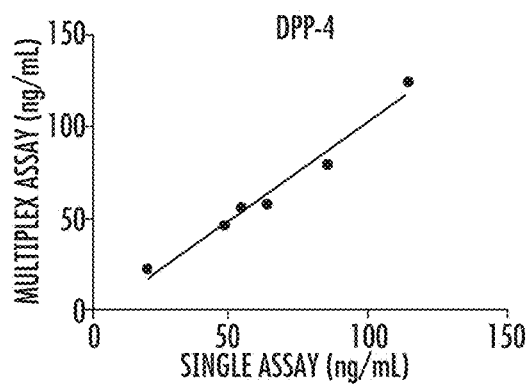
Figure 5C:
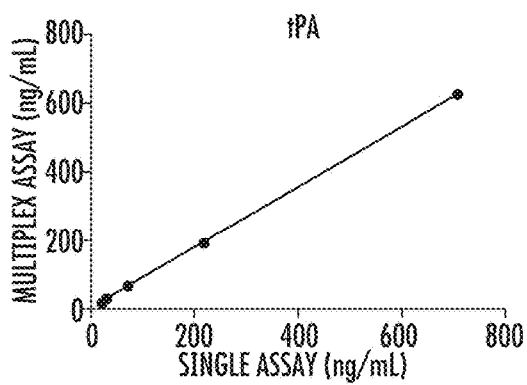
Figure 5D:
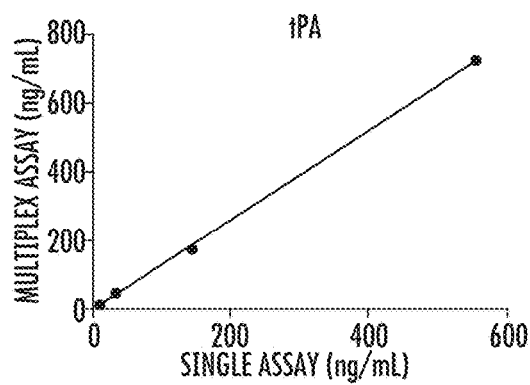
Figure 6C:
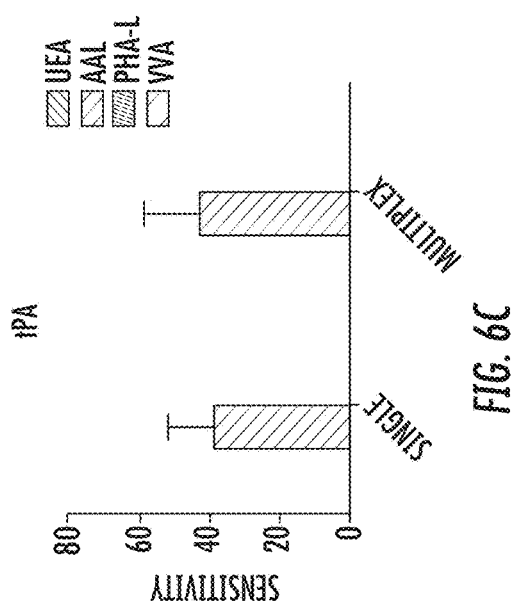
FIG. 6. Comparison of the multiplex LISAs and single LISAs for detection of glycan structures of recombinant TIMP-1, DPP-4, and tPA. The recombinant MME had few or no glycan structures associated with UEA, AAL, PHA-L, or VVA, and therefore its glycan profile was not included.
Figure 6B:
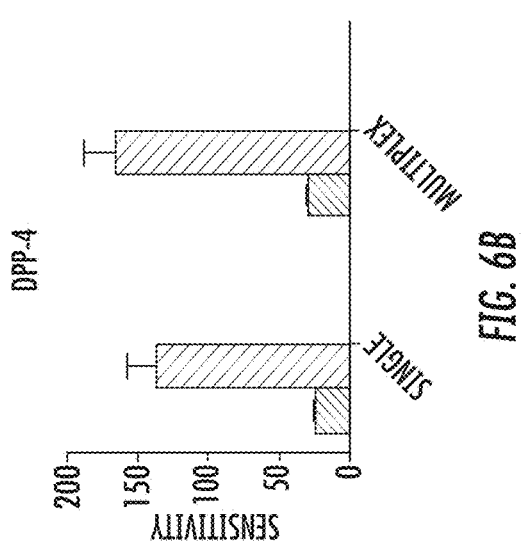
Figure 6A:
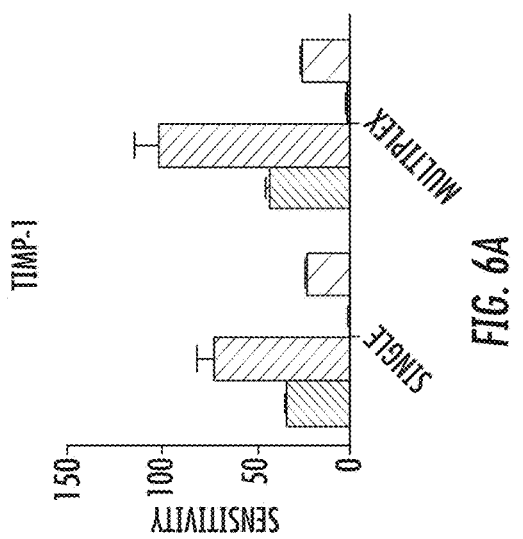

Magnetic beads with different internal fluorescent molecules and different emitted fluorescences (30) have been used for multiplex immunoassays that allow simultaneous measurement of multiple proteins in a single sample (31-32). Building on the multiplex-capability of magnetic beads, we developed a multiplex system integrating protein quantification and glycan detection (FIG. 2). This multiplex system used a standard multiplex immunoassay in which, for the detection of proteins, biotinylated detection antibodies were mixed together. However, for the detection of glycans, biotinylated lectins could not be mixed together because the same glycans could be found on different proteins. As a result, a single lectin was used for the detection of glycans on multiple proteins. This approach of using multiplexed detection of glycans in the magnetic bead system is similar to the detection of glycans in planar array systems such as antibody arrays (33). It is easier, however, to prepare the beads in bulk and reconfigure them to measure a new set of analytes (34), and this method involves fluid-phase kinetics, which is faster than the solid-phase kinetics of planar arrays and therefore has shorter reaction times (35).

Magnetic Bead-Based Integrated System for Timp-1.

Using TIMP-1 as a model protein, we demonstrated the feasibility of the integrated system for protein quantification and glycan detection. First, we developed a magnetic bead-based immunoassay for TIMP-1 protein. The calibration curve we established using recombinant TIMP-1 protein showed increased fluorescence signals with increasing TIMP-1 concentrations (FIG. 3A). Once the immunoassay was developed, we selected lectins for the development of TIMP-1 LISAs. Antibodies are glycoproteins, and it is known that in LISAs glycans on antibodies may bind to detection lectins, potentially causing high background noise (6, 33, 36). We tried 2 approaches to reduce the background: enzymatic digestion of the glycans off the antibodies and derivatization of the glycans with dipeptides to block glycan-lectin binding (37). Although both approaches were successful in reducing the background for the majority of detection lectins tested (FIGS. 8 and 9), the reduction was not universal. Through these experiments we also observed that not all of the lectins caused high background. We decided that instead of modifying glycans on the capture antibodies, we would circumvent the background issues by selecting the lectins to which the glycans on the antibodies did not bind. In addition, we determined the lectin-binding profile of recombinant TIMP-1 protein using tyramide signal amplification (36). Among the lectins to which TIMP-1 bound, we selected UEA, AAL, PHA-L, and VVA for the development of the LISAs.

Dose-response curves of TIMP-1 LISAs (FIG. 3, B-E) showed increased fluorescence signals in UEA, AAL, PHA-L, and VVA with increasing TIMP-1 concentrations. Sensitivity of the curves, calculated as changes of fluorescence intensity per TIMP-1 concentration, was used to establish the glycan profile of the recombinant TIMP-1 [FIG. 3F; mean (SD), 118 (7) for AAL; 44 (4) for VVA; 38 (1) for UEA; and 1.0 (0.2) for PHA-L]. They intercept of 25 in the TIMP-1 PHA-L assay (FIG. 3D) was likely due to the PHA-L-associated glycans on the TIMP-1 capture antibody. The glycan structures of the same recombinant TIMP-1 were analyzed by Thaysen-Andersen et al. (17), who showed, with the exception of a few core structures, predominantly core-fucosylated glycans to which AAL preferentially binds. This finding is consistent with the glycan profile established by the multiplex LISAs, as evidenced by the highest sensitivity TIMP-1 AAL assay of 118 (7). In agreement with Thaysen-Andersen et al. (17), the TIMP-1 LISAs showed that the recombinant TIMP-1 also contained terminal α1-2 fucosylated glycans associated with UEA, and tri- and tetraantennary core-fucosylated glycans associated with PHA-L.

Figure 10A:
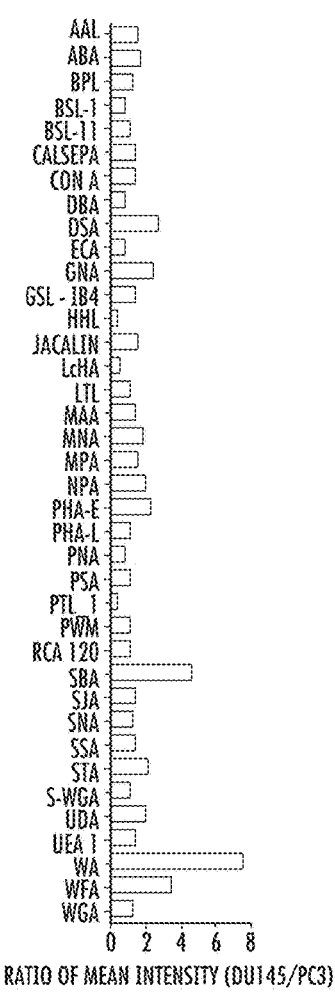
FIG. 10. Lectin profiles of TIMP-1 from PC3 and DU145 cell culture medium assessed by lectin microarray: (A) the ratios of mean fluorescence intensity for all the lectins (DU145/PC3) and (B) the mean fluorescence intensity for all the lectins.
Figure 10B:
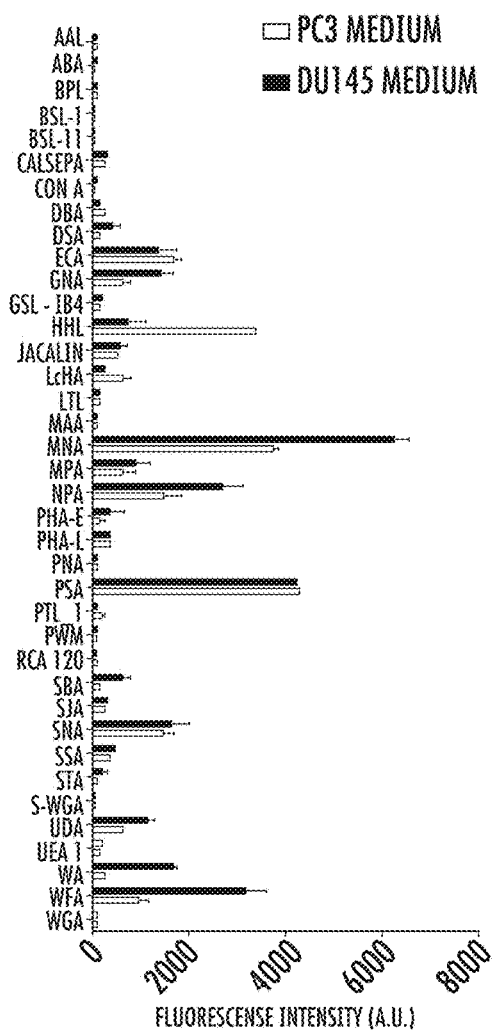
Figure 11:
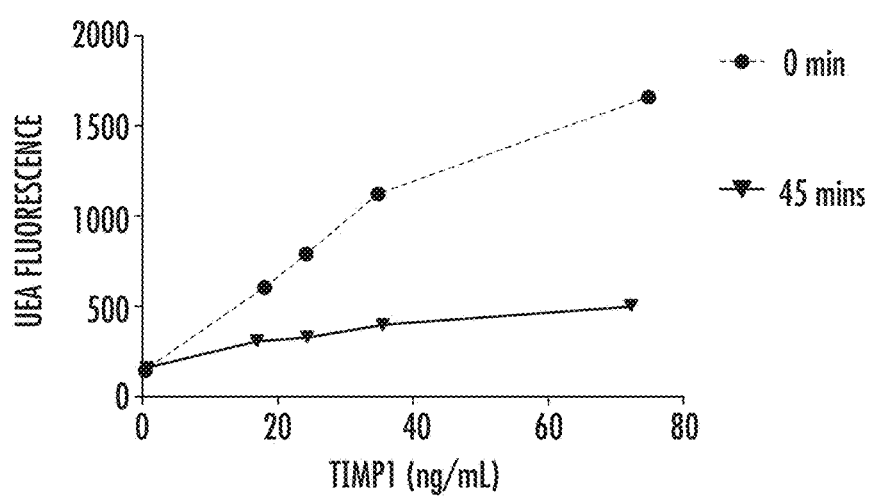
FIG. 11. Forty-five minute treatment decreased the fluorescence signals of TIMP1 measured by the UEA LISA compared to the controls (0 minute treatment) at various concentrations. Four microliter of the recombinant TIMP1 (10 µg/mL prepared in PBS+1% BSA buffer) was mixed with 4 µL of α1-2 fucosidase (Catalog# P0724, New England Biolabs, Ipswich, Mass.). The mixture (8 µL) was then diluted 5 times in the 32 µL of the Reaction buffer (50 mM Sodium Citrate, 100 mM Sodium Chloride, pH 6.0). For the 45 minutes treatment group, the mixture was incubated on shaker at 37° C. for 45 minutes before its being mixed into serum. Presence of large quantities of glycoproteins in serum would stop α1-2 fucosidase's enzymatic digestion of the TIMP1. For the 0 minute treatment group, the mixture of TIMP1 and α1-2 fucosidase was mixed into serum without the 37° C. incubation.

TIMP-1 was present in culture media of both PC3 and DU145 cells. Lectin microarray profiling indicated that TIMP-1 from these 2 sources had different glycans (FIG. 10). Consistent with the lectin microarray profiling results, TIMP-1 in DU145 medium showed more preferential binding to VVA than TIMP-1 in PC3 medium (shown in FIG. 4C; mean (SD) 31 (2) vs. 7.8 (0.7)). In FIGS. 4, A and B, AAL LISAs had background signals in the 300-400 range, which was likely due to the AAL-associated glycans on the TIMP-1 capture antibody (38). Using TIMP-1 from PC3 and DU145 cell culture media, we demonstrated that the magnetic bead-based system integrating protein quantification and glycan detection was capable of sensitive detection of proteins with differential glycan structures. To validate the lectin specificity of UEA toward α1-2-linked fucose, we used TIMP-1 as the model protein. Forty-five minute treatment of TIMP-1 with α1-2 fucosidase, an enzyme that hydrolyzes the α1-2 linked fucose that UEA preferentially recognizes, decreased the fluorescence signals of TIMP-1 measured by the UEA LISA at various concentrations compared to those without the treatment (FIG. 11). These results supported the specificity of UEA toward α1-2 linked fucose.

Multiplex Magnetic Bead-Based Integrated System for Tpa, Dpp-4, Mme, and Timp-1.

tPA, DPP-4, and MME, in addition to TIMP-1, were included as model proteins to demonstrate the feasibility of the integrated system for multiplexing. As done for TIMP-1, magnetic bead-based single immunoassays were developed for tPA, DPP-4, and MME. We examined the multiplex ability of the 4 single immunoassays by performing single-antigen and single-detection cross-reactivity studies, the results of which showed that the degree of cross-reactivity across the 4 immunoassays was <2% (FIG. 12). By mixing the magnetic beads and the detection antibodies used in the single assays, we developed the multiplex immunoassay and evaluated it by comparing it to the single immunoassays for measuring concentrations of tPA, DPP-4, MME, and TIMP-1 in serum samples. Linear regression analyses showed that the multiplex-to-single assay comparisons had slopes of 0.93 ($R^2$=0.91), 1.05 ($R^2$=0.97), 0.87 ($R^2$=1.00), and 1.30 ($R^2$=1.00) for DPP-4, TIMP-1, tPA, and MME, respectively (FIG. 5; also see Table 7). These results indicated that the multiplex immunoassay was comparable to the single assays in protein quantification.

TABLE 7

Linear regression analyses of the multiplex immunoassays and single immunoassays for DPP-4, TIMP-1, tPA and MME in serum.

|  | DPPIV | TIMP1 | tPA | MME |
| --- | --- | --- | --- | --- |
| N | 16 | 16 | 6 | 4 |
| Slope (95% CI) | 0.93 (0.76 to 1.09) | 1.05 (0.94 to 1.16) | 0.87 (0.86 to 0.88) | 1.30 (1.21 to 1.39) |
| Y-intercept (95% CI) | −0.6 (−12.6 to 11.5) | −1.1 (−11.4 to 9.3) | 1.4 (−1.1 to 3.8) | −5.5 (−30.3 to 19.3) |
| $R^2$ | 0.91 | 0.97 | 1.00 | 1.00 |

Next, by replacing the mixture of detection antibodies in the multiplex immunoassay with UEA, AAL, PHA-L, or VVA, we developed the multiplex LISAs. We found that, similar to TIMP-1 antibody, the capture antibodies for tPA, DPP-4, and MME did not cause background binding to the selected lectins. We evaluated the performances of these assays by comparing them to the performances of the respective single LISAs. Both the multiplex and single LISAs gave low signals for the recombinant MME (data not shown), indicating that the recombinant MME had few or no glycan structures that were associated with UEA, AAL, PHA-L, or VVA. The glycan profiles established for recombinant tPA, DPP-4, and TIMP-1 by the single assays were similar to the profiles established by the multiplex assays (FIG. 5). With the use of tPA, DPP-4, MME, and TIMP-1, the protein quantification and glycan detection on the multiplex integrated system was comparable to those of respective single immunoassays and single LISAs.

TABLE 8

Comparison of the sensitivity of the single and multiplex LISAs for measurement of glycan structures on recombinant TIMP-1, DPP-4, and tPA.

|  | TIMP1 | | | | DPPIV | | tPA |
| --- | --- | --- | --- | --- | --- | --- | --- |
| Sensitivity | UEA | AAL | PHA-L | VVA | UEA | AAL | AAL |
| Single | 34 ± 2 | 72 ± 09 | 1.0 ± 0.1 | 23.0 ± 0.3 | 25.3 ± 0.1 | 136 ± 22 | 38 ± 14 |
| Multiplex | 43 ± 3 | 101 ± 14 | 1.4 ± 0.2 | 26 ± 1 | 30.4 ± 0.3 | 164 ± 24 | 43 ± 15 |
| Statistically different? | No | No | No | No | No | No | No |

Application of the Multiplex Integrated Assay for Evaluation of Biomarkers in Aggressive Prostate Cancer.

We applied the system to analyze 21 NAG tissues and 8 AG prostate cancer tissues to evaluate tPA, DPP-4, MME, and TIMP-1 and their UEA- and PHA-L-associated glycoforms as biomarkers in AG prostate cancer. Because of the system's sensitive, multiplex, and integrated merits, we were able to carry out the evaluation using 300 ng of tissue samples. Neither tPA nor MME, nor their glycoforms detected by UEA or PHA-L, could be used to distinguish AG cancer (FIG. 7). tPA is a tissue type plasminogen activator. The primary role of tPA is the generation of plasmin for fibrinolysis in blood vessels (39). The initial study in which we discovered tPA as a candidate biomarker for prostate cancer was performed with serum samples (16). This use of serum might explain the lack of differences of tPA concentrations in AG and NAG prostate tissues. MME is a cell surface metallopeptidase. Expression of MME has been reported to be lost in several human tumors, including androgen-independent prostate cancer. Our data showed no difference in MME protein concentrations between AG and NAG prostate cancer tissues obtained from patients with androgen-dependent cancer.

Figure 7:
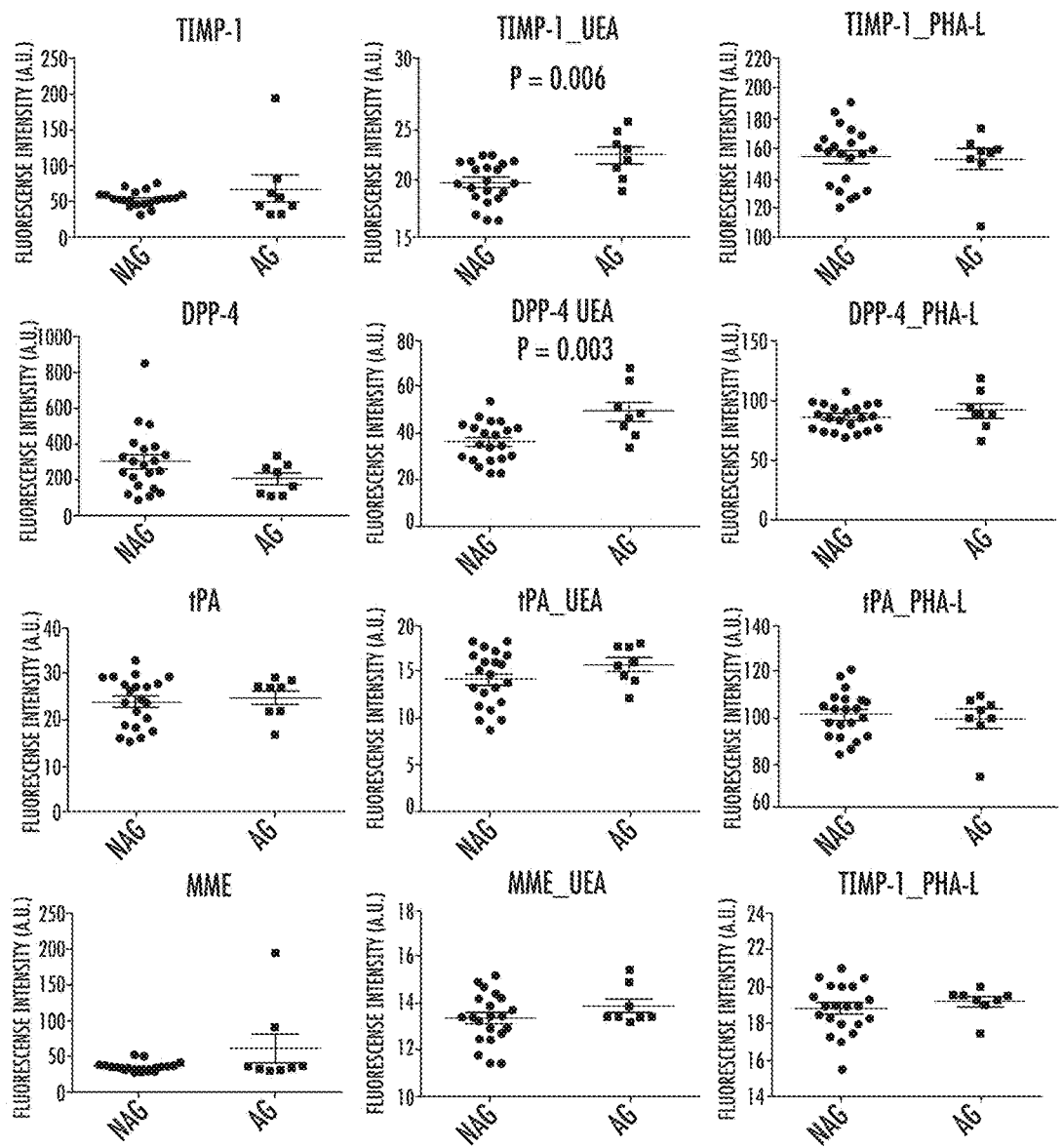
FIG. 7. Expression of TIMP-1, DPP-4, tPA, and MME and their UEA- and PHA-L-associated glycoforms in NAG and AG prostate cancer. A.U., arbitrary units.
Figure 8A:
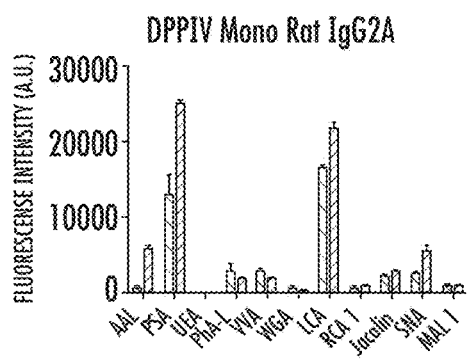
FIG. 8. Comparisons of background fluorescence signals detected by lectins before (red bars) and after (green bars) PNGase F treatment of the magnetic beads coupled with capture antibody of DPP-4 (A), MME (B), TIMP-1 (C), and tPA (D). For the PNGase F, the magnetic beads were incubated in the 1×G7 reaction buffer with PNGase F (New England BioLabs Inc., Ipswich, Mass.) at 37° C. for 1 hour.
Figure 8B:
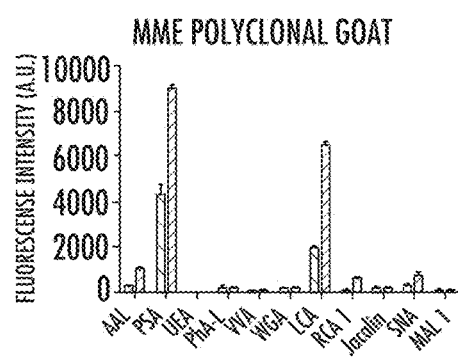
Figure 8C:
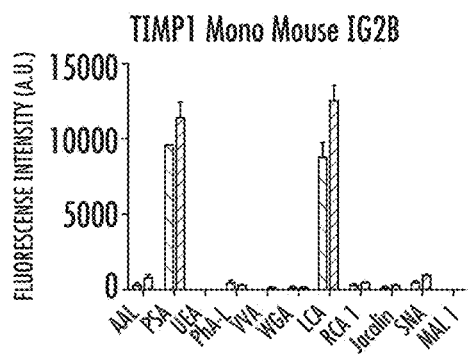
Figure 8D:
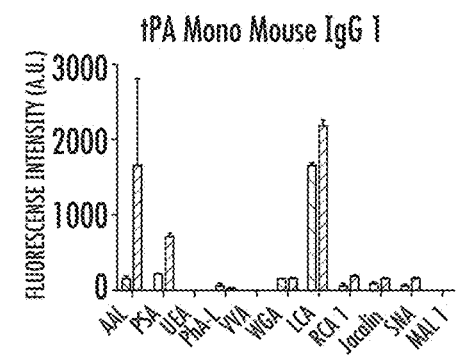
Figure 9A:
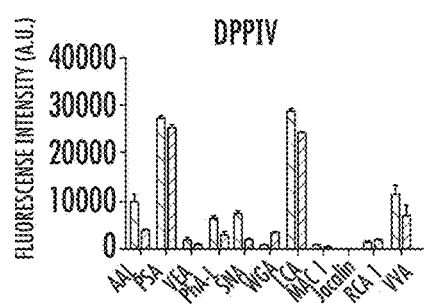
FIG. 9. Comparisons of background fluorescence signals detected by lectins before (red bars) and after (green bars) oxidation and dipeptide coupling treatment of the magnetic beads coupled with capture antibody of DPP-4 (A), MME (B), TIMP-1 (C), and tPA (D). For the oxidation and dipeptide coupling treatment, the beads were incubated with 10 µM sodium periodate (BioRad, Hercules, Calif.) in the oxidation buffer (150 mM sodium acetate, pH 5.5) in the dark at 4° C. for 30 minutes. Then the beads were washed and incubated with 1 mM MPBH (4-(4-N-Maleimidophenyl) butyric acid hydrazide-HCl) (Thermo Fisher Scientific, Rockford, Ill.) in the oxidation buffer at room temperature for 2 hours before incubation with 1 mM Cys-Gly dipeptide (Sigma-Aldrich, St Louis, Mo.) in the PBS+0.1% Tween buffer overnight.
Figure 9B:
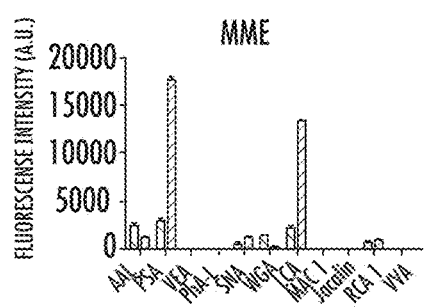
Figure 9C:
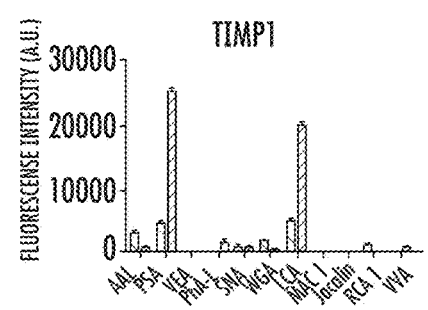
Figure 9D:
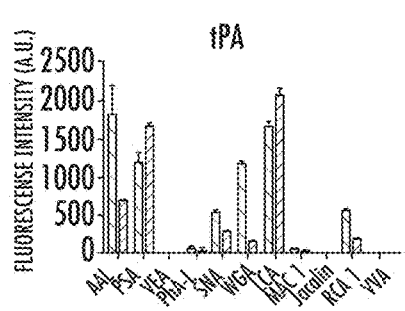
Figure 13A:
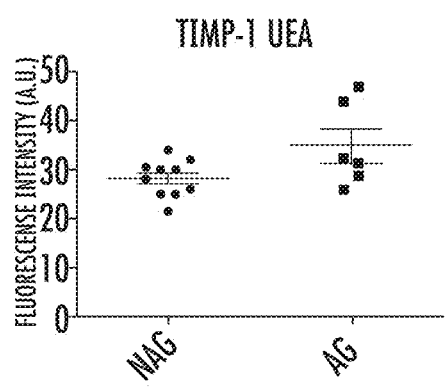
FIG. 13. Measurement of fucosylated TIMP-1 and DPP-4 by the multiplex UEA LISAs in 10 non-aggressive cancer and 6 aggressive cancer tissues.
Figure 13B:
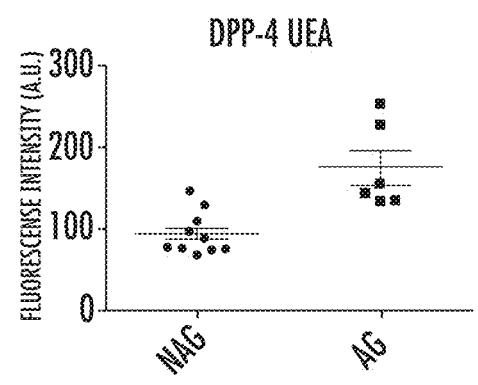
Figure 14A:
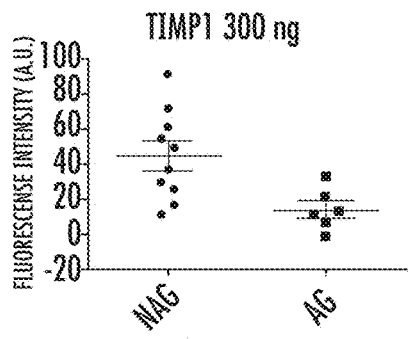
FIG. 14. Comparisons of the multiplex system in testing 300 nanograms and 1500 nanograms of 10 non-aggressive and 6 aggressive prostate cancer tissues.
Figure 14B:
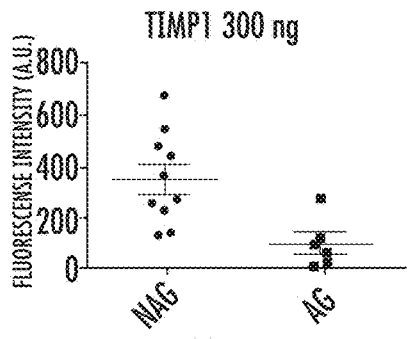
Figure 14C:
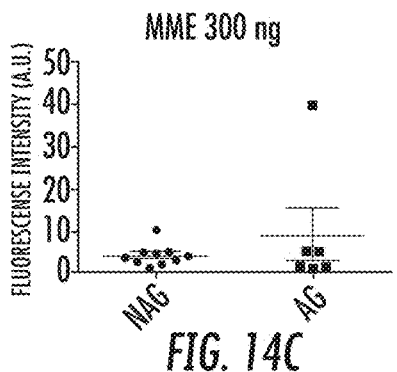
Figure 14D:
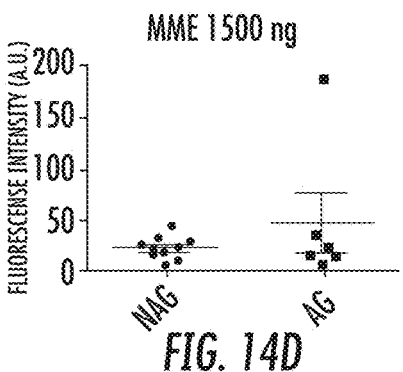
Figure 14E:
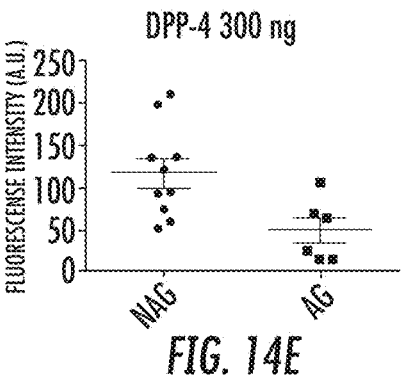
Figure 14F:
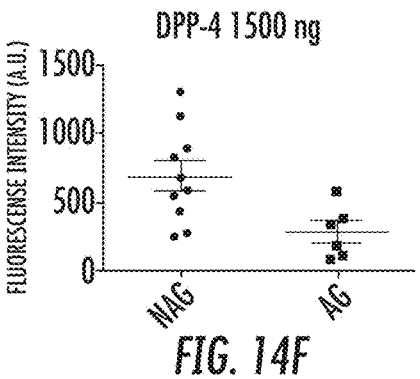
Figure 14G:
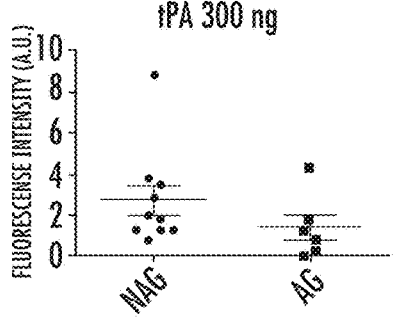
Figure 14H:
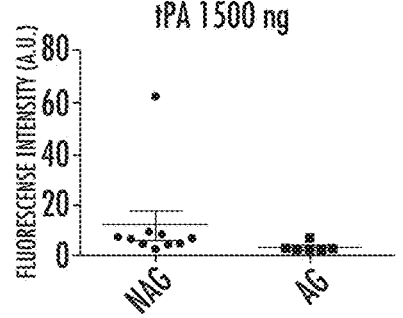

TIMP-1 has been shown to be decreased in prostate cancer tissues compared to noncancerous tissues (15). Our data showed that TIMP-1 protein concentrations did not differ between AG and NAG prostate cancer tissues. We were able to make the distinction, however, on the basis of the detection of UEA-associated fucosylated TIMP-1 (FIG. 7, P=0.006). DPP-4 is a cell surface serine protease associated with cancer suppression. DPP-4 also blocks fibroblast growth factor 2 signaling, altering the cell adhesion properties and malignant phenotype of prostate cancer cells (40). Unlike DPP-4, the detection of UEA-associated fucosylated DPP-4 showed a statistically significant (P=0.003) increase in AG cancer. A preliminary experiment that used 10 NAG and 6 AG prostate tissues (FIG. 13) showed the same patterns as those in FIG. 7, indicating that the changes observed were consistent. In addition, in this experiment we tested the amount of tissue to be used in the system and found that 1500 ng of tissue gave the same patterns for distinguishing AG and NAG prostate cancer as 300 ng of tissue (FIG. 14), highlighting the capabilities of this system in saving precious human samples.

Discussion

We were unable to distinguish between AG and NAG cancer with the detection of TIMP-1 and DPP-4, but we were able to make the distinction with the detection of fucosylated TIMP-1 and DPP-4. The results of the study highlight 2 merits of the multiplex and integrated system. First, because of its advantage in multiplexing, we used only 300 ng of tissue in protein for the validation and we saved quantities of the precious samples. Second, because of the advantages of integrated detection of glycoforms of proteins, we discovered that the use of fucosylated TIMP-1 and DPP-4 was associated with improved performance over the use of proteins in distinguishing AG and NAG prostate cancer.

Although recombinant proteins are widely used as standards in protein quantification, whether they are appropriate as standards for the detection of protein glycans, in our opinion, depends on the contexts in which they are being used. If used as standards for the quantification of protein glycoforms, such as the percentage of AFP-L3, highly purified single glycoforms of recombinant proteins should be used. The recombinant glycoproteins produced through current protein engineering technology would not be appropriate, because they usually exist in heterogeneous, rather than single, glycoforms. On the other hand, if the recombinant glycoproteins were to be used only as model proteins to demonstrate the feasibility of an analytical system, such as the integrated system in this study, they should be appropriate.

Antibody characteristics such as affinity and specificity can be used to determine the performance of immunoassays (32). To select the best antibody pair to develop the magnetic bead immunoassays for TIMP-1, MME, DPP-4, or tPA, we reviewed the information provided by antibody vendors on the specificity of the antibodies. A monoclonal antibody is preferred for use as the capture antibody because it is potentially more specific than polyclonal antibodies. In addition, when experimental conditions are kept constant, results from monoclonal antibodies are highly reproducible because of the homogeneity of monoclonal antibodies. Commercially available biotinylated antibodies for the detection antibody are preferred over nonbiotinylated antibodies. Antibodies generated using proteins as immunogens are preferred over polypeptides. Furthermore, we used indirect LISAs to perform in-house testing of the affinity and specificity of the selected antibodies toward the recombinant protein. Once the immunoassays were developed, we used the same capture antibodies for the development of LISAs.

In summary, we developed a magnetic bead-based multiplex system that allows for sensitive, multiplex, integrated detection of glycoproteins and their glycoforms. Although TIMP-1 and DPP-4 could not be used for distinguishing AG and NAG cancer, their fucosylated glycoforms could. This result highlights the importance of the integrated detection of glycoproteins and their glycoforms. Through integrated detection, we might be able to discover glycoforms of proteins with improved performance as biomarkers.

References

1. Meany D L, Chan D W. Aberrant glycosylation associated with enzymes as cancer biomarkers. Clin Proteomics 2011; 8:7-20.
2. Lau K S, Dennis J W. N-Glycans in cancer progression. Glycobiology 2008; 18:750-60.
3. Ohtsubo K, Marth J D. Glycosylation in cellular mechanisms of health and disease. Cell 2006; 126:855-67.
4. Mehta A, Block™. Fucosylated glycoproteins as markers of liver disease. Dis Markers 2008; 25: 259-65.
5. Narimatsu H, Iwasaki H, Nakayama F, Ikehara Y, Kudo T, Nishihara S, et al. Lewis and secretor gene dosages affect CA19-9 and DU-PAN-2 serum levels in normal individuals and colorectal cancer patients. Cancer Res 1998; 58:512-8.
6. Meany D L, Zhang Z, Sokoll U, Zhang H, Chan D W. Glycoproteomics for prostate cancer detection: changes in serum PSA glycosylation patterns. J Proteome Res 2009; 8:613-9.
7. Comunale M A, Lowman M, Long R E, Krakover J, Philip R, Seeholzer S, et al. Proteomic analysis of serum associated fucosylated glycoproteins in the development of primary hepatocellular carcinoma. J Proteome Res 2006; 5:308-15.
8. Wang M, Long R E, Comunale M A, Junaidi O, Marrero J, Di Bisceglie A M, et al. Novel fucosylated biomarkers for the early detection of hepatocellular carcinoma. Cancer Epidemiol Biomarkers Prev 2009; 18:1914-21.
9. Marrero J A, Romano P R, Nikolaeva O, Steel L, Mehta A, Fimmel C J, et al. GP73, a resident Golgi glycoprotein, is a novel serum marker for hepatocellular carcinoma. J Hepatol 2005; 43:1007-12.
10. Oka H, Saito A, Ito K, Kumada T, Satomura S, Kasugai H, et al. Multicenter prospective analysis of newly diagnosed hepatocellular carcinoma with respect to the percentage of Lens culinaris agglutinin-reactive alpha-fetoprotein. J Gastroenterol Hepatol 2001; 16:1378-83.
11. Hutchinson W L, Du M Q, Johnson P J, Williams R. Fucosyltransferases: differential plasma and tissue alterations in hepatocellular carcinoma and cirrhosis. Hepatology 1991; 13:683-8.
12. Hakansson K, Cooper H J, Emmett M R, Costello C E, Marshall A G, Nilsson C L. Electron capture dissociation and infrared multiphoton dissociation MS/MS of an N-glycosylated tryptic peptic to yield complementary sequence information. Anal Chem 2001; 73:4530-6.
13. Stalnaker S H, Hashmi S, Lim J M, Aoki K, Porterfield M, Gutierrez-Sanchez G, et al. Site mapping and characterization of 0-glycan structures on alpha-dystroglycan isolated from rabbit skeletal muscle. J Biol Chem 2010; 285:24882-91.
14. Leymarie N, Zaia J. Effective use of mass spectrometry for glycan and glycopeptide structural analysis. Anal Chem 2012; 84:3040-8.
15. Liu A Y, Zhang H, Sorensen C M, Diamond D L. Analysis of prostate cancer by proteomics using tissue specimens. J Urol 2005; 173:73-8.
16. Li Y, Sokoll L J, Rush J, Meany D, Zou N, Chan D W, Zhang H. Targeted detection of prostate cancer proteins in serum using heavy-isotope-labeledpeptide standards and MALDI-TOF/TOF. Proteomics Clin Appl 2009; 3:597-608.
17. Thaysen-Andersen M, Thogersen I B, Nielsen H J, Lademann U, Brunner N, Enghild J J, Hojrup P. Rapid and individual-specific glycoprofiling of the low abundance N-glycosylated protein tissue inhibitor of metalloproteinases-1. Mol Cell Proteomics 2007; 6:638-47.
18. Thaysen-Andersen M, Thogersen I B, Lademann U, Offenberg H, Giessing A M, Enghild J J, et al. Investigating the biomarker potential of glycoproteins using comparative glycoprofiling: application to tissue inhibitor of metalloproteinases-1. Biochim Biophys Acta 2008; 1784:455-63.
19. Li Y, Tao S C, Bova G S, Liu A Y, Chan D W, Zhu H, Zhang H. Detection and verification of glycosylation patterns of glycoproteins from clinical specimens using lectin microarrays and lectin-based immunosorbent assays. Anal Chem 2011; 83: 8509-16.
20. Papac D I, Wong A, Jones A J. Analysis of acidic oligosaccharides and glycopeptides by matrixassisted laser desorption/ionization time-of-flight mass spectrometry. Anal Chem 1996; 68:3215-23.
21. Basa U, Spellman M W. Analysis of glycoproteinderived oligosaccharides by high-pH anion exchange chromatography. J Chromatogr 1990; 499:205-20.
22. Yamashita K, Tachibana Y, Matsuda Y, Katunuma N, Kochibe N, Kobata A. Comparative studies of the sugar chains of aminopeptidase N and dipeptidylpeptidase IV purified from rat kidney brush-border membrane. Biochemistry 1988; 27:5565-73.

23. Schmauser B, Kilian C, Reutter W, Tauber R. Sialoforms of dipeptidylpeptidase IV from rat kidney and liver. Glycobiology 1999; 9:1295-305.
24. Dennis J W, Granovsky M, Warren C E. Glycoprotein glycosylation and cancer progression. Biochim Biophys Acta 1999; 1473:21-34.
25. Handerson T, Camp R, Harigopal M, Rimm D, Pawelek J. Beta1,6-branched oligosaccharides are increased in lymph node metastases and predict poor outcome in breast carcinoma. Clin Cancer Res 2005; 11:2969-73.
26. Guo H B, Lee I, Kamar M, Pierce M. Nacetylglucosaminyltransferase V expression levels regulate cadherin-associated homotypic cell-cell adhesion and intracellular signaling pathways. J Biol Chem 2003; 278:52412-24.
27. Granovsky M, Fata J, Pawling J, Muller W J, Khokha R, Dennis J W. Suppression of tumor growth and metastasis in Mgat5-deficient mice. Nat Med 2000; 6:306-12.
28. Fukushima K, Satoh T, Baba S, Yamashita K. Alpha1,2-Fucosylated and beta-N-acetylgalactosaminylated prostate-specific antigen as an efficient marker of prostatic cancer. Glycobiology 2010; 20:452-60.
29. Tian Y, Bova G S, Zhang H. Quantitative glycoproteomic analysis of optimal cutting temperatureembedded frozen tissues identifying glycoproteins associated with aggressive prostate cancer. Anal Chem 2011; 83:7013-9.
30. Krishhan V V, Khan I H, Luciw P A. Multiplexed microbead immunoassays by flow cytometry for molecular profiling: basic concepts and proteomics applications. Crit Rev Biotechnol 2009; 29: 29-43.
31. Yamamoto K, Yasukawa F, Ito S. Measurement of the sugar-binding specificity of lectins using multiplexed bead-based suspension arrays. Methods Mol Biol 2007; 381:401-9.
32. Li D, Chiu H, Gupta V, Chan D W. Validation of a multiplex immunoassay for serum angiogenic factors as biomarkers for aggressive prostate cancer. Clin Chim Acta 2012; 413:1506-11.
33. Chen S, LaRoche T, Hamelinck D, Bergsma D, Brenner D, Simeone D, et al. Multiplexed analysis of glycan variation on native proteins captured by antibody microarrays. Nat Methods 2007; 4:437-44.
34. Nolan J P, Sklar L A. Suspension array technology: evolution of the flat-array paradigm. Trends Biotechnol 2002; 20:9-12.
35. Kingsmore S F. Multiplexed protein measurement: technologies and applications of protein and antibody arrays. Nat Rev Drug Discov 2006; 5: 310-20.
36. Meany D L, Hackler L Jr, Zhang H, Chan D W. Tyramide signal amplification for antibodyoverlay lectin microarray: a strategy to improve the sensitivity of targeted glycan profiling. J Proteome Res 2011; 10:1425-31.
37. Chen S, Haab B B. Analysis of glycans on serum proteins using antibody microarrays. Methods Mol Biol 2009; 520:39-58.
38. Huhn C, Selman M H, Ruhaak L R, Deelder A M, Wuhrer M. IgG glycosylation analysis. Proteomics 2009; 9:882-913.
39. Andreasen P A, Egelund R, Petersen H H. The plasminogen activation system in tumor growth, invasion, and metastasis. Cell Mol Life Sci 2000; 57:25-40.
40. Kajiyama H, Kikkawa F, Khin E, Shibata K, Ino K, Mizutani S. Dipeptidyl peptidase IV overexpression induces up-regulation of E-cadherin and tissue inhibitors of matrix metalloproteinases, resulting in decreased invasive potential in ovarian carcinoma cells. Cancer Res 2003; 63:2278-83.

Overexpression of Alpha (1,6) Fucosyltransferase and Protein Hyper-Fucosylation in Aggressive Prostate Cancer Although substantial progress has been made in the diagnosis and treatment of aggressive cancer, prostate cancer (PCa) tends to be over-detected/treated for indolent cancer or under-detected/treated for lethal cancer. One of the major reasons for difficulties in diagnosis of the aggressive prostate cancer is the lack of understanding of the molecular changes associated with prostate cancer progression (1).

PCa is the most common cancer in men and the second leading cause of cancer death with an estimated 240,890 newly diagnosed cases and 33,720 deaths in the United States alone in 2011 (2). Prostate-specific antigen (PSA), a marker used to screen for PCa, has obvious limitations in sensitivity and specificity (3, 4). There is now significant controversy as to whether PSA screening is associated with mortality reduction and whether the test results in overtreatment (5-7). A major issue is that we have no good method to reliably distinguish aggressive or lethal prostate cancer from non-aggressive or indolent prostate cancer. Gleason patterns of prostate cancer histopathology, characterized primarily by morphological and architectural attributes of histological structures of surgically resected prostate tumors, are highly correlated with disease aggressiveness and patient outcome; however, a large number of patients with low Gleason scores have aggressive PCa (8).

Aggressive cancers often derive from molecular alterations in cell survival pathways, and these types of cancer tend to metastasize from the primary tumor site to other organ sites. Metastasis is a multi-step process in which cancerous cells separate from the primary tissue and enters the circulatory system where they interact with various host cells before they migrate and lodge in the target organ to form secondary metastatic colonies. Mounting evidence suggests the roles of glycoproteins and their interactions with extracellular matrix (ECM) proteins, such as interaction of selectins with glycan ligands, in metastasis (9).

As one of the most abundant protein modifications, glycosylation has long been known to play an important role in the development and progression of many human diseases (10, 11). Aberrant glycosylation may result in abnormal changes that lead to cancer development. For this reason, analysis of glycosylation and expression of glycogenes have been suggested to facilitate the discovery of molecular changes associated with cancer development. Currently, many clinical cancer biomarkers are glycoproteins (12), such as PSA for PCa, α-fetoprotein (AFP) for hepatocellular carcinoma (HCC), and CA125 for ovarian cancer.

In this study we investigated the expression of glycosyltransferases and levels of glycosylation in prostate cancer samples. From the gene expression profiles (13), we found differences in gene expression of glycotransferase genes between samples from patients with aggressive prostate cancer (Gleason grade 4) and those with non-aggressive prostate cancer (Gleason grade 3). We found that alpha(1,6) fucosyltransferase (FUT8) is likely to be responsible, at least in part, for the aggressive behavior of prostate cancer from the studies on expression and activity of FUT8 and fucosylated proteins in PCa cells and clinical samples from patients with metastatic or aggressive primary prostate cancer. More importantly, we performed tissue microarray (TMA) analysis for FUT8 and hyper-fucosylation, and demonstrated that they were highly expressed in aggressive PCa.

Materials and Methods

Cell Lines and Culture Conditions.

Human prostate cancer cell lines LNCaP and PC3 were purchased from ATCC. LNCaP cells were maintained in RPMI 1640 supplemented with 10% HyClone FBS (Thermo). PC3 cells were maintained in F12K with 10% HI FBS (Gibco).

Prostate Cancer Samples.

Clinical samples and slides for protein extraction and immunohistochemistry were obtained with approval of the Institutional Review Board of the Johns Hopkins University. In this study, primary prostate cancers were collected from radical prostatectomy or transurethral resection specimens at Johns Hopkins Hospital and Johns Hopkins Bayview Medical Center under the NCI-funded Johns Hopkins prostate cancer SPORE project. The Gleason scores for the ten primary tumor slides were 7 (1 patient), 8 (6 patients), and 9 (3 patients). The ten metastatic prostate cancer tissues for Western and lectin blotting were metastatic tissues from men who died of metastatic prostate cancer between 1995 and 2004. The tissues were microdissected to enrich tumor content. Normal prostate tissues were from surgically removed prostates of transplant tissue donors. The collection process was performed with support from the Transplant Resource Center of Maryland (TRCM).

Western and Lectin Blotting.

Methods for western and lectin blotting were described previously (19). Cells and clinical tissues were lysed in 1×RIPA buffer (Millipore, protease inhibitor cocktail from Roche) and incubated on ice for 10 minutes. After incubation, the samples were centrifuged at 15,000×g for 15 minutes. Protein concentration was determined using a BCA protein assay kit (Pierce). For each sample, equal amount of proteins (10 µg) was run on 4-12% NuPAGE gel (Invitrogen) and then transferred to nitrocellulose membrane (Invitrogen). The following antibodies were used: MGAT2 (GnT-II S-21), MGAT4A (GnT-IV A M-71), FUT8 (B-10) and ST6Gal1 (Santa Cruz Biotech); PSA (Scripps Lab); E-cadherin (24E10), alpha-tubulin and actin (Cell Signaling). The secondary antibodies conjugated to HRP were used to probe the membranes for 1 hour at room temperature. Biotinylated lectins obtained from Vector Labs were used for glycan detection followed by incubating with High Sensitivity Streptavidin-HRP for 30 minutes at room temperature. The HRP conjugates were visualized by reagents supplied in the SuperSignal West Pico or FemtoChemiluminescent Kit (Thermo Scientific).

FUT8 Activity Assay.

The activity of FUT8 was determined using a Glycosyltransferase Activity Kit (R&D Systems) as described by the manufacturer. First, 1 mg protein from a cell lysate was immunoprecipitated with FUT8 antibody and Dynabeads Protein G (Invitrogen) by incubation for 2 hours at 4° C. The immunoprecipitated FUT8 was eluted with 50 µl of 50 mM glycine (pH 2.8). MAN9 (Sigma-Aldrich) was used as acceptor substrate at 100 µM. GDP-fucose (Sigma-Aldrich) was used as donor substrate at 5 mM. We then incubated 5 µl coupling phosphatase 1 and 25 µl immunoprecipitate products with MAN9 and GDP-fucose in a 96-well plate at 37° C. 1 hour or overnight. Optical density was determined using Bio-Tek's µQuant microplate spectrophotometer at 620 nm.

RNAi Experiments.

Oligofectamine (Invitrogen) was used to transfect siRNA into cells. Briefly, for 1 well on a 6-well plate, 12 µL of 20 µmol/L control or Hs_FUT8 siRNA (QIAGEN) were mixed in 100 µL of Opti-MEM with 12 µL Oligofectamine in 100 µL Opti-MEM. After incubating for 25 min at room temperature, the mixture was added to cultured cells (40-50% confluent) in 800 µL of Opti-MEM. Regular medium (1000 pp containing 20% fetal bovine serum (FBS) was added to the transfected cells at 3 h after transfection. Two days post-transfection, cells were harvested.

Immunofluorescence.

PC3 cells treated with Non-silence siRNA or FUT8siRNA for 48 hours were seeded on 4 chamber vessel (BD Falcon) for staining after 4-6 hours. Cells were fixed with 4% paraformaldehyde in phosphate-buffered saline 20 min and permeabilized with 0.5% Triton X-100 for 5 min at room temperature. After washing three times with phosphate-buffered saline, cells were blocked in 5% BSA for 1 hour at room temperature and then incubated with Texas Red-Phalloidin (Invitrogen) at a 1:500 dilution for 1 hour at room temperature and mounted with DAPI (Vector Lab) to visualize nuclei. Cells were examined by Nikon super high pressure mercury lamb and Nikon eclipse TE 200 microscope.

Migration Assay.

The cell migration assay was performed in 6-mm Biocoat cell culture control inserts (BD Biosciences). Cells were starved overnight in 0.2% FBS medium. PC3 cells ($2\times10^5$) in 0.2 ml 0.2% FBS medium were added to the insert in 0.6 ml 10% FBS medium and incubated for 24 hours at 37° C. Migrated cells were stained using the Diff-Quik stain kit (Dade Boehringer). All cells on the membrane were counted under a microscope.

Proliferation Assay.

The proliferation of PC3 cell was measured using an MTT assay and a Cell Counting Kit-8 (Dojindo) as described by the manufacturer. Briefly, untreated or siRNA-treated PC3 cells (2000/well) were incubated in a 96-well plate using regular culture medium in triplicate for 18 to 96 hours. CCK-8 solution (10 µl) was added to each well of the plate. After 4 hours incubation, the absorbance was measured at 450 nm using a Bio-Tek's µQuant microplate spectrophotometer.

Immunochemical Staining and Tissue Microarrays.

Staining was initially performed on 10 individual primary prostate tumors and commercial prostate cancer tissue microarray (US Biomax, PR2085b). Briefly, sections of tissue were deparaffinized and rehydrated. Tissues were incubated in antigen retrieval buffer (R&D Systems) at 92-95° C. for 10 min. Tissue was blocked by dual endogenous enzyme block in avidin and biotin blocking buffer (Dako) for 10 min at room temperature. For AAL staining, tissues were incubated in 5% BSA/PBS overnight at 4° C. Biotinylated AAL was diluted to 5 µg/mL in antibody dilute buffer (Dako). After incubation for 1 hour at room temperature and three washes with PBS, lectin binding was detected using the Vectastain ABC kit (Vector Labs) and the DAB kit (Dako). FUT8 staining was evaluated using the Cell and Tissue Staining Sheep Kit (R&D Systems) according to manufacturer's protocol. Anti-FUT8 antibody (R&D Systems) was diluted 1:50 in dilution buffer (Dako) and incubated overnight at 4° C. After washing three times with PBS, tissue was incubated in biotinylated sheep secondary antibody for 1 hour at room temperature. Next, tissue was incubated with High Sensitivity Streptavidin-HRP for 30 minutes. The immuno-reaction was detected using the Dako DAB kit.

Statistical Analyses.

The intensity of all immune-staining was graded visually by a board certified pathologist to 0 (no staining), 1(weak staining), 2 (medium staining), and 3(strong staining). There are totally 87 cases (2 cores from each case) have been effectively graded. All the scored cores were summarized in Table 9. The TMA's Gleason frequencies among men with 2 cores (N=87) was calculated. Proportion of strong staining intensity was compared in stromal and epithelial compartments for both AAL and FUT8 in 174 cancer tissue cores. Strong staining intensity was compared in epithelial and stromal from men with 2 cores 8+ Gleason (88 cores, 44 cases). Agreement was tested in staining intensity among all men (n=87) and men with 2 cores. The agreement was tested between AAL and FUT8 staining in epithelial compartment (strong intensity with a value of 3 vs. all others) by calculating an unweighted kappa statistic. Testing agreement in stromal compartments was not possible due to the small number of cores showing strong staining (AAL: N=3, FUT8: N=0). In Table 2, odds ratios of higher Gleason sum (8 or higher vs. 7 or lower) were calculated in both AAL and FUT8 staining.

Results

Differential Expression of Glycosyltransferases in Aggressive and Non-Aggressive Prostate Cancer Tissues.

Glycosyltransferase genes expressed at different levels in aggressive cancer and non-aggressive cancer may be responsible for prostate cancer progression. From previously published gene expression data, over 170 glycogenes were analyzed in Gleason pattern 3 and pattern 4 tumors (13). From these, we identified three glycosyltransferase genes with significant differences in the expression when high grade (Gleason 4) was compared to low grade (Gleason 3) prostate cancer samples. These three glycosyltransferase genes met two conditions: 1) the genes encoded N-glycan-related glycosyltransferases and 2) their expression was up-regulated in high-grade prostate cancer (Gleason 4). These three genes are beta (1,4) N-acetylglucosaminyltransferase isozyme A (MGAT4A), alpha (1,6) fucosyltransferase (FUT8), and beta (1,2) N-acetylglucosaminyltransferase (MGAT2).

Figures 15A, 15B:
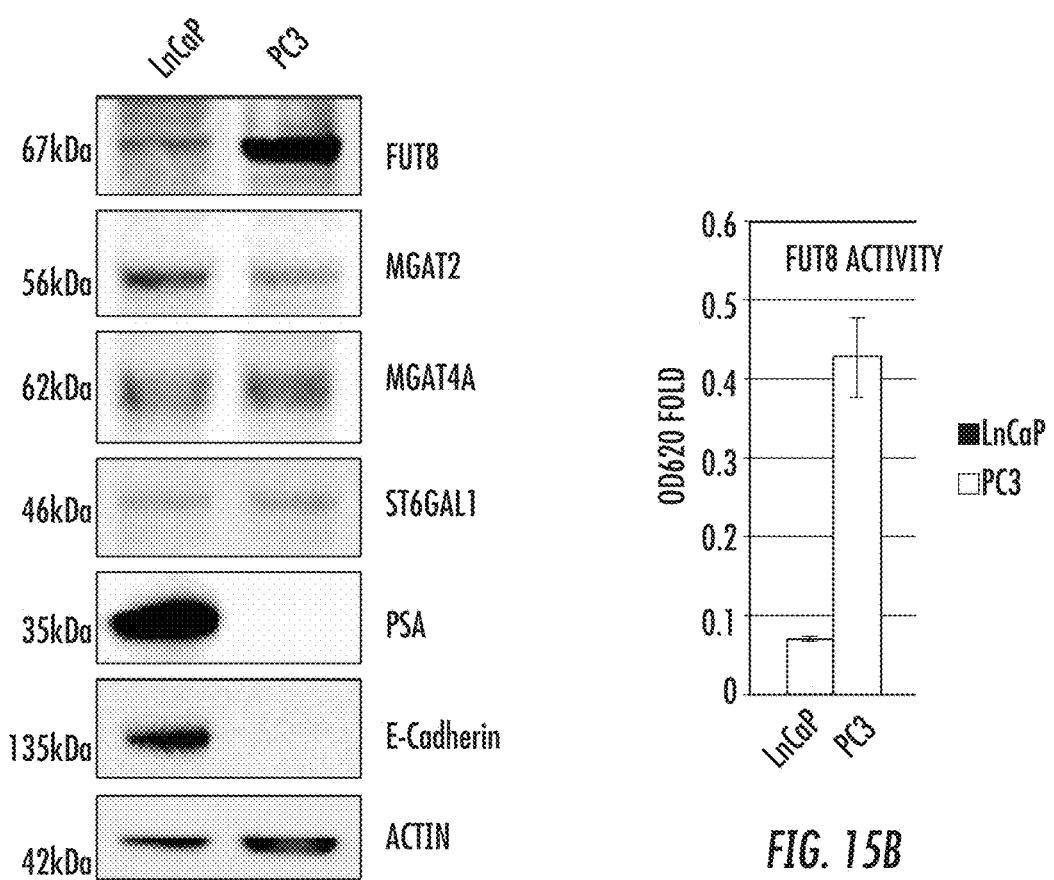
FIG. 15. A glycosyltransferase (FUT8) is expressed at different levels and activity in androgen-dependent and androgen-independent prostate cancer cell lines. A) Comparison of expression of four glycosyltransferases using Western blot analyses; expression of FUT8 is high in PC3 cells and only slightly detectable in LNCaP cells. B) Levels of FUT8 activity in PC3 and LNCaP cells correlated with expression analysis.

We examined the expression of these glycosyltransferase genes in androgen-dependent (LNCaP) and androgen-independent (PC3) prostate cancer cell lines (FIG. 15A). The results showed that, of the three glycosyltransferases, FUT8 was highly expressed in PC3 cells whereas in LNCap cells FUT8 expression was dramatically lower. The expression levels of the other two genes were similar in LNCaP and PC3 cells. Consistent with FUT8 expression, enzyme activity of FUT8 was decreased in LNCaP compared to PC3 cells (FIG. 15B).

PSA, a glycoprotein that is the current prostate cancer screening marker and a known regulated gene by androgen, as expected, was expressed in androgen-dependent LNCaP, but not in more aggressive PC3 cells. Alpha 2,6-sialyltransferase 1 (ST6GAL1), whose expression is increased in colon cancer (14, 15), was not differentially expressed in LNCaP and PC3 cells in this study. We also detected the loss of E-cadherin expression in PC3 cells (FIG. 15A). E-cadherin plays a crucial role in epithelial cell-cell adhesion and in the maintenance of tissue architecture. Loss of expression of E-cadherin results in loss of intercellular adhesion, with possible consequent cell transformation and tumor progression. Thus, the loss of E-cadherin expression in PC3 cells suggested that PC3 is more invasive prostate cancer cells.

Abolished FUT8 Expression Results in Diminished Cancer Aggressiveness.

Figure 16A:
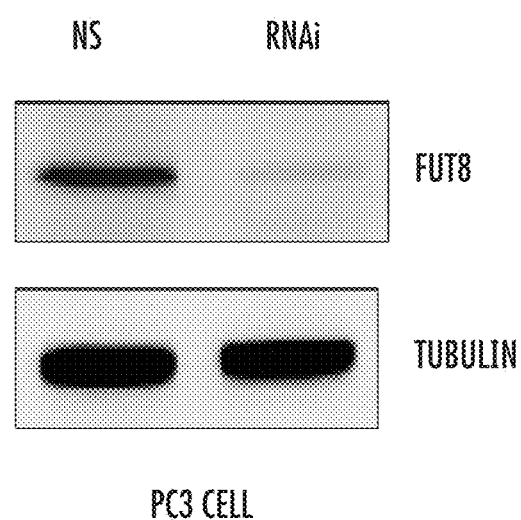
FIG. 16. FUT8 regulates PC3 cell migration. A) FUT8 expression was significantly reduced in PC3 cells upon FUT8 silencing using a specific siRNA to FUT8. B) FUT8 activity was significantly reduced upon FUT8 silencing. C) Trans well migration assays indicated that cells treated with FUT8 siRNA had significantly reduced migration potential compared to controls. D) Morphological changes in PC3 cells 48 hours after FUT8 silencing by siRNA. 1 and 2: representative field photographed using a phase-contrast microscope. 3 and 4: immunofluoresecnt staining of F-actin showing disruption of cell protrusion as the results of interfering with FUT8 expression. E) Cell proliferation was determined by MTT assay using Cell Counting Kit-8. FUT8 silencing did not impair proliferation. F) Lysates from untreated PC3 cells and those treated with FUT8 siRNA were subjected to a lectin blot analysis using AAL, Lens culimaris agglutinin-A (LCA), and *Arachis hypogaea* lectin (PNA). Coomassie Brilliant Blue staining of gels shows comparable amounts proteins in each lane.
Figure 16B:
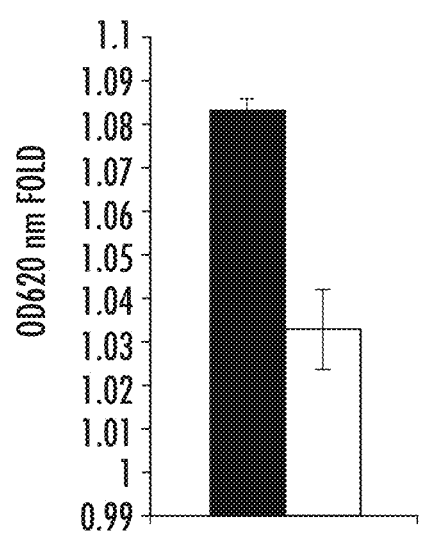
Figure 16C:
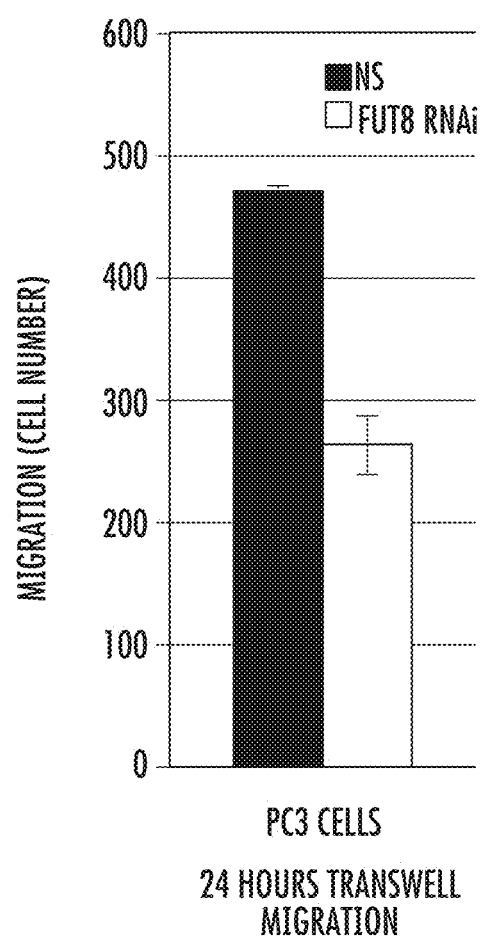
Figure 16D:
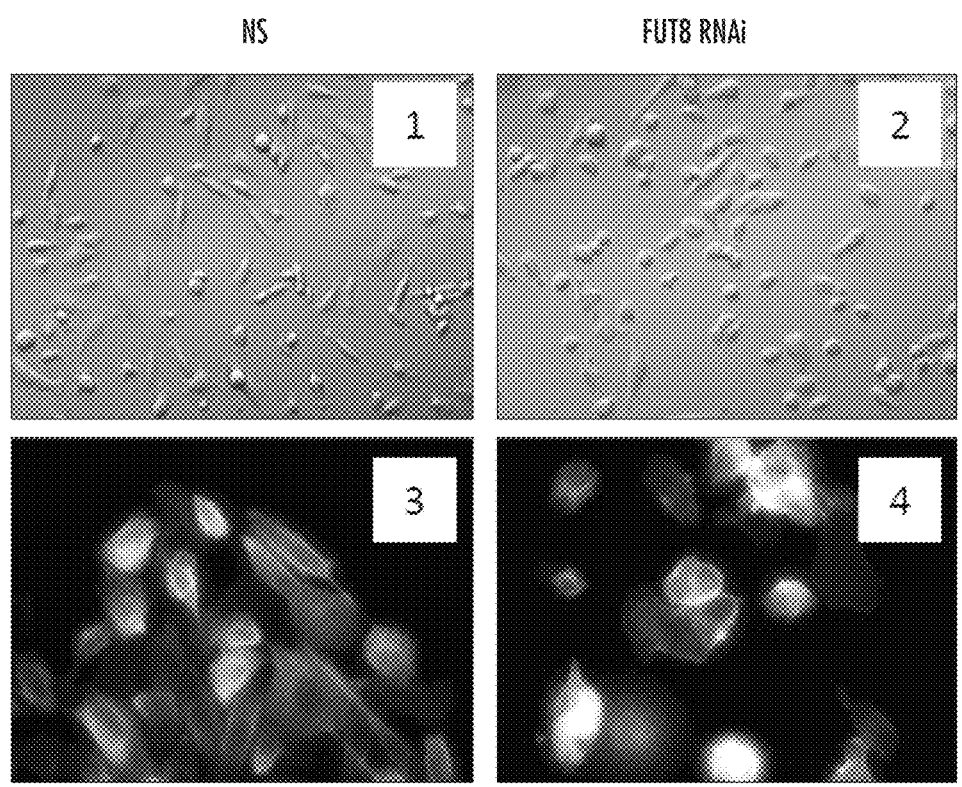

FUT8 has been reported to regulate α3β1 integrin-mediated cell migration (16). Therefore, we investigated the role of FUT8 in prostate cancer metastasis. The influence of FUT8 on prostate cancer cell invasiveness was evaluated using multiporous polycarbonate membrane in transwell Boyden chambers. Silencing FUT8 expression using a siRNA (FIG. 16A), significantly decreased FUT8 enzyme activity in PC3 cells (FIG. 16B). FUT8 silencing dramatically diminished the migration ability of PC3 cells compared to that of cells not treated with FUT8 siRNA (FIG. 16C). Furthermore, we observed that reducing FUT8 expression induced cell rounding and loss of membrane protrusion (FIG. 16D). These results suggest that expression of FUT8 may be required for cancer cells to migrate.

Figure 16E:
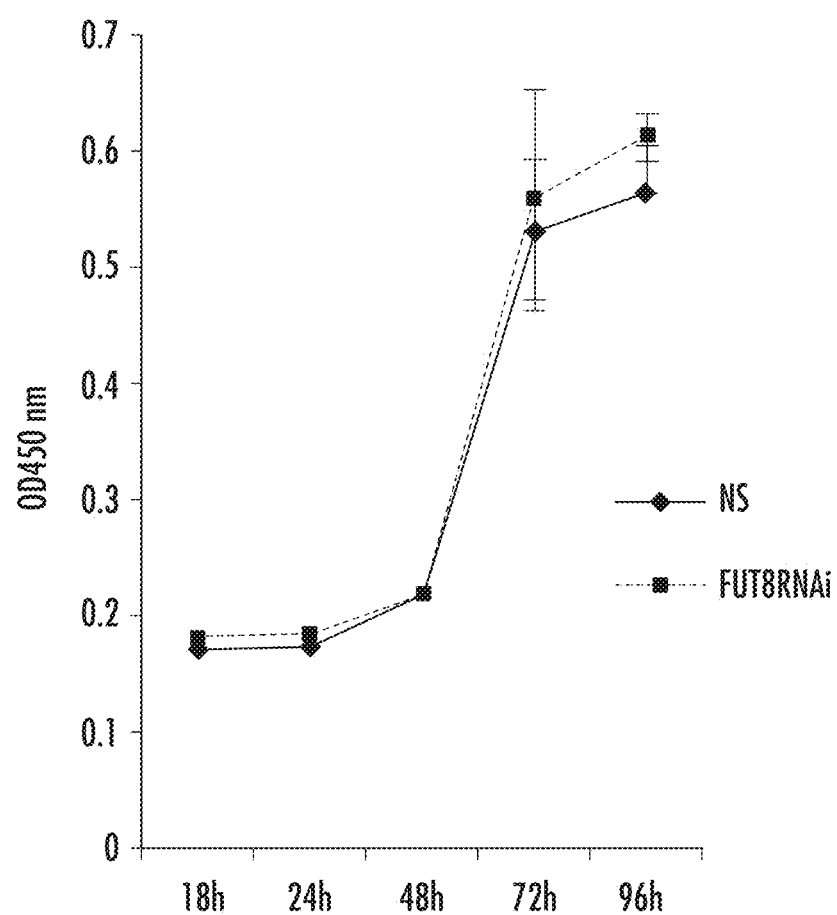
Figure 16F:
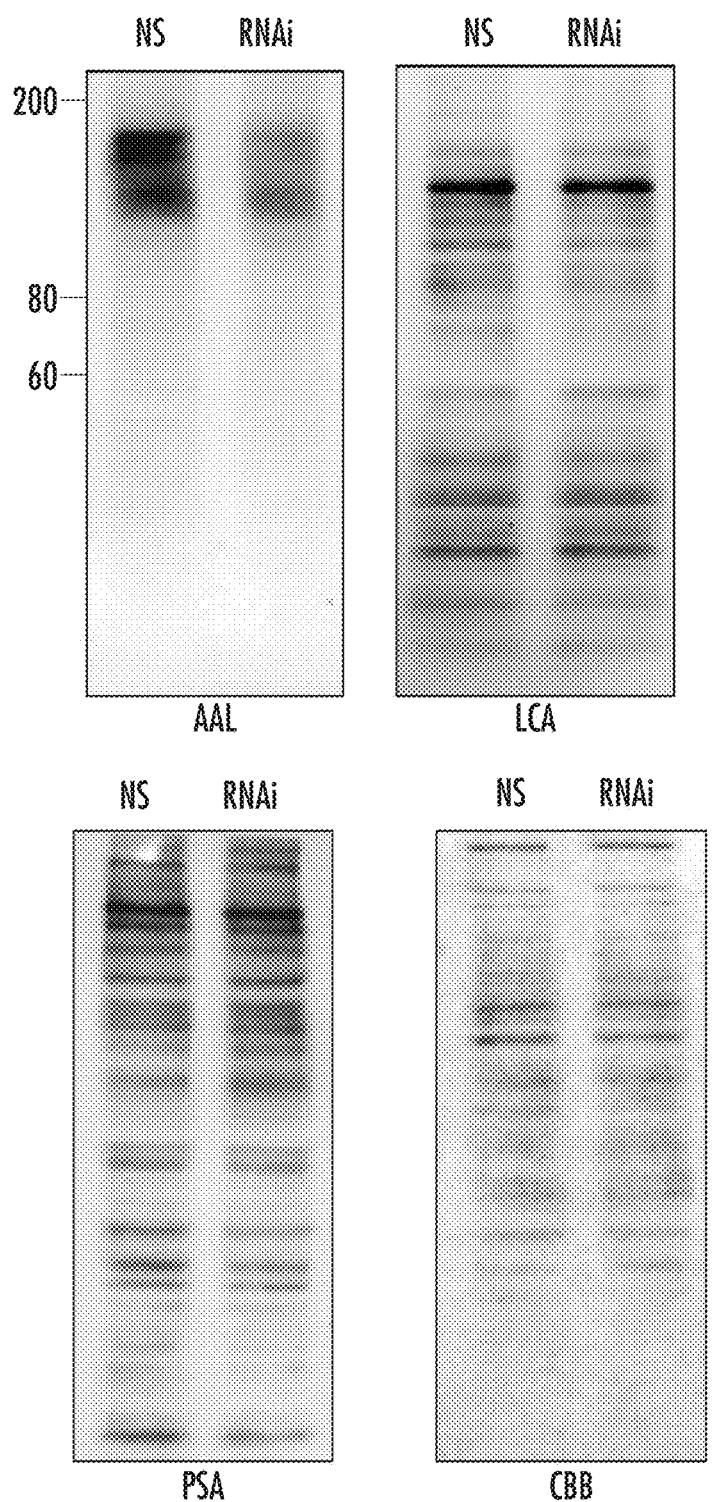

Next, the effect of FUT8 on cell proliferation was analyzed by MTT assay to evaluate whether cell proliferation would be affected by FUT8 silencing (FIG. 16E). Control and FUT8 siRNA-treated PC3 cells exhibited almost equal growth at several different time points. This result showed that decreased cell migration in the FUT8-knockdown cells was not resulted from changes in the ability of the cells to proliferate. To examine whether FUT8-catalyzed fucosylation was affected by FUT8 silencing, fucosylated N-glycans were analyzed by staining with *Aleuria Aurantia* lectin (AAL) (FIG. 16F), which preferentially recognizes the core fucose (17). Several bands migrating at around 80-200 kDa in molecular mass were faintly stained with AAL in FUT8-knockdown cells; the control cells were strongly stained. Staining with *Lens Culinaris* Agglutinin (LCA) and *Pisum Aativum* Agglutinin (PSA), which recognize the α-mannose moiety, was similar in siRNA-treated and untreated cells. Coomassie blue staining of gel showed equal amounts protein in each sample. This result indicated that silencing of FUT8 expression mainly affected core fucosylation of N-glycans.

Concomitant Evaluation of FUT8 and Fucosvlation in Prostate Cancer Tissues.

Figure 17A:
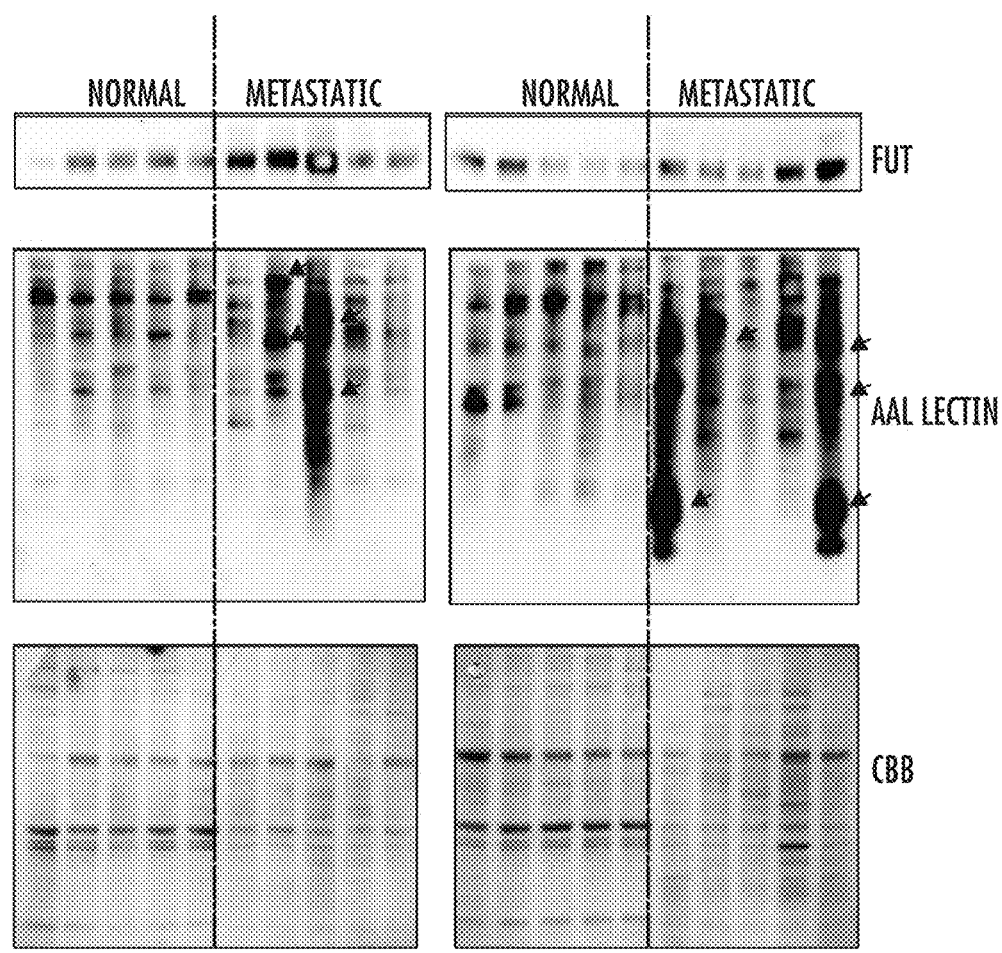
FIG. 17. Analyses of FUT8 expression and fucosylation level in normal prostate and metastatic tissues from prostate cancer patients. A) Proteins from normal prostate tissues and metastatic tissues from prostate cancer patients were subjected to western blot and lectin blot using FUT8 antibody (top panel) and AAL (middle panel). Coomassie Brilliant Blue (CBB) staining was used as loading control. B) Quantifications of AAL and FUT8 by comparison to CBB staining with NIH ImageJ. Statistically significant differences (P) between normal and metastatic groups are indicated. Correlations between AAL/CBB and FUT8/CBB are indicated.
Figure 17B:
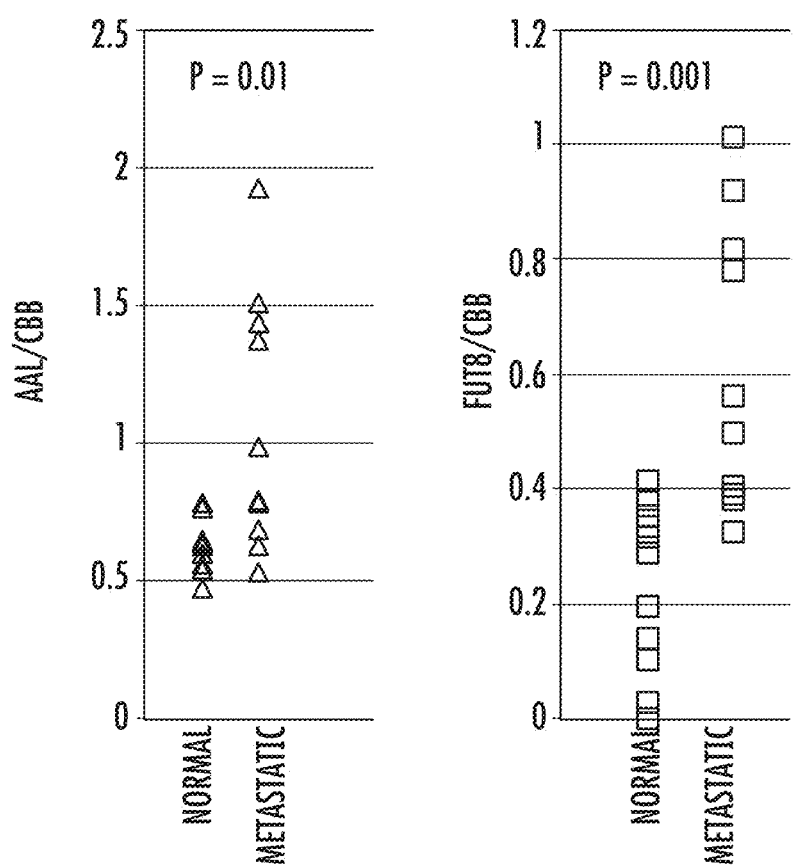

To investigate the expression of FUT8 and hyper-fucosylation in prostate cancer tissues, we analyzed prostate tissues from 10 normal individuals and metastatic tissues from 10 prostate cancer cases using FUT8 antibody and AAL lectin (FIG. 17A). To determine the levels of FUT8 and fucosylation, the intensities of FUT8 and fucosylation were quantified and compared to Coomassie Brilliant Blue (CBB) staining of total proteins using ImageJ process (FIG. 17B). FUT8 expression was higher in 6 of 10 metastatic tissues and significantly elevated in comparison to the levels in the normal prostate tissues. Fucosylated proteins, which were detected by the AAL lectin, were also significantly elevated in metastatic group samples with the elevated FUT8 expression (FIG. 17B).

Characterization of FUT8 Expression and Hyper-Fucosylation by Immunohisto-Chemical Staining.

Figure 18A:
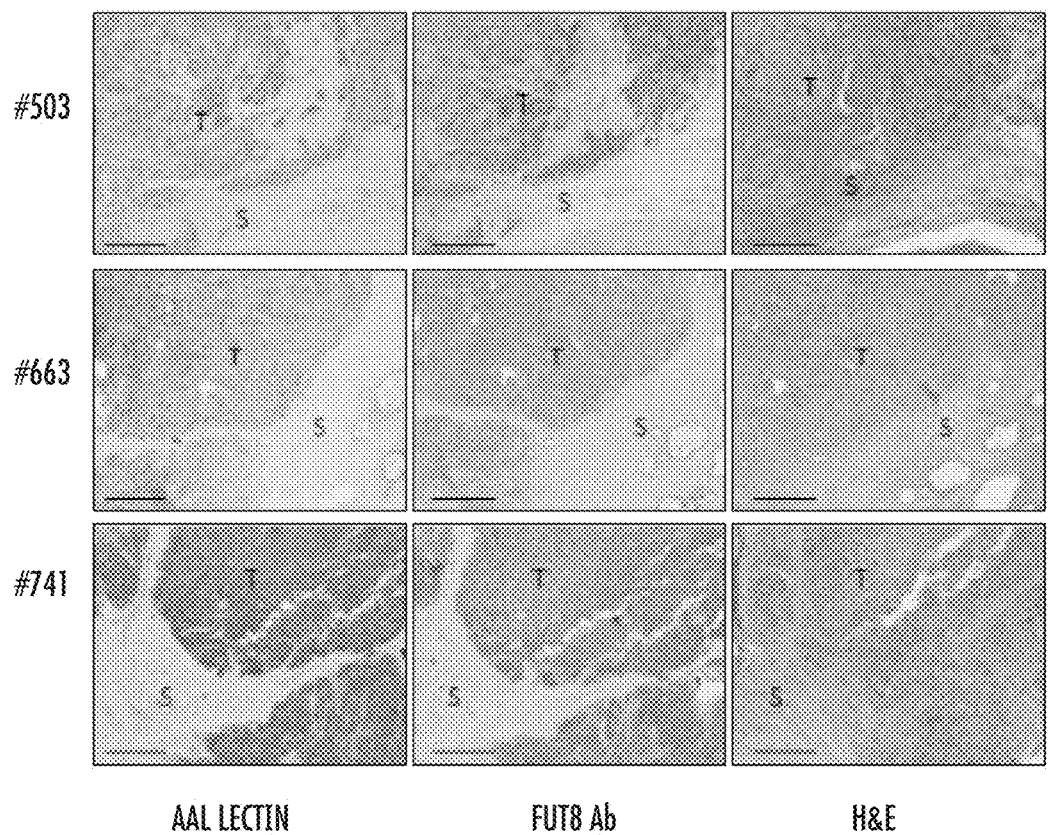
FIG. 18. Immunohistochemical analysis of FUT8 expression and fucosylation levels in 10 primary prostate cancer tissues. A) Representative images of immunohistochemical analyses of FUT8 expression and AAL staining (fucosylation level) from 10 primary prostate cancer tissues. Hematoxylin and eosin (H&E) were obtained to confirm the tumor area. T: tumor; S: stroma. Scale bar: 500 µm. b) Summary of FUT8 expression and AAL staining. Slides were evaluated independently by a pathologist (Q.K.L.). The intensity of staining was graded visually as no staining (0), weak (1), moderate (2), and strong (3).

To explore whether FUT8 overexpression and protein hyper-fucosylation are also observed in primary prostate tumors, we examined levels of FUT8 expression and fucosylation by immunohistochemical staining in 10 primary prostate tumors. High levels of FUT8 protein and fucosylation were detected in the tumor epithelial compartments, but not in stromal area (FIG. 18A). High levels of AAL and FUT8 staining (strong and medium staining) were detected in 9 and 7 of 10 primary prostate tumors, respectively (FIG. 18B). In stromal compartment, both AAL lectin and FUT8 only showed weak and no staining. This result revealed that FUT8 overexpression and hyper-fucosylation were features of tumor epithelial cells but not adjacent stromal tissues.

To assess a large pool of specimens, TMA analysis was performed on 87 pathogenic prostate cases and each case contained 2 tissue cores (174 cores in total). Tissue cores were from prostate adenocarcinoma of varying tumor grades. The prostate tumor cores were classified by pathologist to three categories with 33 cores (19.0%) from Gleason 6 or less, 38 cores (21.8%) from Gleason 7, and 103 cores (59.2%) from Gleason 8 or above (Table 9). The majority of cases (73.6%) contain a consistent Gleason score for the two cores, including 44 cases (50.6%) with both cores showing Gleason score of 8 or above (8+), 10 cases (11.5%) with both cores showing Gleason score of 7, and 10 cases (11.5%) with both cores showing Gleason score of 6 or less. The remaining cases (26.4%) showed different Gleason score for the 2 cores.

Next, we examined the proportion of staining intensity in stromal and epithelial cells. The intensities of each core with FUT8 and AAL staining were evaluated independently without the identification of tissue information by a board certified pathologist. FUT8 and AAL staining were observed in most of prostate adenocarcinoma tissue sections (Table 9). While scoring for intensity, a subset of prostate adenocarcinoma sections exhibited strong staining (value of 3) for AAL (72.6%) and FUT8 (50.0%) in epithelial compartment, while no strong FUT8 staining observed in stroma and only 5 tissue cores (2.9%) stained for AAL were scored as strongly stained (value of 3) in stromal compartment. Tissue microarray analysis also revealed that of the prostate adenocarcinoma with 2 cores of Gleason 8 or above (88 cores and 44 cases) exhibiting high percentage of strong staining for AAL (78.4%) and FUT8 (56.8%). This data indicates strong staining for both AAL and FUT8 in epithelial compartment compared to stromal compartment and the results suggested that high FUT8 and fucosylation levels might associated with high Gleason score in primary prostate cancers.

TABLE 9

Tissue Microarray. 174 prostate cores scored for Gleason score, FUT8 and AAL. Scoring based on staining intensity. 0 = no staining; 1 = weak staining, 2 = moderate staining, and 3 = strong staining.

| Tissue Characteristic | FUT8 in epithelial (%) | FUT8 in stromal (%) | AAL in epithelial (%) | AAL in stromal (%) |
|---|---|---|---|---|
| Adenocarcinoma Gleason ? 6; 33 cores | | | | |
| Staining Intensity 0 | 0.6 | 1.1 | 0.0 | 7.5 |
| Staining Intensity 1 | 4.6 | 14.4 | 2.9 | 6.3 |
| Staining Intensity 2 | 8.6 | 3.4 | 6.3 | 4.0 |
| Staining Intensity 3 | 5.2 | 0.0 | 9.8 | 1.1 |
| Adenocarcinoma Gleason = 7; 38 cores | | | | |
| Staining Intensity 0 | 0.0 | 0.6 | 0.0 | 5.7 |
| Staining Intensity 1 | 2.9 | 8.6 | 0.0 | 6.9 |
| Staining Intensity 2 | 7.5 | 12.6 | 4.6 | 8.0 |
| Staining Intensity 3 | 11.5 | 0.0 | 17.2 | 1.1 |
| Adenocarcinoma Gleason ? 8; 103 cores | | | | |
| Staining Intensity 0 | 0.6 | 2.3 | 0.0 | 10.9 |
| Staining Intensity 1 | 6.9 | 25.3 | 2.9 | 25.3 |
| Staining Intensity 2 | 18.4 | 31.6 | 10.9 | 22.4 |
| Staining Intensity 3 | 33.3 | 0.0 | 45.4 | 0.6 |

We calculated unweighted and weighted kappa statistics to test the agreement between two cores with respect to AAL and FUT8 staining intensity (evaluated staining intensity and strong intensity with a value of 3 vs. all others) in epithelial compartment from 87 men (174 cancer tissue cores). Kappa statistic of AAL and FUT8 strong staining showed moderate (0.540) and Good (0.702) coefficient in epithelial compartment for AAL and FUT respectively among all men. To test the agreement between AAL and FUT8 staining, we calculated an unweighted kappa statistic (strong intensity with a value of 3 vs. all others) in epithelial compartment from 174 cancer tissue cores and observed a relatively weak agreement (Kappa=0.276) between AAL and FUT8 staining.

Next, we tested whether FUT8 overexpression and protein hyper-fucosylation were correlated with prostate cancer Gleason score. Staining intensities for FUT8 and AAL on TMAs were used to investigate the correlation of FUT8 overexpression and/or hyper-fucosylation to aggressive prostate cancer (Gleason score 8 or higher, Table 10). We calculated odds radios of higher Gleason score (8 or higher vs. 7 or lower) and 95% confidence intervals (CI) by strong staining (value of 3) in epithelial compartments using logistic regression (Table 10). Models 1 and 2 showed that strong staining for both AAL (1.68 in Gleason 8 or higher) and FUT8 (1.87 in Gleason 8 or higher) in epithelial compartment were associated with a higher Gleason score. Models 3 and 4 suggested no additive effect when there existed strong staining for both AAL and FUT8 with Gleason 8 or higher.

TABLE 10

Odds ratios of higher Gleason sum (Gleason 8 or higher) and 95% confidence intervals (CI) by strong staining (value of 3) in epithelial compartment using logistic regression.

| Model | Group | Gleason 8 or higher OR (95% CI) | P |
|---|---|---|---|
| Model 1: AAL | Weak Staining | 1.00 Ref | |
| | Strong Staining | 1.68 (0.74, 3.81) | .21 |
| Model 2: FUT8 | Weak Staining | 1.00 Ref | |
| | Strong Staining | 1.87 (0.88, 3.95) | .10 |
| Model 3: Strong Staining Count | 0 Strong Staining (neither AAL nor FUT8) | 1.00 Ref | |
| | 1 Strong Staining (either AAL or FUT8 but not both) | 1.78 (0.66, 4.81) | .26 |
| | 2 Strong Staining (both AAL and FUT8) | 2.50 (0.93, 6.70) | .07 |
| | P-trend | | .07 |
| Model 4: Strong Staining by Gene | 0 Strong Staining (neither AAL nor FUT8) | 1.00 Ref | |
| | AAL Strong Staining Only | 1.65 (0.58, 4.67) | .35 |
| | FUT8 Strong Staining Only | 2.50 (0.52, 11.92) | .25 |
| | AAL & FUT8 Strong Staining | 2.50 (0.93, 6.70) | .07 |

Discussion

FUT8 catalyzes the transfer of a fucose from GDP-fucose to the innermost GlcNAc residue of hybrid and complex N-linked oligosaccharides in glycoproteins via an α(1,6)-linkage to form the core fucosylation in mammals. FUT8 has marked functions on signal transduction (18, 19), cell adhesion (16) and intracellular signaling (20). Core fucosylated N-glycans are widely distributed in a variety of glycoproteins and are altered under some pathological conditions (10). Core fucosylated AFP, but not AFP alone, is used clinically to distinguish patients with HCC from those with chronic hepatitis and liver cirrhosis (21). Increased fucosylation is also observed in other types of cancers, including lung cancer, colorectal cancer, breast cancer, and pancreatic cancer (22-24). In prostate cancer, increased fucosylation of PSA and haptoglobin are detected in serum of PCa patients (9, 25), and elevated core fucosylation and a 2-3 sialylation were reported in serum proteins from PCa patients but not those with benign prostate hyperplasia (BPH) by mass spectrometer analysis (26). However, glycosylation changes in glycoproteins from prostate tumors and the function of glycosyltransferases such as FUT8 in PCa progression has not been demonstrated. In this study, we found overexpression of FUT8 and hyper-fucosylation of proteins in aggressive prostate cancer.

Two prostate cancer cell lines were selected as model systems for initial glycobiology analyses to determine the expression and function of glycosyltransferase in cancer progression. PC3 cells are androgen-independent prostate cells that do not express PSA (27). Androgen independence and loss of PSA expression occur only in very late stages of the disease. LnCap cell line is androgen-dependent and a cell model of less aggressive prostate cancer (27)(28, 29). The androgen receptor pathway is related to the invasive behavior of prostate cancer cells (30). In our studies, the expression of the four glycosyltransferases FUT8, MGAT2, MGAT4A, and ST6GAL1 were analyzed in both androgen-dependent and independent cells. Of the four candidates, FUT8 was expressed at significantly higher levels in androgen-independent cells than in the androgen-dependent cells. The other glycosyltransferases evaluated did not have differential expression. FUT8 may play a role in metastasis as we observed reduced cell migration upon silencing of FUT8 expression but not affecting cell proliferation.

From analysis of 10 normal and 10 metastatic prostate cancer tissues, as well as 10 cases of primary prostate cancer tissues, we found that FUT8 expression and protein fucosylation detected by AAL were concomitantly elevated in metastatic tissues and in the primary cancer. The results were further verified by staining of a prostate cancer TMA for FUT8 overexpression and hyper fucosylation. There is a significant correlation between strong staining for AAL and FUT8 in the epithelial compartments of tumor tissues and in tissues with high Gleason score (8 or higher).

In theory, it is challenging to directly analyze glycans in patient tissue samples due to the limited tissue amount and tissue heterogeneity. Lectins can specifically recognize glycans on the cell surface (31) and thus have particular value in detecting glycosylation differences at cytological and histological levels. *Ulex Europaeus* I Agglutinin (UEA 1), which binds α1,2-linked fucose residues, and *Helix Pomatia* Agglutinin, which binds a GalNAc, are utilized in breast cancer biopsy evaluation (32, 33). In fact, many clinical tests currently used to diagnose and monitor the effects of therapy of cancer take advantage of glycosylation differences during the disease process. Few biomarker explorations have been based on these differences, although fucosylated α-fetoprotein expression is evaluated by an antibody-lectin enzyme immunoassay based method for liver cancer detection (34). In prostate cancer, this vacancy could be filled by our discovery that AAL is significantly correlated with increased PCa metastatic progression. Fucosylated proteins which were detected by AAL were dramatically elevated in both metastatic samples by Western blots (FIG. 17) and primary histological PCa sections (FIG. 18). Majority tissue cores have high AAL staining (72.4%) in epithelial compartments. Furthermore, from 88 cores of 8+ Gleason, higher percentage of tissue cores (78.4%) showed strong AAL lectin staining. The odds ratio analysis showed the association of AAL with higher Gleason score (8 or higher) (Table 10). Our data indicate that AAL staining is elevated in aggressive PCa, which clinical PSA tests fail to do.

Alterations in glycosyltransferase expression as cancer progresses may provide valuable information regarding the molecular changes involved in aggressive cancer. For instance, N-glycan GlcNAc transferase V (MGAT V) and GlcNAc transferase III, which catalyze synthesis of the bisecting branch of N-glycans, are upregulated in numerous cancers, and overexpression of these enzymes results in changes in tumor metastasis (35, 36). *Phaseolus vulgaris* leukoagglutinating lectin, which binds to the products of MGAT V, can be used to predict the prognosis of human colorectal carcinoma (37). Sialyltransferases, such as ST3Gal I, ST6GalNAc I, and ST6Gal I, are overexpressed in breast and colon cancer (38-40). FUT8 expression is upregulated in thyroid carcinoma and associated with tumor size (41). Our data showed that FUT8 was overexpressed in androgen-independent PCa cells and clinical PCa tissues. TMA staining for FUT8 in epithelial and stromal compartments showed 50% (87 cores) and 0 cores, respectively. In the case with 8+ Gleason (88 cores, 44 cases), higher percentage of core (56.8%) showed strong FUT8 staining. Importantly, FUT8 in epithelial compartment is also associated with a higher Gleason score (Table 10). These results suggest that FUT8 may act as a co-indicator with AAL to distinguish aggressive and non-aggressive PCa.

To date, no individual PCa marker reliably detects aggressive PCa. A combination of biomarkers may make reliable diagnoses possible. In our study, the percentage of strong AAL and FUT8 staining in 8+ Gleason patient samples were 78.4% and 56.8%, respectively. Thus, 21.6% and 43.2% of 8+ Gleason cancers were not detected by AAL and FUT8 staining alone. There is relatively weak agreement between AAL and FUT8 staining (Kappa=0.276). This could be caused by the changes in expression or activities of other glycosylation enzymes (glycosyltransferases or glycosidases) in the glycan synthesis pathways in aggressive cancer since AAL not only binds to core fucosylation (α1, 6) fucose, the FUT8 substrate), but also to other branched fucose residues, such as α2, α3/4 fucose residues that are the products of other glycosylation enzymes. This suggests that the AAL and FUT8 staining could be potentially combined to increase the sensitivity of detecting aggressive PCa.

In summary, overexpression of FUT8 and hyper-fucosylation of proteins are associated with aggressive PCa. AAL and FUT8 antibody are promising tests that appear to distinguish between aggressive and non-aggressive PCa. By employing a combination of lectin assays and measuring enzyme expression or activity, the value of these glycosylation changes in diagnosis of aggressive prostate cancer in tissues and body fluids will be determined in future studies.

REFERENCES

1. Makarov, D. V., Loeb, S., Getzenberg, R. H. & Partin, A. W. (2009) *Annu Rev Med* 60, 139-51.
2. Siegel, R., Ward, E., Brawley, O. & Jemal, A. CA Cancer J Clin 61, 212-36.
3. Thompson, I. M., Pauler, D. K., Goodman, P. J., Tangen, C. M., Lucia, M. S., Parnes, H. L., Minasian, L. M., Ford, L. G., Lippman, S. M., Crawford, E. D., Crowley, J. J. & Coltman, C. A., Jr. (2004) N Engl J Med 350, 2239-46.
4. Nadler, R. B., Humphrey, P. A., Smith, D. S., Catalona, W. J. & Ratliff, T. L. (1995) J Urol 154, 407-13.
5. Schroder, F. H., Hugosson, J., Roobol, M. J., Tammela, T. L., Ciatto, S., Nelen, V., Kwiatkowski, M., Lujan, M., Lilja, H., Zappa, M., Denis, L. J., Recker, F., Berenguer, A., Maattanen, L., Bangma, C. H., Aus, G., Villers, A., Rebillard, X., van der Kwast, T., Blijenberg, B. G., Moss, S. M., de Koning, H. J. & Auvinen, A. (2009) N Engl J Med 360, 1320-8.
6. Schroder, F. H. N Engl J Med 365, 1953-5.
7. Tosoian, J. J., Trock, B. J., Landis, P., Feng, Z., Epstein, J. I., Partin, A. W., Walsh, P. C. & Carter, H. B. J Clin Oncol 29, 2185-90.
8. Markert, E. K., Mizuno, H., Vazquez, A. & Levine, A. J. Proc Natl Acad Sci USA 108, 21276-81.
9. Fujimura, T., Shinohara, Y., Tissot, B., Pang, P. C., Kurogochi, M., Saito, S., Arai, Y., Sadilek, M., Murayama, K., Dell, A., Nishimura, S. & Hakomori, S. I. (2008) Int J Cancer 122, 39-49.
10. Taniguchi, N., Miyoshi, E., Gu, J., Honke, K. & Matsumoto, A. (2006) Curr Opin Struct Biol 16, 561-6.
11. Ohtsubo, K. & Marth, J. D. (2006) Cell 126, 855-67.
12. Dube, D. H. & Bertozzi, C. R. (2005) Nat Rev Drug Discov 4, 477-88.
13. Pascal, L. E., Vencio, R. Z., Page, L. S., Liebeskind, E. S., Shadle, C. P., Troisch, P., Marzolf, B., True, L. D., Hood, L. E. & Liu, A. Y. (2009) BMC Cancer 9, 452.
14. Seales, E. C., Jurado, G. A., Brunson, B. A., Wakefield, J. K., Frost, A. R. & Bellis, S. L. (2005) Cancer Res 65, 4645-52.
15. Swindall, A. F. & Bellis, S. L. J Biol Chem 286, 22982-90.
16. Zhao, Y., Itoh, S., Wang, X., Isaji, T., Miyoshi, E., Kariya, Y., Miyazaki, K., Kawasaki, N., Taniguchi, N. & Gu, J. (2006) J Biol Chem 281, 38343-50.
17. Matsumura, K., Higashida, K., Ishida, H., Hata, Y., Yamamoto, K., Shigeta, M., Mizuno-Horikawa, Y., Wang, X., Miyoshi, E., Gu, J. & Taniguchi, N. (2007) J Biol Chem 282, 15700-8.
18. Wang, X., Inoue, S., Gu, J., Miyoshi, E., Noda, K., Li, W., Mizuno-Horikawa, Y., Nakano, M., Asahi, M., Takahashi, M., Uozumi, N., Ihara, S., Lee, S. H., Ikeda, Y., Yamaguchi, Y., Aze, Y., Tomiyama, Y., Fujii, J., Suzuki, K., Kondo, A., Shapiro, S. D., Lopez-Otin, C., Kuwaki, T., Okabe, M., Honke, K. & Taniguchi, N. (2005) Proc Natl Acad Sci USA 102, 15791-6.
19. Wang, X., Gu, J., Ihara, H., Miyoshi, E., Honke, K. & Taniguchi, N. (2006) J Biol Chem 281, 2572-7.
20. Li, W., Liu, Q., Pang, Y., Jin, J., Wang, H., Cao, H., Li, Z., Wang, X., Ma, B., Chi, Y., Wang, R., Kondo, A., Gu, J. & Taniguchi, N. J Biol Chem 287, 2500-8.
21. Sato, Y., Nakata, K., Kato, Y., Shima, M., Ishii, N., Koji, T., Taketa, K., Endo, Y. & Nagataki, S. (1993) N Engl J Med 328, 1802-6.
22. Liu, Y. C., Yen, H. Y., Chen, C. Y., Chen, C. H., Cheng, P. F., Juan, Y. H., Chen, C. H., Khoo, K. H., Yu, C. J., Yang, P. C., Hsu, T. L. & Wong, C. H. Proc Natl Acad Sci USA 108, 11332-7.
23. Kyselova, Z., Mechref, Y., Kang, P., Goetz, J. A., Dobrolecki, L. E., Sledge, G. W., Schnaper, L., Hickey, R. J., Malkas, L. H. & Novotny, M. V. (2008) Clin Chem 54, 1166-75.
24. Miyoshi, E., Shinzaki, S., Moriwaki, K. & Matsumoto, H. Methods Enzymol 478, 153-64.
25. Kosanovic, M. M. & Jankovic, M. M. (2005) J Buon 10, 247-50.
26. Saldova, R., Fan, Y., Fitzpatrick, J. M., Watson, R. W. & Rudd, P. M. Glycobiology 21, 195-205.
27. Kaighn, M. E., Narayan, K. S., Ohnuki, Y., Lechner, J. F. & Jones, L. W. (1979) Invest Urol 17, 16-23.
28. Horoszewicz, J. S., Leong, S. S., Chu, T. M., Wajsman, Z. L., Friedman, M., Papsidero, L., Kim, U., Chai, L. S., Kakati, S., Arya, S. K. & Sandberg, A. A. (1980) Prog Clin Biol Res 37, 115-32.
29. Navone, N. M., Olive, M., Ozen, M., Davis, R., Troncoso, P., Tu, S. M., Johnston, D., Pollack, A., Pathak, S., von Eschenbach, A. C. & Logothetis, C. J. (1997) Clin Cancer Res 3, 2493-500.
30. Baldi, E., Bonaccorsi, L. & Forti, G. (2003) Endocrinology 144, 1653-5.
31. Vijayan, M. & Chandra, N. (1999) Curr Opin Struct Biol 9, 707-14.
32. Brooks, S. A. & Leathem, A. J. (1991) Lancet 338, 71-4.
33. Fenlon, S., Ellis, I. O., Bell, J., Todd, J. H., Elston, C. W. & Blamey, R. W. (1987) J Pathol 152, 169-76.
34. Korekane, H., Hasegawa, T., Matsumoto, A., Kinoshita, N., Miyoshi, E. & Taniguchi, N. Biochim Biophys Acta.
35. Granovsky, M., Fata, J., Pawling, J., Muller, W. J., Khokha, R. & Dennis, J. W. (2000) Nat Med 6, 306-12.
36. Yoshimura, M., Nishikawa, A., Ihara, Y., Taniguchi, S. & Taniguchi, N. (1995) Proc Natl Acad Sci USA 92, 8754-8.
37. Seelentag, W. K., Li, W. P., Schmitz, S. F., Metzger, U., Aeberhard, P., Heitz, P. U. & Roth, J. (1998) Cancer Res 58, 5559-64.
38. Burchell, J., Poulsom, R., Hanby, A., Whitehouse, C., Cooper, L., Clausen, H., Miles, D. & Taylor-Papadimitriou, J. (1999) Glycobiology 9, 1307-11.
39. Sewell, R., Backstrom, M., Dalziel, M., Gschmeissner, S., Karlsson, H., Noll, T., Gatgens, J., Clausen, H., Hansson, G. C., Burchell, J. & Taylor-Papadimitriou, J. (2006) J Biol Chem 281, 3586-94.
40. Chiricolo, M., Malagolini, N., Bonfiglioli, S. & Dall'Olio, F. (2006) Glycobiology 16, 146-54.
41. Ito, Y., Miyauchi, A., Yoshida, H., Uruno, T., Nakano, K., Takamura, Y., Miya, A., Kobayashi, K., Yokozawa, T., Matsuzuka, F., Taniguchi, N., Matsuura, N., Kuma, K. & Miyoshi, E. (2003) Cancer Lett 200, 167-72.

We claim:

1. A multiplex assay for distinguishing aggressive from non-aggressive prostate cancer comprising the steps of:
   a. incubating a sample comprising biomarker proteins of interest obtained from a patient with a mixture of magnetic beads coupled with monoclonal antibodies that specifically bind the biomarker proteins of interest, wherein the biomarker proteins of interest comprise fucosylated tissue inhibitor of metallopeptidase 1 (TIMP-1) and fucosylated dipeptidyl peptidase-IV (DPP-4);
   b. adding a mixture of biotinylated lectins that specifically bind fucosylated TIMP-1 and fucosylated DPP-4;
   c. adding a streptavidin labeled fluorescent marker that binds the biotinylated lectins bound to the fucosylated TIMP-1 and fucosylated DPP-4;
   d. detecting fucosylated TIMP-1 and fucosylated DPP-4; and
   e. identifying the patient as having aggressive prostate cancer if the fluorescence intensity of fucosylated TIMP-1 and fucosylated DPP-4 is statistically significantly increased relative to a reference that correlates to non-aggressive prostate cancer.

2. The multiplex assay of claim 1, wherein the sample is a serum sample.

3. The multiplex assay of claim 1, wherein the biotinylated lectin is *Ulex* europeaus agglutinin (UEA).

4. The multiplex assay of claim 1, wherein the fluorescent marker is phycoerythrin.

5. The multiplex assay of claim 1, wherein the sample comprises about 300 ng of protein.

6. The multiplex assay of claim 1, wherein the biomarker proteins further comprise soluble form of the TIE-2 receptor (sTIE-2), soluble form of the vascular endothelial growth factor receptor 1 (sVEGFR-1), and alpha (1,6) fucosyltransferase (FUT8).

7. The multiplex assay of claim 6, further comprising adding a mixture of biotinylated detection antibodies that specifically bind sTIE-2, SVEGFR-1 and FUT8; adding a streptavidin labeled fluorescent marker that binds the biotinylated antibodies bound to sTIE-2, sVEGFR-1, and FUT8; detecting sTIE-2, sVEGFR-1, and FUT8; and identifying the patient as having aggressive prostate cancer if the fluorescence intensity of sTIE-2, FUT8, fucosylated TIMP-1 and fucosylated DPP-4 is statistically significantly increased relative to a reference and the fluorescence intensity of sVEGFR-1 is statistically significantly decreased relative to a reference.

8. The multiplex assay of claim 7, wherein the biotinylated detection antibodies are immunoglobulin G antibodies.

9. A multiplex assay for distinguishing aggressive from non-aggressive prostate cancer comprising the steps of:
   a. incubating a sample comprising biomarker proteins of interest obtained from a patient with a mixture of magnetic beads coupled with monoclonal antibodies that specifically bind the biomarker proteins of interest, wherein the biomarker proteins of interest comprise sTIE-2, sVEGFR-1, FUT8, fucosylated TIMP-1 and fucosylated DPP-4;
   b. adding a mixture of biotinylated detection antibodies that specifically bind sTIE-2, sVEGFR-1 and FUT8;
   c. adding a mixture of biotinylated lectins that specifically bind fucosylated TIMP-1 and fucosylated DPP-4;
   d. adding a streptavidin labeled fluorescent marker that binds the biotinylated antibodies bound to sTIE-2, sVEGFR-1, and FUT8;
   e. adding a streptavidin labeled fluorescent marker that binds the biotinylated lectins bound to the fucosylated TIMP-1 and fucosylated DPP-4;
   d. detecting sTIE-2, sVEGFR-1, FUT8, fucosylated TIMP-1 and fucosylated DPP-4; and
   e. identifying the patient as having aggressive prostate cancer if the fluorescence intensity of sTIE-2, FUT8, fucosylated TIMP-1 and fucosylated DPP-4 is statistically significantly increased relative to a reference and the fluorescence intensity of sVEGFR-1 is statistically significantly decreased relative to a reference.

10. The multiplex assay of claim 9, wherein the sample is a serum sample.

11. The multiplex assay of claim 9, wherein the biotinylated lectin is *Ulex* europeaus agglutinin (UEA).

12. The multiplex assay of claim 9, wherein the biotinylated detection antibodies are immunoglobulin G antibodies.

13. The multiplex assay of claim 9, wherein the fluorescent marker is phycoerythrin.

14. The multiplex assay of claim 9, wherein the sample comprises about 300 ng of protein.

\* \* \* \* \*